United States Patent [19]

Sakamoto et al.

[11] Patent Number: 5,698,702
[45] Date of Patent: Dec. 16, 1997

[54] INTERMEDIATE COMPOUND FOR USE IN PRODUCTION OF DIHALOPROPENE COMPOUND

[75] Inventors: Noriyasu Sakamoto, Nishinomiya; Masaya Suzuki; Toshio Nagatomi, both of Takarazuka; Kazunori Tsushima, Sanda; Kimitoshi Umeda, Takarazuka, all of Japan

[73] Assignee: Sumitomo Chemical Company, Limited, Osaka-fu, Japan

[21] Appl. No.: 600,179

[22] Filed: Feb. 12, 1996

Related U.S. Application Data

[62] Division of Ser. No. 325,597, Oct. 19, 1994, Pat. No. 5,530,015.

[30] Foreign Application Priority Data

Oct. 19, 1993 [JP] Japan .................. 5-261380

[51] Int. Cl.⁶ .................. C07D 213/64; C07D 213/643; C07D 43/23; C07D 43/225
[52] U.S. Cl. .................. 546/302; 546/304; 568/639
[58] Field of Search .................. 546/297, 302, 546/304; 568/639

[56] References Cited

U.S. PATENT DOCUMENTS

| | | | |
|---|---|---|---|
| 4,048,235 | 9/1977 | Karrer | 260/613 R |
| 4,061,683 | 12/1977 | Karrer | 260/612 R |
| 4,496,440 | 1/1985 | Campbell et al. | 204/78 |
| 4,772,633 | 9/1988 | Matsuo | 514/717 |

FOREIGN PATENT DOCUMENTS

| | | |
|---|---|---|
| 0203798 | 12/1986 | European Pat. Off. . |
| 0218543 | 4/1987 | European Pat. Off. . |
| 227369 | 7/1987 | European Pat. Off. . |
| 55-120565 | 9/1980 | Japan . |
| 56-029504 | 3/1981 | Japan . |
| 1420171 | 1/1976 | United Kingdom . |
| 1424211 | 2/1976 | United Kingdom . |
| 1578412 | 11/1980 | United Kingdom . |

OTHER PUBLICATIONS

Sagi K, Kagechika H, Fukasawa H, Hashimoto Y, Shudo K. Chem. Pharm. Bull. 44(6), 1273-1275, 1996.

*Primary Examiner*—C. Warren Ivy
*Assistant Examiner*—Evelyn Huang
*Attorney, Agent, or Firm*—Birch, Stewart, Kolasch & Birch, LLP

[57] ABSTRACT

There is disclosed a dihalopropene compound of the formula I:

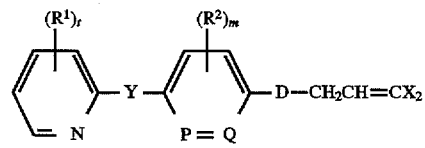

wherein l is an integer of 1 to 5; m is an integer of 1 to 4; $R^1$'s and $R^2$'s are the same or different and are independently halogen or various other groups; D is oxygen; X's are the same or different and are independently chlorine or bromine; Y is oxygen; Z, P and Q are the same or different and are independently nitrogen or CH, provided that P and Q are not simultaneously nitrogen, and when Y is sulfur, Z is CH. Also disclosed is an insecticide/acaricide comprising the dihalopropene compound as an active ingredient. The dihalopropene compound exhibits excellent insecticidal/acaricidal action. Further disclosed is an intermediate compound for use in the production of the dihalopropene compound.

8 Claims, No Drawings

INTERMEDIATE COMPOUND FOR USE IN PRODUCTION OF DIHALOPROPENE COMPOUND

This application is a divisional of application Ser. No. 08/325,597, file on Oct. 19, 1994, U.S. Pat. No. 5,530,015 the entire contents of which are hereby incorporated by reference.

FIELD OF THE INVENTION

The present invention relates to a dihalopropene compound, and an insecticide/acaricide containing the dihalopropene compound as an active ingredient. It also relates to an intermediate compound for use in the production of the dihalopropene compound.

DESCRIPTION OF THE RELATED ART

In the Japanese Patent Laid-open Publication Nos. 48-86835/1973 and 49-1526/74, it is disclosed that certain propene compounds can be used as an active ingredient of insecticides.

However, these compounds are not necessarily sufficient as the active ingredient of insecticides/acaricides in view of insecticidal activity.

SUMMARY OF THE INVENTION

Under these circumstances, the present inventors have studied intensively to find a compound having an excellent insecticidal/acaricidal activity. As a result, they have found that particular dihalopropene compounds have an excellent insecticidal/acaricidal activity, thereby completing the present invention.

That is, the present invention provides a dihalopropene compound of the formula I:

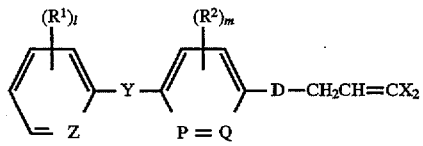

wherein $l$ is an integer of 1 to 5; m is an integer of 1 to 4; $R^1$ is halogen, cyano, acetamido, trifluoroacetamido, nitro, $C_1$–$C_8$ alkyl, $C_1$–$C_3$ haloalkyl, $C_1$–$C_7$ alkoxy, $C_1$–$C_3$ haloalkoxy, $C_1$–$C_3$ alkylthio, $C_1$–$C_3$ haloalkylthio, $C_3$–$C_6$ alkenyloxy, $C_3$–$C_6$ haloalkenyloxy, $C_1$–$C_3$ hydroxyalkyl, $C_2$–$C_4$ alkenyl, $C_2$–$C_4$ haloalkenyl, $C_2$–$C_4$ alkynyl, $C_2$–$C_4$ haloalkynyl, $C_3$–$C_6$ alkynyloxy, $C_3$–$C_6$ haloalkynyloxy, $C_2$–$C_4$ alkoxyalkyl, $C_2$–$C_4$ alkylthioalkyl, $C_3$–$C_6$ cycloalkyl, $C_5$–$C_6$ cycloalkenyl, $C_3$–$C_6$ cycloalkyloxy, $C_5$–$C_6$ cycloalkenyloxy, phenyl, pyridyloxy, phenoxy or benzyl, the last four of which may be optionally substituted with halogen, $C_1$–$C_5$ alkyl, $C_1$–$C_3$ alkoxy, $C_1$–$C_3$ haloalkyl or $C_1$–$C_3$ haloalkoxy, with the proviso that when $l$ is an integer of 2 to 5, $R^1$'s are the same or different, or two adjacent $R^1$'s may be combined together at their terminal ends to form trimethylene, tetramethylene, methylenedioxy, ethylenedioxy or CH=CH—CH=CH; $R^2$ is halogen, $C_1$–$C_5$ alkyl, $C_1$–$C_3$ haloalkyl, $C_1$–$C_3$ alkoxy, $C_1$–$C_3$ haloalkoxy, $C_2$–$C_4$ alkenyl, $C_2$–$C_4$ haloalkenyl, $C_2$–$C_4$ alkynyl, $C_2$–$C_4$ haloalkynyl, $C_2$–$C_4$ alkoxyalkyl, $C_2$–$C_4$ alkoxyimino, allyloxyimino, nitro or phenyl which may be optionally substituted with halogen, $C_1$–$C_5$ alkyl or $C_1$–$C_3$ alkoxy, with the proviso that when m is an integer of 2 to 4, $R^2$'s are the same or different, or two adjacent $R^2$'s may be combined together at their terminal ends to form trimethylene or tetramethylene; D is oxygen, NH or sulfur; X's are the same or different and are independently chlorine or bromine; Y is oxygen, $NR^3$, $S(O)q$, $C(R^4)_2$, $C=C(R^4)_2$ or $C(CF_3)_2$, wherein $R^3$ is hydrogen, $C_1$–$C_2$ alkyl, trifluoroacetyl or acetyl, $R^4$'s are the same or different and are independently hydrogen or $C_1$–$C_3$ alkyl, and q is an integer of 0 to 2; Z, P and Q are the same or different and are independently nitrogen or CH, with the proviso that P and Q are not simultaneously nitrogen, and when Y is sulfur, Z is CH, and an insecticide/acaricide containing the dihalopropene compound as an active ingredient.

It is another object of the present invention to provide intermediate compounds for use in the production of the above dihalopropene compound.

DESCRIPTION OF THE INVENTION

For the substituents $R^1$ and $R^2$, examples of the halogen are fluorine, chlorine, bromine and iodine.

For the substituent $R^1$, examples of the $C_1$–$C_8$ alkyl are methyl, ethyl, n-propyl, isopropyl, n-butyl, isobutyl, sec-butyl, tert-butyl, n-pentyl, isopentyl, neopentyl, tert-pentyl, n-hexyl, n-heptyl, tert-octyl, 3-n-pentyl and the like.

For the substituents $R^1$ and $R^2$, examples of the $C_1$–$C_3$ haloalkyl are trifluoromethyl, difluoromethyl, bromodifluoromethyl, 2,2,2-trifluoroethyl, 2-fluoroethyl, 2-chloroethyl, 2-bromoethyl, 1-fluoroethyl, 1-chloroethyl, 1-bromoethyl, 3,3,3,2,2-pentafluoro-n-propyl, 3,3,3-trifluoro-n-propyl, 1-fluoro-n-propyl, 2-chloro-n-propyl, 3-bromo-n-propyl and the like.

For the substituent $R^1$, examples of the $C_1$–$C_7$ alkoxy are methoxy, ethoxy, n-propoxy, isopropoxy, n-butoxy, sec-butoxy, isobutoxy, tert-butoxy, n-pentyloxy, isopentyloxy, neopentyloxy, tert-pentyloxy, 3-n-pentyloxy, n-hexyloxy, n-heptyloxy and the like.

For the substituents $R^1$ and $R^2$, examples of the $C_1$–$C_3$ haloalkoxy are trifluoromethoxy, difluoromethoxy, bromodifluoromethoxy, 2-fluoroethoxy, 2,2,2-trifluoroethoxy, 2-chloroethoxy, 2-bromoethoxy, 2-chloro-1,1,2-trifluoroethoxy, 2-bromo-1,1,2-trifluoroethoxy, 1,1,2,2-tetrafluoroethoxy, 3,3,3,2,2,1-hexafluoro-n-propoxy, 3-fluoro-n-propoxy, 3-chloro-n-propoxy, 3-bromo-n-propoxy, 3,3,3,2,2-pentafluoro-n-propoxy, 3,3,3-n-propoxy, 2,2,2,1,1-pentafluoroethoxy and the like.

For the substituent $R^1$, examples of the $C_1$–$C_3$ alkylthio are methylthio, ethylthio, n-propylthio, isopropylthio and the like.

For the substituent $R^1$, examples of the $C_1$–$C_3$ haloalkylthio are trifluoromethylthio, difluoromethylthio, bromodifluoromethylthio, 2,2,2-trifluoroethylthio, 2-chloro-1,1,2-trifluoroethylthio, 2-bromo-1,1,2-trifluoroethylthio, 1,1,2,2-tetrafluoroethylthio, 2-chloroethylthio, 2-fluoroethylthio, 2-bromoethylthio, 3-fluoro-n-propylthio, 3-chloro-n-propylthio, 3-bromo-n-propylthio, 3,3,3,2,2-pentafluoro-n-propylthio, 3,3,3-trifluoro-n-propylthio and the like.

For the substituent $R_1$, examples of the $C_3$–$C_6$ alkenyloxy are allyloxy, 2-methylallyloxy, 2-butenyloxy, 3-methyl-2-butenyloxy, 2-methyl-2-butenyloxy, 2-pentenyloxy, 2-hexenyloxy and the like.

For the substituent $R^1$, examples of the $C_3$–$C_6$ haloalkenyloxy are 3,3-dichloroallyloxy, 3,3-dibromoallyloxy, 2,3-dichloroallyloxy, 2,3-dibromoallyloxy, 2-chloro-2-propenyloxy, 3-chloro-2-propenyloxy, 2-bromo-2-propenyloxy, 3-chloro-2-butenyloxy and the like.

For the substituent $R^1$, examples of the $C_1$–$C_3$ hydroxyalkyl are hydroxymethyl, 2-hydroxyethyl, 1-hydroxyethyl, 3-hydroxy-n-propyl, 2-hydroxy-n-propyl, 1-hydroxy-n-propyl and the like.

For the substituents $R^1$ and $R^2$, examples of the $C_2$–$C_4$ alkenyl are vinyl, isopropenyl, n-1-propenyl, 2-methyl-1-propenyl, 1-methyl-1-propenyl, allyl, 2-methylpropenyl, 2-n-butenyl and the like.

For the substituents $R^1$ and $R^2$, examples of the $C_2$–$C_4$ haloalkenyl are 2,2-dichloroethenyl, 2,2-dibromoethenyl, 3,3-dichloroallyl, 3,3-dibromoallyl, 2,3-dichloroallyl, 2,3-dibromoallyl, 2-chloro-2-propenyl, 3-chloro-2-propenyl, 2-bromo-2-propenyl, 3-chloro-2-butenyl and the like.

For the substituents $R^1$ and $R^2$, examples of the $C_2$–$C_4$ alkynyl are ethynyl, 1-propynyl, 2-propenyl, 1-methyl-2-propynyl and the like.

For the substituents $R_1$ and $R^2$, examples of the $C_2$–$C_4$ haloalkynyl are chloroethynyl, bromoethynyl, iodoethynyl, 3-chloro-2-propynyl, 3-bromo-2-propynyl, 3-iodo-2-propynyl, 1-methyl-3-chloro-2-propynyl, 1-methyl-3-bromo-2-propynyl, 1-methyl-3-iodo-2-propynyl and the like.

For the substituent $R^1$, examples of the $C_3$–$C_6$ alkynyloxy are 2-propynyloxy, 1-methyl-2-propynyloxy, 3-butynyloxy, 2-hexynyloxy, 3-hexynyloxy, 2-methyl-3-bytynyloxy, 1-methyl-3-bytynyloxy and 2-pentynyloxy.

For the substituent $R_1$, examples of the $C_3$–$C_6$ haloalkynyloxy are 3-chloro- 2-propynyloxy, 3-bromo-2-propynyloxy, 1-methyl-3-chloro-2-propynyloxy, 1-methyl-3-bromo-2-propynyloxy, 4-chloro-3-bytynyloxy, 4-bromo-3-bytynyloxy, 2-methyl-4-chloro-3-butynyloxy, 2-methyl-4-bromo-3-butynyloxy, 1-methyl-4-chloro-3-butynyloxy and 1-methyl-4-bromo-3-butynyloxy.

For the substituents $R^1$ and $R^2$, examples of the $C_2$–$C_4$ alkoxyalkyl are methoxymethyl, ethoxymethyl, n-propyloxymethyl, isopropyloxymethyl, 2-methoxyethyl, 1-methoxyethyl, 2-ethoxyethyl, 1-ethoxyethyl, 3-methoxy-n-propyl, 2-methoxy-n-propyl, 1-methoxy-n-propyl, 2-methoxy-1-methylethyl and the like.

For the substituent $R_1$, examples of the $C_2$–$C_4$ alkylthioalkyl are methylthiomethyl, ethylthiomethyl, n-propylthiomethyl, isopropylthiomethyl, 2-methylthioethyl, 1-methylthioethyl, 2-ethylthioethyl, 1-ethylthioethyl, 3-methylthio-n-propyl, 2-methylthio-n-propyl, 1-methylthio-n-propyl, 2-methylthio-1-methylethyl and the like.

For the substituent $R^1$, examples of the $C_3$–$C_5$ cycloalkyl are cyclopropyl, cyclobutyl, cyclopentyl, cyclohexyl and the like.

For the substituent $R_1$, examples of the $C_5$–$C_6$ cycloalkenyl are 1-cyclopentenyl, 2-cyclopentenyl, 3-cyclopentenyl, 1-cyclohexenyl, 2-cyclohexenyl, 3-cyclohexenyl and the like.

For the substituent $R^1$, examples of the $C_3$–$C_6$ cycloalkyloxy are cyclopropyloxy, cyclobutyloxy, cyclopentyloxy, cyclohexyloxy and the like.

For the substituent $R^1$, examples of the $C_5$–$C_6$ cycloalkenyloxy are 1-cyclopentenyloxy, 2-cyclopentenyloxy, 3-cyclopentenyloxy, 1-cyclohexenyloxy, 2-cyclohexenyloxy, 3-cyclohexenyloxy and the like.

Examples of the $C_1$–$C_5$ alkyl group which may be optionally present on the phenyl or phenoxy for the substituents $R_1$ and/or $R^2$ are methyl, ethyl, n-propyl, isopropyl, n-butyl, isobutyl, sec-butyl, tert-butyl, n-pentyl, isopentyl, neopentyl, tert-pentyl and the like.

When $R^1$ and $R^2$ are independently phenyl, pyridyloxy, benzyl or phenoxy. all of which may be optionally substituted with $C_1$–$C_3$ alkoxy, examples of the $C_1$–$C_3$ alkoxy are methoxy, ethoxy, n-propoxy and i-propoxy.

For the substituent $R^2$, examples of the $C_2$–$C_4$ alkoxyimino are methoxyimino, ethoxyimino, n-propoxyimino, isopropoxyimino and the like.

Examples of the $C_1$–$C_5$ alkoxy which may be optionally present on the phenyl for the substituent $R^2$ are methoxy, ethoxy, n-propyloxy, isopropyloxy, n-butoxy, sec-butoxy, isobutoxy, tert-butoxy, n-pentyloxy, 3-n-pentyloxy, isopentyloxy, neopentyloxy, tert-pentyloxy group and the like.

For the substituent $R^3$, examples of the $C_1$–$C_3$ alkyl are methyl, n-propyl, ethyl, isopropyl group and the like.

For the substituents $R^4$ and $R^5$, examples of the $C_1$–$C_2$ alkyl are methyl or ethyl.

Among the dihalopropene compounds of the present invention, preferable compounds are those defined as follows: $R^1$ is halogen, $C_1$–$C_8$ alkyl, $C_1$–$C_3$ haloalkyl, $C_1$–$C_7$ alkoxy, $C_1$–$C_3$ haloalkoxy, $C_3$–$C_6$ alkenyloxy, $C_3$–$C_6$ haloalkenyloxy, $C_3$–$C_6$ cycloalkyl, phenyl, pyridyloxy, phenoxy or benzyl, the last four of which may be optionally substituted with halogen $C_1$–$C_5$ alkyl, $C_1$–$C_3$ alkoxy, $C_1$–$C_3$ haloalkyl or $C_1$–$C_3$ haloalkoxy, with the proviso that when l is an integer of 2 to 5, $R^1$'s are the same or different, or two adjacent $R^1$'s may be combined together at their terminal ends to form trimethylene, tetramethylene, methylenedioxy, ethylenedioxy or CH=CH—CH=CH; $R^2$ is halogen, nitro, $C_1$–$C_5$ alkyl, $C_1$–$C_3$ haloalkyl, $C_2$–$C_4$ alkenyl, $C_2$–$C_4$ haloalkenyl, $C_2$–$C_4$ alkynyl, $C_2$–$C_4$ alkoxyalkyl, $C_2$–$C_4$ alkoxyimino, allyloxyimino or phenyl which may be optionally substituted with halogen, $C_1$–$C_5$ alkyl or $C_1$–$C_3$ alkoxy, with the proviso that when m is an integer of 2 to 4, $R^2$'s are the same or different, or two adjacent $R^2$'s may be combined together at their terminal ends to form trimethylene or tetramethylene; D is oxygen; X's are the same or different and are independently chlorine or bromine; Y is oxygen, $NR^3$, sulfur or $C(R^4)_2$, wherein $R^3$ is hydrogen or $C_1$–$C_2$ alkyl and $R^4$'s are the same or different and are independently hydrogen or $C_1$–$C_3$ alkyl; Z is nitrogen or CH, with the proviso that when Y is sulfur, Z is CH; P and Q are CH.

More preferably, when Z is CH, $R^1$ is halogen, $C_1$–$C_8$ alkyl, trifluoromethyl, $C_1$–$C_2$ haloalkoxy, $C_1$–$C_4$ alkoxy, $C_3$–$C_5$ alkenyloxy, $C_3$–$C_4$ haloalkenyloxy, cyclohexyl, cyclopentyl, phenyl, phenoxy or pyridyloxy which may be optionally substituted with halogen, $C_1$–$C_4$ alkyl or trifluoromethyl, with the proviso that when l is an integer of 2 or 3, $R^1$'s are the same or different, or two adjacent $R^1$'s may be combined together at their terminal ends to form trimethylene, tetramethylene, methylenedioxy, ethylenedioxy or CH=CH—CH=CH; and when Z is nitrogen, $R^1$ is halogen, trifluoromethyl or nitro; $R^2$ is halogen, $C_1$–$C_4$ alkyl, trifluoromethyl, $C_3$–$C_4$ alkenyl, $C_3$–$C_4$ haloalkenyl, ethynyl, methoxymethyl, nitro, $C_1$–$C_2$ alkoxyimino, allyloxyimino or phenyl, with the proviso that m is an integer of 2 or 3, $R^2$'s are the same or different, or two adjacent $R^2$'s may be combined together at their terminal ends to form tetramethylene; D is oxygen; X's are the same or different and are independently chlorine or bromine; when Z is CH, Y is oxygen, $NR^3$, sulfur or $C(CH_3)_2$, wherein $R^3$ is as defined above, and when Z is nitrogen, Y is oxygen or NH; P and Q are CH.

Most preferably, when Z is CH, l is an integer 1 to 3 $R^1$ is halogen, $C_1$–$C_2$ haloalkyl, $C_3$–$C_4$ alkyl, $C_1$–$C_4$ alkoxy, $C_1$–$C_3$ haloalkoxy, cyclohexyl, cyclopentyl, phenyl or phenoxy, with the proviso that when l is an integer of 2 or 3, $R^1$'s the same or different, or two adjacent $R^1$'s may be combined together at their terminal ends to form tetramethylene, methylenedioxy or CH=CH—CH=CH, and $R^2$ is halogen, trifluoromethyl, allyl or $C_3$ alkyl; and when Z is nitrogen, m is an integer of 1 or 2 $R^1$ is halogen or trifluoromethyl, and $R^2$ is halogen or methyl, with the proviso that when m is an integer of 1 or 2 $R^2$'s are the same or different, D is oxygen; X's are the same or different and are independently chlorine or bromine; when Z is CH, Y is oxygen, sulfur or $C(CH_3)_2$, and when Z is nitrogen, Y is oxygen or NH; P and Q are CH.

The dihalopropene compounds of the present invention can be produced by the following production processes.

Production process A

The process A for producing the dihalopropene compounds of the present invention comprises reacting a compound of the formula II:

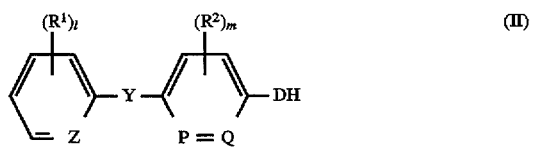

wherein $R^1 R^2$, Y, D, Z, P, Q, l and m are each as defined above, with a compound of the formula III:

L—CH$_2$CH=CX$_2$ (III)

wherein X is as defined above; and L is halogen such as chlorine, bromine or iodine, mesyloxy or tosyloxy.

The raw material compound of the formula II is obtained by conventional production processes as depicted in the Schemes below, and examples of the intermediates are also listed therein.

The intermediate compounds include novel compounds of the formula:

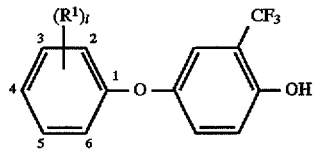

wherein $R^1$ is halogen, $C_1$-$C_8$ alkyl, $C_1$-$C_3$ haloalkyl, $C_1$-$C_4$ alkoxy, $C_1$-$C_2$ haloalkoxy, $C_3$-$C_5$ alkenyloxy, $C_3$-$C_4$ haloalkenyloxy, $C_3$-$C_6$ cycloalkyl, phenyl, pyridyloxy, phenoxy or benzyl, the last four of which may be optionally substituted with halogen or $C_1$-$C_5$ alkyl, $C_1$-$C_3$ alkoxy, $C_1$-$C_3$ haloalkoxy or $C_1$-$C_3$ haloalkxyl, with the proviso that when l is an integer of 2 to 5, the $R^1$'s are the same or different, and when l is an integer of 2 or 3, two adjacent $R^1$'s may be combined together at their terminal ends to form trimethylene, tetramethylene, methylenedioxy, ethylenedioxy or CH=CH—CH=CH.

The intermediate compounds further include novel compounds of the formula:

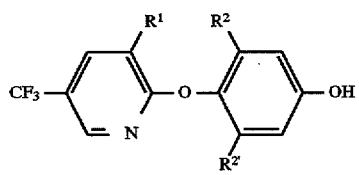

wherein $R^1$ is halogen such as fluorine, chlorine, bromine or iodine, or trifluoromethyl; and $R^2$ and $R^{2'}$ are the same or different and are independently fluorine, chlorine, trifluoromethyl or methyl.

Alternatively, the novel intermediate compounds may be of the formula:

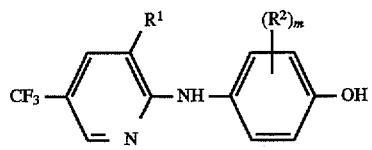

wherein $R^1$ is halogen such as fluorine, chlorine, bromine or iodine, or trifluoromethyl; $R^2$ is halogen, trifluoromethyl or $C_1$-$C_3$ alkyl; and m is an integer of 1 to 4.

The above reaction is usually carried out in an inert solvent under the presence of a suitable base.

Examples of the solvent to be used are ketones such as acetone, methyl ethyl ketone and cyclohexanone, ethers such as 1,2-dimethoxyethane, tetrahydrofuran, dioxane and $C_1$-$C_4$ dialkyl ether (e.g., diethyl ether, diisopropyl ether), N,N-dimethylformamide, dimethylsulfoxide, hexamethylphosphorous triamide, sulfolane, acetonitrile, nitromethane, halogenated hydrocarbons such as dichloromethane, chloroform, 1,2-dichloroethane and chlorobenzene, hydrocarbons such as toluene, benzene and xylene, and water. These solvents can be used alone or in combination.

Examples of the base to be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, sodium carbonate, potassium carbonate and calcium carbonate; hydrides of alkali metals or alkaline earth metals, such as lithium hydride, sodium hydride, potassium hydride and calcium hydride; $C_1$-$C_4$ alkoxides of alkali metals, such as sodium methoxide, sodium ethoxide and potassium tert-butoxide; organic bases such as triethylamine and pyridine. If necessary, a catalyst such as an ammonium salt (e.g., triethylbenzylammonium chloride) may be added to the reaction system in an proportion of 0.01 to 1 mole to 1 mole of the compound II.

The reaction temperature may be usually in the range of from −20° C. to the boiling point of a solvent used for the reaction or 150° C., more preferably from −5° C. to the boiling point of the solvent used for the reaction or 100° C.

The molar ratio of the raw material and base to be used for the reaction can optionally be set, but it is advantageous to conduct the reaction using them in the equimolar ratio or in a ratio similar thereto.

After completion of the reaction, the reaction solution can be subjected to ordinary post-treatments such as organic solvent extraction and/or concentration to isolate the desired compound. If necessary, the resultant compound can be purified by a method such as chromatography or recrystallization.

Production process B

The process B for producing the dihalopropene compound of the present invention comprises reacting the compound of the formula II with an alcohol compound of the formula IV:

HO—CH$_2$CH=CX$_2$ (IV)

wherein X is as defined above.

It is preferred that the above reaction is carried out in an inert solvent under the presence of a suitable dehydrating agent.

Examples of the dehydrating agent are dicyclohexylcarbodiimide, di($C_1$–$C_4$ alkyl)azodicarboxylate (e.g., diethylazodicarboxylate, diisopropylazodicarboxylate), tri($C_1$–$C_{20}$ alkyl)phosphine or triarylphosphine (e.g., triphenylphosphine, trioctylphosphine, tributylphosphine) and the like.

Examples of the solvent to be used are hydrocarbons such as benzene, xylene and toluene; ethers such as diethyl ether, diisopropyl ether, tetrahydrofuran and dioxane; halogenated hydrocarbons such as carbon tetrachloride, dichloromethane, chlorobenzene and dichlorobenzene.

The reaction temperature may be usually in the range of from –20° C. to 200° C. or the boiling point of a solvent used for the reaction.

The molar ratio of the raw material and dehydrating agent to be used for the reaction can optionally be set, but it is advantageous to conduct the reaction using them in the equimolar ratio or in a ratio similar thereto.

After completion of the reaction, the reaction solution can be subjected to ordinary post-treatments such as organic solvent extraction and/or concentration to isolate the desired compound. If necessary, the resultant compound can be purified by a method such as chromatography or recrystallization.

Production process C (when D is an oxygen atom in the dihalopropene compound of the present invention):

The production process C for producing the dihalopropene compound of the present invention comprises reacting an aldehyde compound of the formula V:

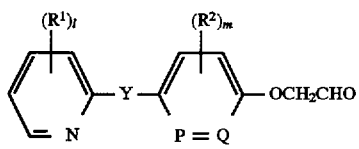

wherein $R^1$, $R^2$, Y, Z, P, Q, l and m are each as defined above, with carbon tetrachloride or carbon tetrabromide.

It is preferred that the above reaction is carried out in an inert solvent under the presence of a suitable trialkylphosphine or triarylphosphine, if necessary, under the presence of metallic zinc.

Examples of the solvent to be used are hydrocarbons such as benzene, xylene and toluene; ethers such as diethyl ether, diisopropyl ether, tetrahydrofuran and dioxane; halogenated hydrocarbons such as dichloromethane, 1,2-dichloroethane and chlorobenzene (excluding carbon tetrabromide and carbon tetrachloride).

The reaction temperature may be usually in the range of from –30° C. to the boiling point of a solvent used for the reaction or 150° C.

Examples of the ($C_1$–$C_{20}$ trialkyl)phosphine or triarylphosphine are triphenylphosphine, trioctylphosphine and the like. It is preferred that metallic zinc optionally used is in a dust form.

The molar ratio of the raw material and reagent to be used for the reaction can optionally be chosen. The proportion of carbon tetrabromide (tetrachloride), trialkylphosphine or triarylphosphine and metallic zinc is 2 moles, 2 or 4 moles and 2 moles, respectively, to 1 mole of the aldehyde compound of the formula V.

After completion of the reaction, the reaction solution can be subjected to ordinary post-treatments such as organic solvent extraction and/or concentration to isolate the desired compound. If necessary, the resultant compound can be purified by a method such as chromatography or recrystallization.

If the dihalopropene compound of the present invention contains an asymmetric atom, the corresponding optically-active isomers having biological activity (e.g., (+)-isomer, (–)-isomer) and mixtures of these isomers in any ratio are also included in the present invention.

Some examples of the present dihalopropene compound of the present invention will be shown below; however, the present invention is not limited thereto.

The compound of the following formulae VI-1 to VI-6 are shown in Table 1.

TABLE 1

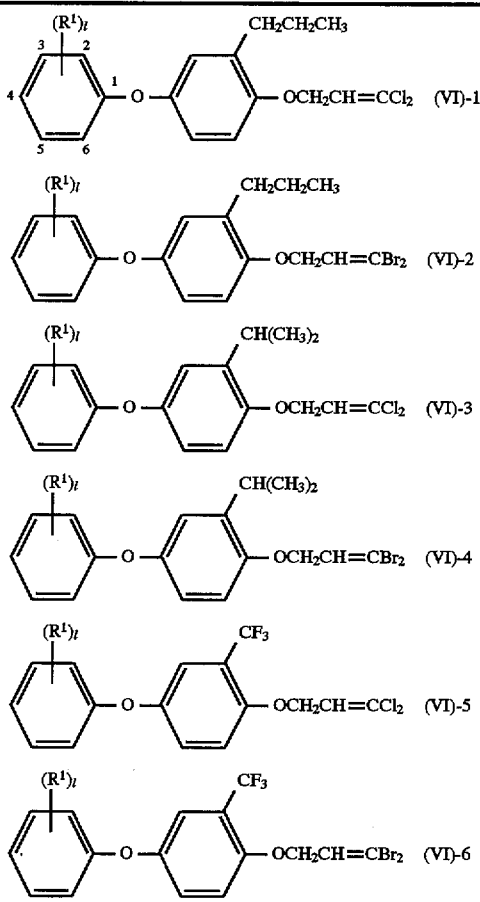

| $(R^1)_l$ | $(R^1)_l$ |
|---|---|
| 2-F | 2,3,4-$Cl_3$ |
| 3-F | 2,3,6-$Cl_3$ |
| 4-F | 2,4,6-$Cl_3$ |
| 2,3-$F_2$ | 2,3,5-$Cl_3$ |
| 3,4-$F_2$ | 2,4,5-$Cl_3$ |
| 2,6-$F_2$ | 2,3,4,5,6-$Cl_3$ |
| 2,4-$F_2$ | 2-Br |
| 2,5-$F_2$ | 3-Br |
| 3,5-$F_2$ | 4-Br |
| 2,3,4-$F_3$ | 3,5-$Br_2$ |
| 2,3,6-$F_3$ | 2,4-$Br_2$ |
| 2,3,5-$F_3$ | 2-I |
| 2,4,5-$F_3$ | 3-I |
| 2,3,5,6-$F_4$ | 4-I |
| 2,3,4,5,6-$F_5$ | 2-F, 4-Cl |
| 2-Cl | 3-F, 4-Cl |
| 3-Cl | 3-Cl, 4-F |
| 4-Cl | 2-Br, 4-F |
| 2,3-$Cl_2$ | 2-F, 4-Br |
| 2,6-$Cl_2$ | 2-Br, 5-F |
| 3,5-$Cl_2$ | 2-Br, 4-Cl |
| 2,4-$Cl_2$ | 2-Cl, 4-F |

TABLE 1-continued

| | |
|---|---|
| 3,4-Cl₂ | 2-Cl, 4-Br |
| 2,5-Cl₂ | 3-CH₃ |
| 2-Cl, 4-OCH₃ | 3-C₂H₅ |
| 3-CH₃, 4-Cl | 3-CH(CH₃)₂ |
| 2-CH₃, 4-F | 3-C(CH₃)₃ |
| 3-CH₃, 4-F | 3-CH₂CH₂CH₂CH₃ |
| 2-Cl, 4-CH₃ | 3-CH(CH₃)CH₂CH₃ |
| 2-Cl, 5-CH₃ | 3-CH₂CH(CH₃)₂ |
| 2-CH₃, 4-Cl | 3-(CH₂)₄CH₃ |
| 3-C₂H₅, 4-Cl | 3-CH(CH₃)(CH₂)₂CH₃ |
| 2-Br, 4-CH₃ | 3-CH(CH₃)CH(CH₃)₂ |
| 2-CH₃, 4-I | 3-CH(C₂H₅)₂ |
| 2-Cl, 5-CF₃ | 3-C(CH₃)₂CH₂CH₃ |
| 2,4-Cl₂, 3-CH₃ | 3-(CH₂)₅CH₃ |
| 4-Cl, 3,5-(CH₃)₂ | 3-(CH₂)₆CH₃ |
| 4-Br, 3,5-(CH₃)₂ | 3-(CH₂)₇CH₃ |
| 4-Br, 2,6-(CH₃)₂ | 4-CH₃ |
| 4-Cl, 4,5-(CH₃)₂ | 4-C₂H₅ |
| 2-CH(CH₃)₂, 4-Cl, 5-CH₃ | 4-CH₂CH₂CH₃ |
| 2-CH₃ | 4-CH(CH₃)₂ |
| 2-C₂H₅ | 4-(CH₂)₃CH₃ |
| 2-CH₂CH₂CH₃ | 4-CH(CH₃)CH₂CH₃ |
| 2-CH(CH₃)₂ | 4-CH₂CH(CH₃)₂ |
| 2-CH(CH₃)CH₂CH₃ | |
| 2-C(CH₃)₃ | 4-C(CH₃)₃ |
| 4-(CH₂)₄CH₃ | 2-Br, 4-(CH₂)₂CH₃ |
| 4-CH(CH₃)(CH₂)₂CH₃ | 2-Br, 4-CH(CH₃)₂ |
| 4-CH(CH₃)CH(CH₃)₂ | 2-Br, 4-(CH₂)₃CH₃ |
| 4-CH(C₂H₅)₂ | 2-Br, 4-CH(CH₃)CH₂CH₃ |
| 4-C(CH₃)₂CH₂CH₃ | 2-Br, 4-CH₂CH(CH₃)₂ |
| 4-(CH₂)₅CH₃ | 2-Br, 4-C(CH₃)₃ |
| 4-(CH₂)₆CH₃ | 2-Br, 4-(CH₂)₄CH₃ |
| 4-(CH₂)₇CH₃ | 2-Br, 4-CH(CH₃)(CH₂)₂CH₃ |
| 4-C(CH₃)₂CH₂C(CH₃)₃ | 2-Br, 4-CH(CH₃)CH(CH₃)₂ |
| 2-Cl, 4-C₂H₅ | 2-Br, 4-CH(C₂H₅)₂ |
| 2-Cl, 4-CH₂CH₂CH₃ | 2-Br, 4-C(CH₃)₂CH₂CH₃ |
| 2-Cl, 4-CH(CH₃)₂ | 2-CF₃ |
| 2-Cl, 4-(CH₂)₃CH₃ | 3-CF₃ |
| 2-Cl, 4-CH(CH₃)CH₂CH₃ | 4-CF₃ |
| 2-Cl, 4-CH₂CH(CH₃)₂ | 3,5-(CF₃)₂ |
| 2-Br, 4-CH₂CH(CH₃)₂ | 2,4-(CF₃)₂ |
| 2-Br, 4-CH₂CH(CH₃)₂ | 2-F, 4-CF₃ |
| 2-Cl, 4-C(CH₃)₃ | 2-Cl, 4-CF₃ |
| 2-Cl, 4-(CH₂)₄CH₃ | 2,6-Cl₂, 4-CF₃ |
| 2-Cl, 4-CH(CH₃)(CH₂)₂CH₃ | 2-CF₃, 4-Cl |
| 2-Cl, 4-CH(CH₃)CH(CH₃)₂ | 2-CF₃, 5-Cl |
| 2-Cl, 4-CH(C₂H₅)₂ | 2-Br, 4-CF₃ |
| 2-Cl, 4-C(CH₃)₂CH₂CH₃ | 2-CF₃, 4-Br |
| 2-Br, 4-C₂H₅ | 2-I, 4-CF₃ |
| 2-F, 6-Cl, 4-CF₃ | 3-OCH(CH₃)₂ |
| 2,6-F₂, 4-CF₃ | 3-O(CH₂)₃CH₃ |
| 2-CCl₃ | 3-OCH(CH₃)CH₂CH₃ |
| 4-CCl₃ | 3-OCH₂CH(CH₃)₂ |
| 2-CHF₂ | 3-OC(CH₃)₃ |
| 3-CHF₂ | 3-O(CH₂)₄CH₃ |
| 4-CHF₂ | 3-OCH(CH₃)(CH₂)₂CH₃ |
| 2-CF₂Br | 3-OCH(C₂H₅)₂ |
| 3-CF₂Br | 3-OCH(CH₃)CH(CH₃)₂ |
| 4-CF₂Br | 3-O(CH₂)₅CH₃ |
| 3-CH₂CF₃ | 3-O(CH₂)₆CH₃ |
| 4-CH₂CF₃ | 4-OCH₃ |
| 3-CH₂CH₂CF₃ | 4-OC₂H₅ |
| 4-CH₂CH₂CF₃ | 4-OCH₂CH₂CH₃ |
| 3-CH₂CF₂CF₃ | 4-OCH(CH₃)₂ |
| 4-CH₂CF₂CF₃ | 4-O(CH₂)₃CH₃ |
| 2-OCH₃ | 4-OCH(CH₃)CH₂CH₃ |
| 2-OC₂H₅ | 4-OCH₂CH(CH₃)₂ |
| 2-OCH₂CH₂CH₃ | 4-OC(CH₃)₃ |
| 2-OCH(CH₃)₂ | 4-O(CH₂)₄CH₃ |
| 3-OCH₃ | 4-OCH(CH₃)(CH₂)₂CH₃ |
| 3-OC₂H₅ | 4-OCH(CH₃)CH₂(CH₃)₂ |
| 3-OCH₂CH₂CH₃ | |
| 3-OC(CH₃)₂CH₂CH₃ | 4-OCH(C₂H₅)₂ |
| 4-OC(CH₃)₂CH₂CH₃ | 3,4,5-(OCH₃)₃ |
| 4-O(CH₂)₅CH₃ | 3-Cl, 5-OCH₃ |
| 4-O(CH₂)₆CH₃ | 2-Cl, 4-OC₂H₅ |
| 3,5-(C(CH₃)₃)₂ | 2-Cl, 4-OCH₂CH₂CH₃ |
| 3,5-(CH₃)₂ | 2-Cl, 4-OCHC(CH₃)₂ |
| | 2-Cl, 4-O(CH₂)₃CH₃ |

TABLE 1-continued

| | |
|---|---|
| 3-CH₃, 5-CH(CH₃)₂ | 2-Cl, 4-OCH(CH₃)CH₂CH₃ |
| 3,4-(CH₃)₂ | 2-Cl, 4-OCH₂CH(CH₃)₂ |
| 2,4-(CH₃)₂ | 2-Cl, 4-OC(CH₃)₃ |
| 2,5-(CH₃)₂ | 2-Cl, 4-O(CH₂)₄CH₃ |
| 2-CH(CH₃)₂, 5-CH₃ | 2-Cl, 4-OCH(CH₃)(CH₂)₂CH₃ |
| 3-CH₃, 4-CH(CH₃)₂ | 2-Cl, 4-OCH(CH₃)CH(CH₃)₂ |
| 2-CH₃, 5-CH(CH₃)₂ | 2-Cl, 4-OCH₂CH(C₂H₅)₂ |
| 2-C(CH₃)₃, 5-CH₃ | 2-Cl, 4-OC(CH₃)₂CH₂CH₃ |
| 2-C(CH₃)₃, 4-CH₃ | 2-Br, 4-OCH₃ |
| 2,4-(C(CH₃)₃)₂ | 2-Br, 4-OC₂H₅ |
| 2,3,5-(CH₃)₃ | 2-Br, 4-O(CH₂)₂CH₃ |
| 3,4,5-(CH₃)₃ | 2-Br, 4-OCH(CH₃)₂ |
| 2,4,6-(CH₃)₃ | 2-Br, 4-O(CH₂)₃CH₃ |
| 2,3-(OCH₃)₂ | 2-Br, 4-OCH(CH₃)CH₂CH₃ |
| 3,5-(OCH₃)₂ | 2-Br, 4-OCH₂CH(CH₃)₂ |
| 2-OCH₃, 4-CH₃ | 2-Br, 4-OC(CH₃)₃ |
| 3,4-(OCH₃)₂ | 2-Br, 4-O(CH₂)₄CH₃ |
| 3-C₂H₅, 4-OCH₃ | 2-CH₃, 4-OCH(CH₃)₂ |
| 2-Br, 4-OCH(CH₃)(CH₂)₂CH₃ | 2,3-(CH₃)₂, 4-OCH₃ |
| 2-Br, 4-OCH(CH₃)CH(CH₃)₂ | 2,3-(CH₃)₂, 4-OC₂H₅ |
| 2-Br, 4-OCH(C₂H₅)₂ | 2,3-(CH₃)₂, 4-OCH(CH₃)₂ |
| 2-Br, 4-OC(CH₃)₂CH₂CH₃ | 2-OCF₃ |
| 3-OCH₃, 5-OC₂H₅ | 3-OCF₃ |
| 3,5-(OC₂H₅)₂ | 4-OCF₃ |
| 3,5-(OCH(CH₃)₂)₂ | 2-OCHF₂ |
| 3-OCH₃, 5-OCH(CH₃)₂ | 3-OCHF₂ |
| 3-OC₂H₅, 5-OCH(CH₃)₂ | 4-OCHF₂ |
| 2-CH₃, 3-OCH₃ | 2-OCF₂Br |
| 2-CH₃, 3-OC₂H₅ | 3-OCF₂Br |
| 2-CH₃, 3-OCH(CH₃)₂ | 4-OCF₂Br |
| 2-CH₃, 3-OCH(CH₃)₂ | 3-OCH₂CF₃ |
| 3-OCH₃, 4-Cl | 4-OCH₂CF₃ |
| 3-OCH₃, 4-Br | 3-OCF₂CFHCl |
| 3-OC₂H₅, 4-Cl | 4-OCF₂CFHCl |
| 3-OC₂H₅, 4-Cl | 3-OCF₂CFHBr |
| 3-OCH(CH₃)₂, 4-Cl | 4-OCF₂CFHBr |
| 3-OCH(CH₃)₂, 4-Br | 3-OCF₂CF₂H |
| 3-CH₃, 5-OCH₃ | 4-OCF₂CF₂H |
| 3-CH₃, 5-OC₂H₅ | 3-OCH₂CH₂CF₃ |
| 3-CH₃, 5-OCH(CH₃)₂ | 4-OCH₂CH₂CF₃ |
| 2-CH₃, 4-OCH₃ | |
| 2-CH₃, 4-OC₂H₅ | 3-OCH₂CF₂CF₃ |
| 4-OCH₂CF₂CF₃ | 2-SCF₃ |
| 2-Cl, 4-OCF₃ | 3-SCF₃ |
| 2-Cl, 4-OCHF₂ | 4-SCF₃ |
| 2-Cl, 4-OCF₂Br | 3-SCHF₂ |
| 2-Cl, 4-OCH₂CF₃ | 4-SCHF₂ |
| 2-Cl, 4-OCH₂CH₂CF₃ | 3-SCF₂Br |
| 2-Cl, 4-OCH₂CF₂CF₃ | 4-SCF₂Br |
| 2-Cl, 4-OCF₂CF₂H | 3-SCH₂CF₃ |
| 2-Cl, 4-OCF₂CFHCl | 4-SCH₂CF₃ |
| 2-Cl, 4-OCF₂CFHBr | 3-SCF₂CFHCl |
| 3-OCF₂CF₃ | 4-SCF₂CFHCl |
| 4-OCF₂CF₃ | 3-SCF₂CFHBr |
| 2-SCH₃ | 4-SCF₂CFHBr |
| 3-SCH₃ | 3-SCF₂CF₂H |
| 4-SCH₃ | 4-SCF₂CF₂H |
| 2-CH₃, 4-SCH₃ | 3-SCH₂CF₂CF₃ |
| 2-SC₂H₅ | 4-SCH₂CF₂CF₃ |
| 3-SC₂H₅ | 3-SCH₂CH₂CF₃ |
| 3-SCH₂CH₂CH₃ | 4-SCH₂CH₂CF₃ |
| 3-SCH(CH₃)₂ | 3-SCF₂CF₃ |
| 4-SC₂H₅ | 4-SCF₂CF₃ |
| 4-S(CH₂)₂CH₃ | 3-CH₃, 4-SCH₃ |
| 4-SCH(CH₃)₂ | 3-OCH₂CH=CH₂ |
| 3-OCH(CH₃)CH=CH₂ | 4-OCH₂CH=CH₂ |
| 4-OCH(CH₃)CH=CH₂ | 3-OCH₂C(Br)=CH₂ |
| 3-OCH₂CH=CH(CH₃) | 4-OCH₂C(Br)=CH₂ |
| 4-OCH₂CH=CH(CH₃) | 3-OCH₂CH=CH(Cl)(CH₃) |
| 3-OCH₂CH=C(CH₃)₂ | 4-OCH₂CH=CH(Cl)(CH₃) |
| 4-OCH₂CH=C(CH₃)₂ | 3-CH₂OH |
| 3-OCH₂C(CH₃)=CHCH₃ | 4-CH₂OH |
| 4-OCH₂C(CH₃)=CHCH₃ | 3-CH(OH)CH₃ |
| 3-OCH₂CH=CHC₂H₅ | 4-CH(OH)CH₃ |
| 4-OCH₂CH=CHC₂H₅ | 3-CH₂CH₂OH |
| 3-OCH₂CH=CH(CH₂)₂CH₃ | 4-CH₂CH₂OH |
| 4-OCH₂CH=CH(CH₂)₂CH₃ | 3-CH(OH)CH₂CH₃ |
| 3-OCH₂CH=CCl₂ | 4-CH(OH)CH₂CH₃ |
| 4-OCH₂CH=CCl₂ | 3-CH₂CH(OH)CH₃ |

TABLE 1-continued

| | |
|---|---|
| 3-OCH$_2$CH=CBr$_2$ | 4-CH$_2$CH(OH)CH$_3$ |
| 4-OCH$_2$CH=CBr$_2$ | 3-CH$_2$CH$_2$CH$_2$OH |
| 3-OCH$_2$C(Cl)=CH(Cl) | 4-CH$_2$CH$_2$CH$_2$OH |
| 4-OCH$_2$C(Cl)=CH(Cl) | 3-cyclopentyl |
| 3-OCH$_2$C(Br)=CH(Br) | 4-cyclopentyl |
| 4-OCH$_2$C(Br)=CH(Br) | 3-cyclohexyl |
| 3-OCH$_2$C(Cl)=CH$_2$ | 4-cyclohexyl |
| 4-OCH$_2$C(Cl)=CH$_2$ | 3-phenyl |
| 3-OCH$_2$CH=CH(Cl) | 4-phenyl |
| 4-OCH$_2$CH=CH(Cl) | 3-O-cyclopentyl |
| 4-O-cyclopentyl | 2-Cl, 4-cyclohexyl |
| 3-O-cyclohexyl | 2-Cl, 4-phenyl |
| 4-O-cyclohexyl | 2-Cl, 4-cyclohexyl |
| 3-phenoxy | 2-Cl, 4-O-cyclopentyl |
| 4-phenoxy | 2-Cl, 4-O-cyclohexyl |
| 2-Cl, 4-cyclopentyl | 2-Cl, 4-phenoxy |
| 4-(4-isopropoxyphenoxy) | 4-CH$_2$C$_6$H$_5$ |
| 4-(3-isopropoxyphenoxy) | 3-CH$_2$C$_6$H$_5$ |
| 4-(4-ethoxyphenoxy) | 4-(3-chloro-5-trifluoromethyl-2-pyridyloxy) |
| 4-(3-ethoxyphenoxy) | 4-(3-bromo-5-trifluoromethyl-2-pyridyloxy) |
| 4-(4-n-propoxyphenoxy) | 4-(3-5-bistrifluoromethyl-2-pyridyloxy) |
| 4-(4-methoxyphenoxy) | 2-methyl-4-(3,3-dichloro-2-allyloxy) |
| 4-(3-methoxyphenoxy) | 2-methyl-4-(3,3-dibromo-2-allyloxy) |
| 4-(3-n-propoxyphenoxy) | 2-CH$_3$, 3,4-ethylenedioxy |
| 2-Cl, 3,4-ethylenedioxy | 4-(4-trifluoromethoxyphenoxy) |
| 4-(3-trifluoromethoxyphenoxy) | |
| 4-OCH$_2$C≡CH | |
| 4-OCH$_2$C≡CBr | |
| 4-OCH$_2$C≡CCl | |
| 3-OCH$_2$C≡CH | |
| 3-OCH$_2$C≡CCl | |
| 3-OCH$_2$C≡CBr | |

The compounds of the following formulae VII-1 to 18 are shown in Table 2.

TABLE 2

(R$^1$)$_l$-C$_6$H$_4$-O-C$_6$H$_3$(Cl)-OCH$_2$CH=CCl$_2$  (VII)-1

(R$^1$)$_l$-C$_6$H$_4$-O-C$_6$H$_3$(Cl)-OCH$_2$CH=CBr$_2$  (VII)-2

(R$^1$)$_l$-C$_6$H$_4$-O-C$_6$H$_3$(Br)-OCH$_2$CH=CCl$_2$  (VII)-3

(R$^1$)$_l$-C$_6$H$_4$-O-C$_6$H$_3$(Br)-OCH$_2$CH=CBr$_2$  (VII)-4

TABLE 2-continued (R$^1$)$_l$-C$_6$H$_4$-O-C$_6$H$_2$(Cl)(Cl)-OCH$_2$CH=CCl$_2$  (VII)-5

(R$^1$)$_l$-C$_6$H$_4$-O-C$_6$H$_2$(Cl)(Cl)-OCH$_2$CH=CBr$_2$  (VII)-6

(R$^1$)$_l$-C$_6$H$_4$-O-C$_6$H$_2$(Cl)(Br)-OCH$_2$CH=CCl$_2$  (VII)-7

(R$^1$)$_l$-C$_6$H$_4$-O-C$_6$H$_2$(Cl)(Br)-OCH$_2$CH=CBr$_2$  (VII)-8

(R$^1$)$_l$-C$_6$H$_4$-O-C$_6$H$_2$(Cl)(Cl)-OCH$_2$CH=CCl$_2$  (VII)-9

(R$^1$)$_l$-C$_6$H$_4$-O-C$_6$H$_2$(Cl)(Cl)-OCH$_2$CH=CBr$_2$  (VII)-10

(R$^1$)$_l$-C$_6$H$_4$-O-C$_6$H$_2$(Cl)(Cl)-OCH$_2$CH=CCl$_2$  (VII)-11

(R$^1$)$_l$-C$_6$H$_4$-O-C$_6$H$_2$(Cl)(Cl)-OCH$_2$CH=CBr$_2$  (VII)-12

(R$^1$)$_l$-C$_6$H$_4$-O-C$_6$H$_2$(Cl)(Cl)-OCH$_2$CH=CCl$_2$  (VII)-13

TABLE 2-continued

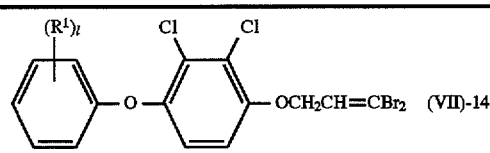

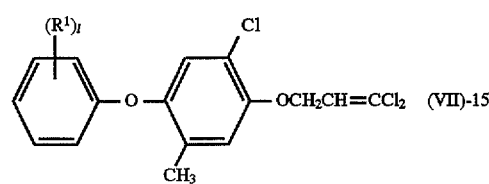

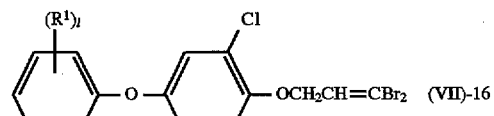

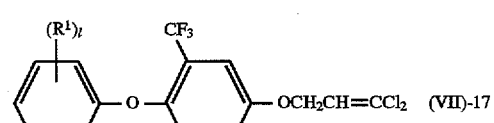

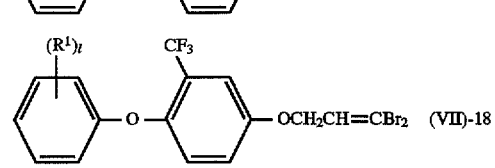

| $(R^1)_l$ | $(R^1)_l$ |
|---|---|
| 4-Cl | 2,4-$F_2$ |
| 3-Br | 4-F |
| 3,5-$Cl_2$ | 3-Cl |
| 3,5-$F_2$ | 3-F |
| 3,4-$Cl_2$ | 4-Br |
| 2,4-$Cl_2$ | 3,5-$Br_2$ |
| 3-I | 2-Cl, 4-$OC_2H_5$ |
| 4-I | 2-Cl, 4-$OCH(CH_3)_2$ |
| 3-$C(CH_3)_3$ | 3,5-$(OC_2H_5)_2$ |
| 4-$C(CH_3)_3$ | 3,5-$(OCH(CH_3)_2)_2$ |
| 3-$CF_3$ | 3-$CH_3$, 5-$OCH(CH_3)_2$ |
| 4-$CF_3$ | 3-$OCF_3$ |
| 3,5-$(CF_3)_2$ | 4-$OCF_3$ |
| 2,4-$(CF_3)_2$ | 3-$OCH_2CF_3$ |
| 2-Cl, 4-$CF_3$ | 4-$OCH_2CF_3$ |
| 2,6-$Cl_2$, 4-$CF_3$ | 3-$SCH_2CF_3$ |
| 2-Br, 4-$CF_3$ | 4-$SCH_2CF_3$ |
| 2-F, 6-Cl, 4-$CF_3$ | 3-Br, 4-$OCH_2CH=C(Br)_2$ |
| 2,6-$F_2$, 4-$CF_3$ | 3-Br, 4-$OCH_2CH=C(Cl)_2$ |
| 3-$OCH_3$ | 3-$CH_3$ |
| 4-$OCH_3$ | 4-$CH_3$ |
| 3-$OC_2H_5$ | 3-cyclopentyl |
| 4-$OC_2H_5$ | 4-cyclopentyl |
| 3-$OCH(CH_3)_2$ | 3-cyclohexyl |
| 4-$OCH(CH_3)_2$ | 4-cyclohexyl |
| 3-$OC(CH_3)_3$ | 3-phenyl |
| 4-$OC(CH_3)_3$ | 4-phenyl |
| 3,5-$(OCH_3)_2$ | 3-O-cyclopentyl |
| 3,4-$(OCH_3)_2$ | 4-O-cyclopentyl |
| 2-Cl, 4-$OCH_3$ | 3-O-cyclohexyl |
| 4-O-cyclohexyl | 2-Br, 4-$OC_2H_5$ |
| 3-phenoxy | 2-Br, 4-$OCH(CH_3)_2$ |
| 4-phenoxy | 2-Cl, 4-$OCF_3$ |
| 2-Br, 4-$OCH_3$ | 2-Br, 4-$OCF_3$ |
| 2,4-$(NO_2)_2$ | |
| 4-CN | |
| 2,6-$Cl_2$, 4-$CF_3$ | |

TABLE 2-continued

2-F, 6-Cl, 4-$CF_3$
2,6-$F_2$, 4-$CF_3$
2-F, 4-$NO_2$
2-Cl, 4-$NO_2$
2-$NO_2$, 4-$CF_3$
2,4-$(NO_2)_2$, 6-$CF_3$
2-$CF_3$, 4-$NO_2$
4-$NHCOCH_3$
4-$NHCOCF_3$
4-(3-chloro-5-trifluoromethyl-2-pyridyloxy)

The compounds of the following formulae VIII-1 to 16 are shown in the Table 3.

TABLE 3

[Structures VIII-1 through VIII-8 with $(R^1)_l$ on left phenyl ring connected via O to right phenyl ring with substituents]

VIII-1: 2-$C_2H_5$, 4-$OCH_2CH=CCl_2$
VIII-2: 2-$C_2H_5$, 4-$OCH_2CH=CBr_2$
VIII-3: 2-$CH_2CH=CH_2$, 4-$OCH_2CH=CCl_2$
VIII-4: 2-$CH_2CH=CH_2$, 4-$OCH_2CH=CBr_2$
VIII-5: 2-$C(CH_3)_3$, 4-$OCH_2CH=CCl_2$
VIII-6: 2-$C(CH_3)_3$, 4-$OCH_2CH=CBr_2$
VIII-7: 2-$CH(CH_3)CH_2CH_3$, 4-$OCH_2CH=CCl_2$
VIII-8: 2-$CH(CH_3)CH_2CH_3$, 4-$OCH_2CH=CBr_2$

TABLE 3-continued (VIII)-9: Ar(R¹)ₗ–O–Ar[CH₂CH(CH₃)₂]–OCH₂CH=CCl₂

(VIII)-10: Ar(R¹)ₗ–O–Ar[CH₂CH(CH₃)₂]–OCH₂CH=CBr₂

(VIII)-11: Ar(R¹)ₗ–O–Ar[CH=NOCH₃]–OCH₂CH=CCl₂

(VIII)-12: Ar(R¹)ₗ–O–Ar[CH=NOCH₃]–OCH₂CH=CBr₂

(VIII)-13: Ar(R¹)ₗ–O–Ar[CHF₂]–OCH₂CH=CCl₂

(VIII)-14: Ar(R¹)ₗ–O–Ar[CHF₂]–OCH₂CH=CBr₂

(VIII)-15: Ar(R¹)ₗ–O–Ar[Cl]–OCH₂CH=CCl₂

(VIII)-16: Ar(R¹)ₗ–O–Ar[Cl]–OCH₂CH=CBr₂

| $(R^1)_l$ | $(R^1)_l$ |
|---|---|
| 3-Cl | 4-OCH(CH₃)₂ |
| 4-Cl | 2-Cl, 4-OCH₃ |
| 3-Br | 2-Cl, 4-OC₂H₅ |
| 4-Br | 2-Cl, 4-OCH₂CH₂CH₃ |
| 3-C(CH₃)₃ | 2-Cl, 4-OCH(CH₃)₂ |
| 4-C(CH₃)₃ | 3,4-(OCH₃)₂ |
| 2-Cl, 4-C(CH₃)₃ | 3,5-(OCH₃)₂ |
| 2-Br, 4-C(CH₃)₃ | 3-OCF₃ |
| 3-CF₃ | 4-OCF₃ |
| 4-CF₃ | 3-OCH₂CF₃ |
| 3,5-(CH₃)₂ | 4-OCH₂CF₃ |
| 2,4-(CH₃)₂ | 2-Cl, 4-OCF₃ |
| 2-F, 4-CF₃ | 2-Cl, 4-OCH₂CF₃ |
| 2-Cl, 4-CF₃ | 3-SCH₂CF₃ |
| 2,6-Cl₂, 4-CF₃ | 4-SCH₂CF₃ |
| 2-F, 6-Cl, 4-CF₃ | 4-OCH₂CH=CH(Cl) |
| 2,6-F₂, 4-CF₃ | 4-CH₂(OH)CH₂CH₃ |
| 3-OCH₃ | 3-cyclopentyl |
| 4-OCH₃ | 3-O-cyclopentyl |
| 3-OC₂H₅ | 4-O-cyclopentyl |
| 4-OC₂H₅ | 4-O-cyclopentyl |
| 3-OCH₂CH₂CH₃ | 3-cyclohexyl |
| 4-OCH₂CH₂CH₃ | 3-O-cyclohexyl |
| 3-OCH(CH₃)₂ | 4-cyclohexyl |
| 4-O-cyclohexyl | 3-phenoxy |
| 3-phenyl | 4-phenoxy |
| 4-phenyl | |

The compounds of the following formulae IX-1 to 54 are shown in Table 4.

TABLE 4

(IX)-1: Ar(R¹)ₗ–O–Ar[C₂H₅]–OCH₂CH=CCl₂

(IX)-2: Ar(R¹)ₗ–O–Ar[C₂H₅]–OCH₂CH=CBr₂

(IX)-3: Ar(R¹)ₗ–O–Ar[CH₃]–OCH₂CH=CCl₂

(IX)-4: Ar(R¹)ₗ–O–Ar[CH₃]–OCH₂CH=CBr₂

(IX)-5: Ar(R¹)ₗ–O–Ar[CH₃]–OCH₂CH=CCl₂

(IX)-6: Ar(R¹)ₗ–O–Ar[CH₃]–OCH₂CH=CBr₂

(IX)-7: Ar(R¹)ₗ–O–Ar[CH(CH₃)₂]–OCH₂CH=CCl₂

(IX)-8: Ar(R¹)ₗ–O–Ar[CH(CH₃)₂]–OCH₂CH=CBr₂

(IX)-9: Ar(R¹)ₗ–O–Ar[CH₂CH₂CH₂CH₃]–OCH₂CH=CCl₂

TABLE 4-continued
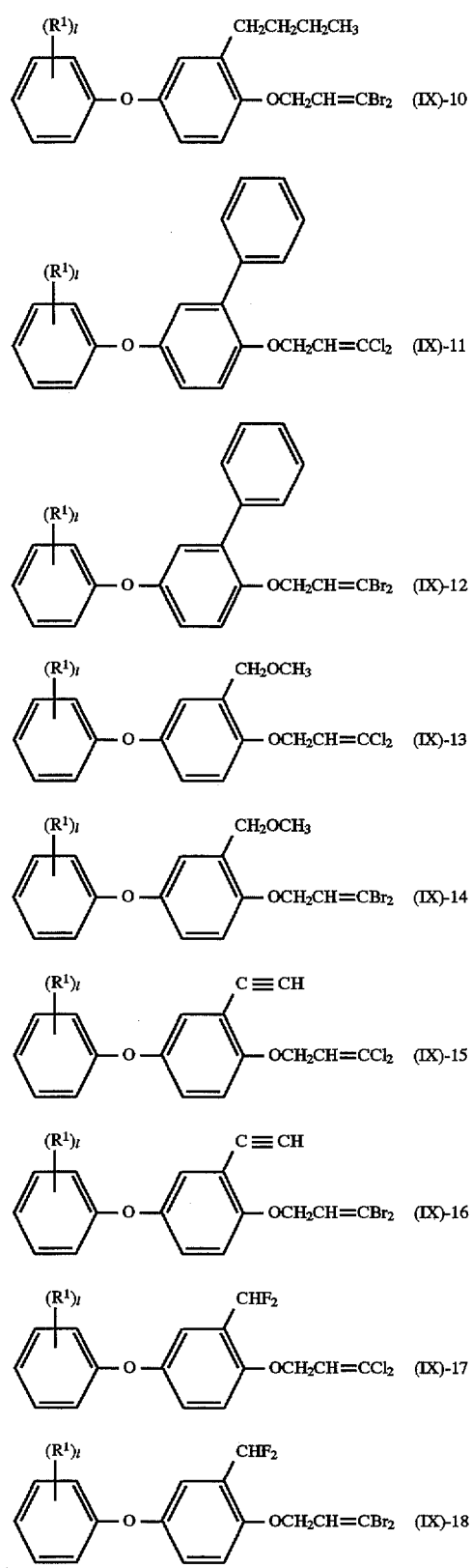
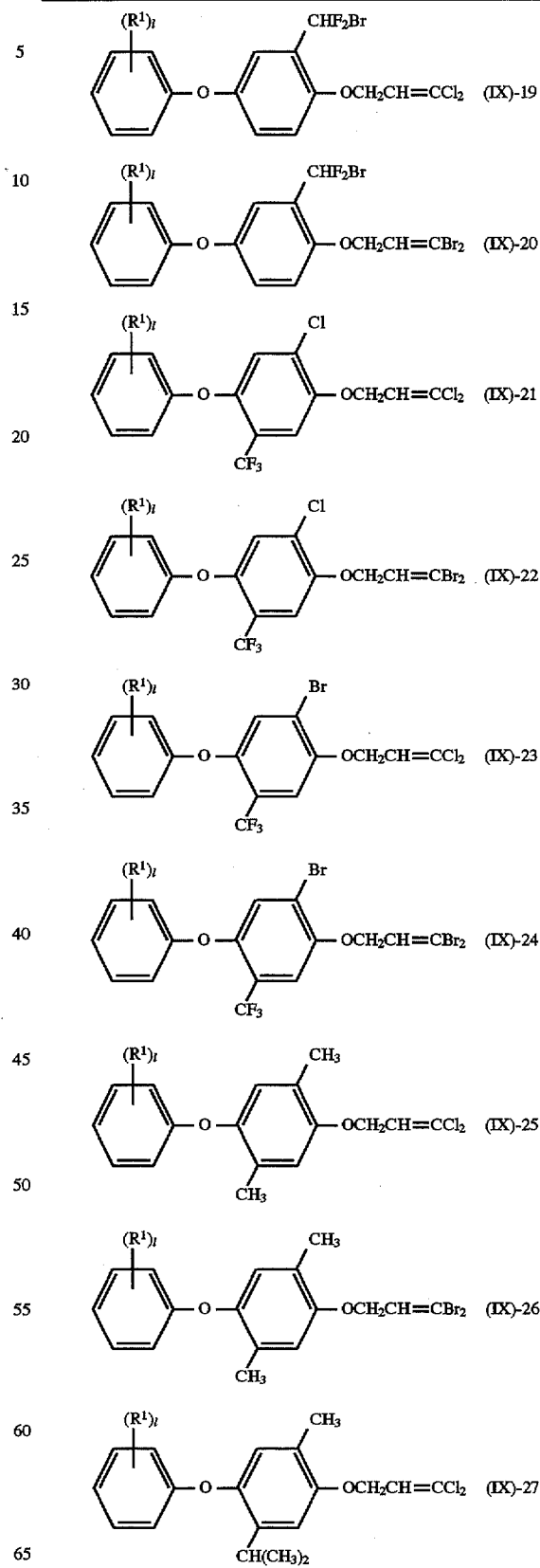

TABLE 4-continued

| Structure | Label |
|---|---|
| Ar-O-Ar' with CH₃ (top), CH(CH₃)₂ (bottom), OCH₂CH=CBr₂ | (IX)-28 |
| Ar-O-Ar' with OCF₃, OCH₂CH=CCl₂ | (IX)-29 |
| Ar-O-Ar' with OCF₃, OCH₂CH=CBr₂ | (IX)-30 |
| Ar-O-Ar' with OCHF₂, OCH₂CH=CCl₂ | (IX)-31 |
| Ar-O-Ar' with OCHF₂, OCH₂CH=CBr₂ | (IX)-32 |
| Ar-O-Ar' with OCF₂Br, OCH₂CH=CCl₂ | (IX)-33 |
| Ar-O-Ar' with OCF₂Br, OCH₂CH=CBr₂ | (IX)-34 |
| Ar-O-Ar' with OCF₂CF₃, OCH₂CH=CCl₂ | (IX)-35 |
| Ar-O-Ar' with OCF₂CF₃, OCH₂CH=CBr₂ | (IX)-36 |
| Ar-O-Ar' with OCF₂CF₂H, OCH₂CH=CCl₂ | (IX)-37 |
| Ar-O-Ar' with OCF₂CF₂H, OCH₂CH=CBr₂ | (IX)-38 |
| Ar-O-Ar' with OCF₂CFHCF₃, OCH₂CH=CCl₂ | (IX)-39 |
| Ar-O-Ar' with OCF₂CFHCF₃, OCH₂CH=CBr₂ | (IX)-40 |
| Ar-O-Ar' with CH=NOCH₂CH=CH₂, OCH₂CH=CCl₂ | (IX)-41 |
| Ar-O-Ar' with CH=NOCH₂CH=CH₂, OCH₂CH=CBr₂ | (IX)-42 |
| Ar-O-Ar' with OCH₃, OCH₂CH=CCl₂ | (IX)-43 |
| Ar-O-Ar' with OCH₃, OCH₂CH=CBr₂ | (IX)-44 |
| Ar-O-Ar' with OCH₂CH₃, OCH₂CH=CCl₂ | (IX)-45 |
| Ar-O-Ar' with OCH₂CH₃, OCH₂CH=CBr₂ | (IX)-46 |
| Ar-O-Ar' with OCH₂CH₂CH₃, OCH₂CH=CCl₂ | (IX)-47 |
| Ar-O-Ar' with OCH₂CH₂CH₃, OCH₂CH=CBr₂ | (IX)-48 |
| Ar-O-Ar' with OCH(CH₃)₂, OCH₂CH=CCl₂ | (IX)-49 |

TABLE 4-continued (IX)-50: phenyl(R¹)ₗ—O—[phenyl with OCH(CH₃)₂ and OCH₂CH=CBr₂]

(IX)-51: phenyl(R¹)ₗ—O—[phenyl with OCH₂CH₃ and OCH₂CH=CCl₂]

(IX)-52: phenyl(R¹)ₗ—O—[phenyl with OCH₂CH₃ and OCH₂CH=CBr₂]

(IX)-53: phenyl(R¹)ₗ—O—[phenyl with CH(CH₃)CH=CH₂ and OCH₂CH=CCl₂]

(IX)-54: phenyl(R¹)ₗ—O—[phenyl with CH(CH₃)CH=CH₂ and OCH₂CH=CBr₂]

| (R¹)ₗ | (R¹)ₗ |
|---|---|
| 3-C(CH₃)₃ | 2-Cl, 4-OCH(CH₃)₂ |
| 4-C(CH₃)₃ | 3-OCF₃ |
| 3-CF₃ | 4-OCF₃ |
| 4-CF₃ | 2-Cl, 4-OCF₃ |
| 2-F, 4-CF₃ | 3-cyclopentyl |
| 2-Cl, 4-CF₃ | 4-cyclopentyl |
| 2-F, 6-Cl, 4-CF₃ | 3-cyclohexyl |
| 2,6-F₂, 4-CF₃ | 4-cyclohexyl |
| 2,6-Cl₂, 4-CF₃ | 3-phenyl |
| 3-OCH₃ | 4-phenyl |
| 3-OC₂H₅ | 3-phenoxy |
| 3-OCH(CH₃)₂ | 4-phenoxy |
| 4-OCH₃ | 3-O-cyclopentyl |
| 4-OC₂H₅ | 3-O-cyclohexyl |
| 4-OCH(CH₃)₂ | 4-O-cyclohexyl |
| 2-Cl, 4-OCH₃ | 4-O-cyclopentyl |
| 2-Cl, 4-OC₂H₅ | 4-Cl |
| 2-CH₃, 3,4-ethylenedioxy | |
| 4-OCH₂CF₃ | |
| 4-NO₂ | |

The compounds of the formulae X-1 to 60 are shown in Table 5.

TABLE 5

(X)-1: phenyl(R¹)ₗ—O—[phenyl with Cl, CHF₂ and OCH₂CH=CCl₂]

(X)-2: phenyl(R¹)ₗ—O—[phenyl with Cl, CHF₂ and OCH₂CH=CBr₂]

(X)-3: phenyl(R¹)ₗ—O—[phenyl with Cl, CH₃ and OCH₂CH=CCl₂]

(X)-4: phenyl(R¹)ₗ—O—[phenyl with Cl, CH₃ and OCH₂CH=CBr₂]

(X)-5: phenyl(R¹)ₗ—O—[phenyl with Br, CHF₂ and OCH₂CH=CCl₂]

(X)-6: phenyl(R¹)ₗ—O—[phenyl with Br, CHF₂ and OCH₂CH=CBr₂]

(X)-7: phenyl(R¹)ₗ—O—[phenyl with Br, CH₃ and OCH₂CH=CCl₂]

(X)-8: phenyl(R¹)ₗ—O—[phenyl with Br, CH₃ and OCH₂CH=CBr₂]

(X)-9: phenyl(R¹)ₗ—O—[phenyl with Cl, C₂H₅ and OCH₂CH=CCl₂]

(X)-10: phenyl(R¹)ₗ—O—[phenyl with Cl, C₂H₅ and OCH₂CH=CBr₂]

TABLE 5-continued
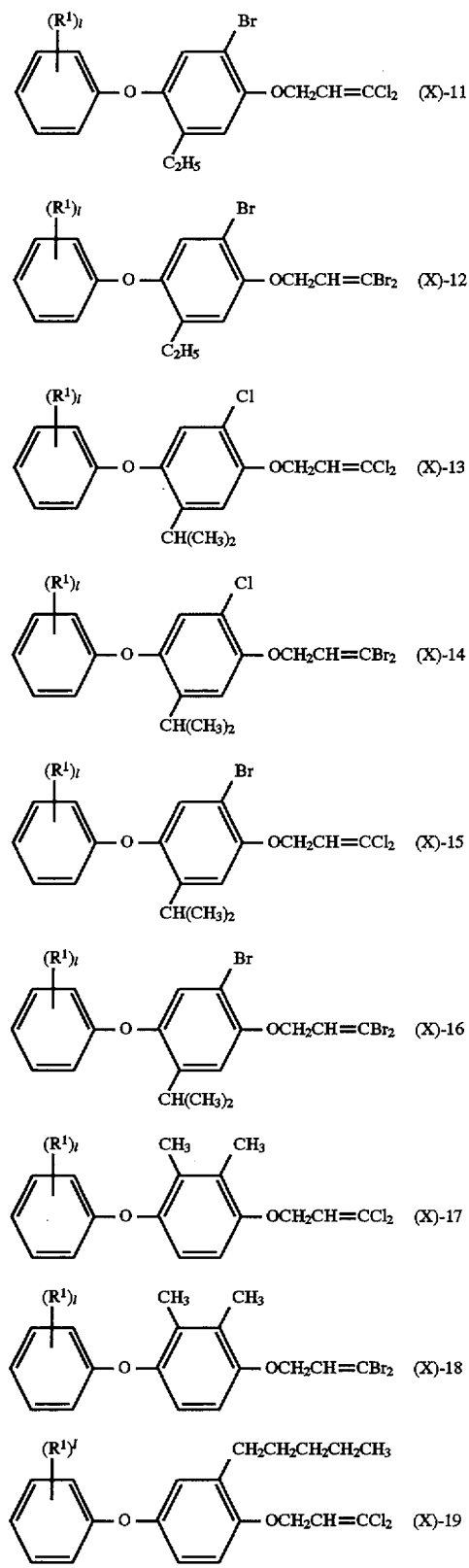
TABLE 5-continued
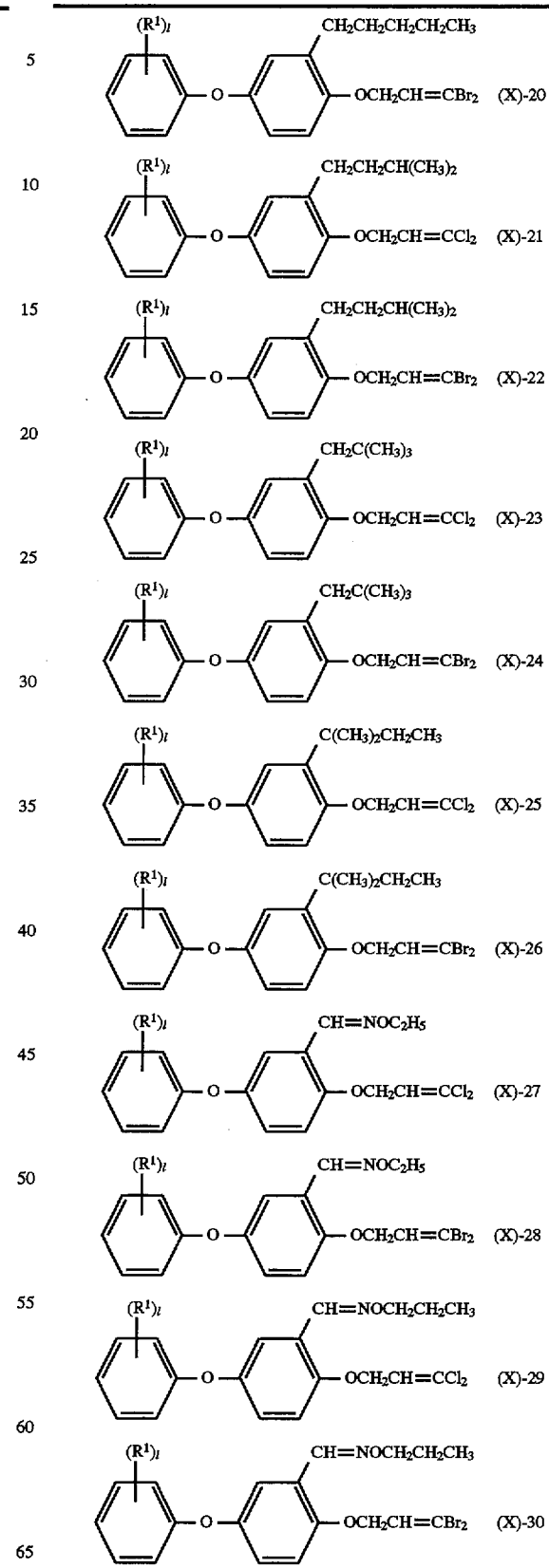

TABLE 5-continued
 (X)-31
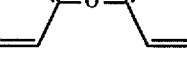 (X)-32
 (X)-33
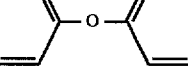 (X)-34
 (X)-35
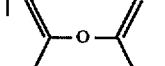 (X)-36
 (X)-37
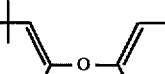 (X)-38
 (X)-39
 (X)-40
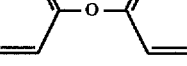 (X)-41
TABLE 5-continued
(X)-42
(X)-43
(X)-44
(X)-45
(X)-46
(X)-47
(X)-48
(X)-49
(X)-50
(X)-51
(X)-52

TABLE 5-continued

| | |
|---|---|
| (X)-53 | phenyl-O-phenyl(CH₂O(CH₂)₂CH₃)-OCH₂CH=CCl₂ |
| (X)-54 | phenyl-O-phenyl(CH₂O(CH₂)₂CH₃)-OCH₂CH=CBr₂ |
| (X)-55 | phenyl-O-phenyl(CH₂OCH(CH₃)₂)-OCH₂CH=CCl₂ |
| (X)-56 | phenyl-O-phenyl(CH₂OCH(CH₃)₂)-OCH₂CH=CBr₂ |
| (X)-57 | phenyl-O-phenyl(F)-OCH₂CH=CCl₂ |
| (X)-58 | phenyl-O-phenyl(F)-OCH₂CH=CBr₂ |
| (X)-59 | phenyl-O-phenyl(C(CH₃)₃)-OCH₂CH=CCl₂ |
| (X)-60 | phenyl-O-phenyl(C(CH₃)₃)-OCH₂CH=CBr₂ |

| (R¹)ₗ | (R¹)ₗ |
|---|---|
| 3-cyclohexyl | 3-OC₂H₅ |
| 4-cyclohexyl | 4-OC₂H₅ |
| 3-OCH(CH₃)₂ | 3-phenyl |
| 4-OCH(CH₃)₂ | 4-phenyl |

The compounds of the formulae XI-1 to 2 are shown in Table 6.

TABLE 6

(XI)-1: (R¹)ₗ-phenyl-O-phenyl(R²)ₘ-OCH₂CH=CCl₂ (positions 1,2,3,4,5,6 indicated)

TABLE 6-continued (XI)-2: (R¹)ₗ-phenyl-O-phenyl(R²)ₘ-OCH₂CH=CBr₂

| (R¹)ₗ | (R²)ₘ |
|---|---|
| 4-OC₂H₅ | 2-(CH₂)₂CH₃, 5-CH(CH₃)₂ |
| 4-Cl | 2,6-(CH₃)₂ |
| 3-Cl | 2,6-(CH(CH₃)₂)₂ |
| 3-Cl | 2-CHF₂ |
| 4-OCH(CH₃)₂ | 2-Br, 6-NO₂ |
| 4-OCH(CH₃)₂ | 2-I |
| 4-OCH(CH₃)₂ | 2-F |

The position of R² is numbered as shown in the formula XI-1.

The compounds of the formulae XII-1 to 4 are shown in Table 7.

TABLE 7

| | |
|---|---|
| (XII)-1 | (R¹)ₗ-phenyl-O-indane-OCH₂CH=CCl₂ |
| (XII)-2 | (R¹)ₗ-phenyl-O-indane-OCH₂CH=CBr₂ |
| (XII)-3 | (R¹)ₗ-phenyl-O-tetrahydronaphthalene-OCH₂CH=CCl₂ |
| (XII)-4 | (R¹)ₗ-phenyl-O-tetrahydronaphthalene-OCH₂CH=CBr₂ |

| (R¹)ₗ | (R¹)ₗ |
|---|---|
| 3-Cl | 4-CF₃ |
| 4-Cl | 4-SCH₂CF₃ |
| 3-Br | 3-SCH₂CF₃ |
| 4-Br | 3-phenyl |
| 3-CF₃ | 4-phenyl |
| 3-cyclopentyl | 4-OCH₂CF₃ |
| 4-cyclopentyl | 3-cyclohexyl |
| 2-Cl, 4-CF₃ | 4-cyclohexyl |
| 3-C(CH₃)₃ | 3-phenoxy |
| 4-C(CH₃)₃ | 4-phenoxy |
| 3-OCH₃ | 3-O-cyclopentyl |
| 4-OCH₃ | 4-O-cyclopentyl |
| 3-OC₂H₅ | 3-O-cyclohexyl |
| 4-OC₂H₅ | 4-O-cyclohexyl |

TABLE 7-continued

| | |
|---|---|
| 3-OCH(CH₃)₂ | 3-Cl, 5-CF₃ |
| 4-OCH(CH₃)₂ | 3-Br, 5-CF₃ |
| 3-OCF₃ | 3,5-(CF₃)₂ |
| 4-OCF₃ | 3,5-(CF₃)₂, 6-Cl |
| 3-OCH₂CF₃ | |
| 2-Cl, 4-CF₃ | |
| 5-CF₃ | |

The compounds of the formulae XIII-1 to 16 are shown in Table 8.

TABLE 8

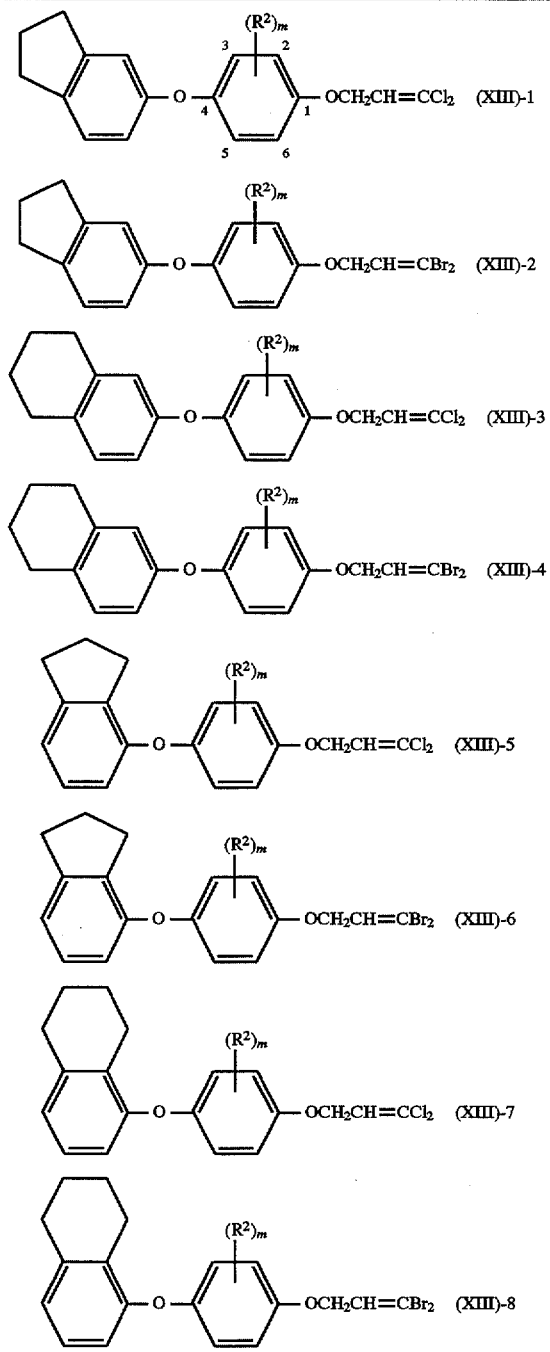

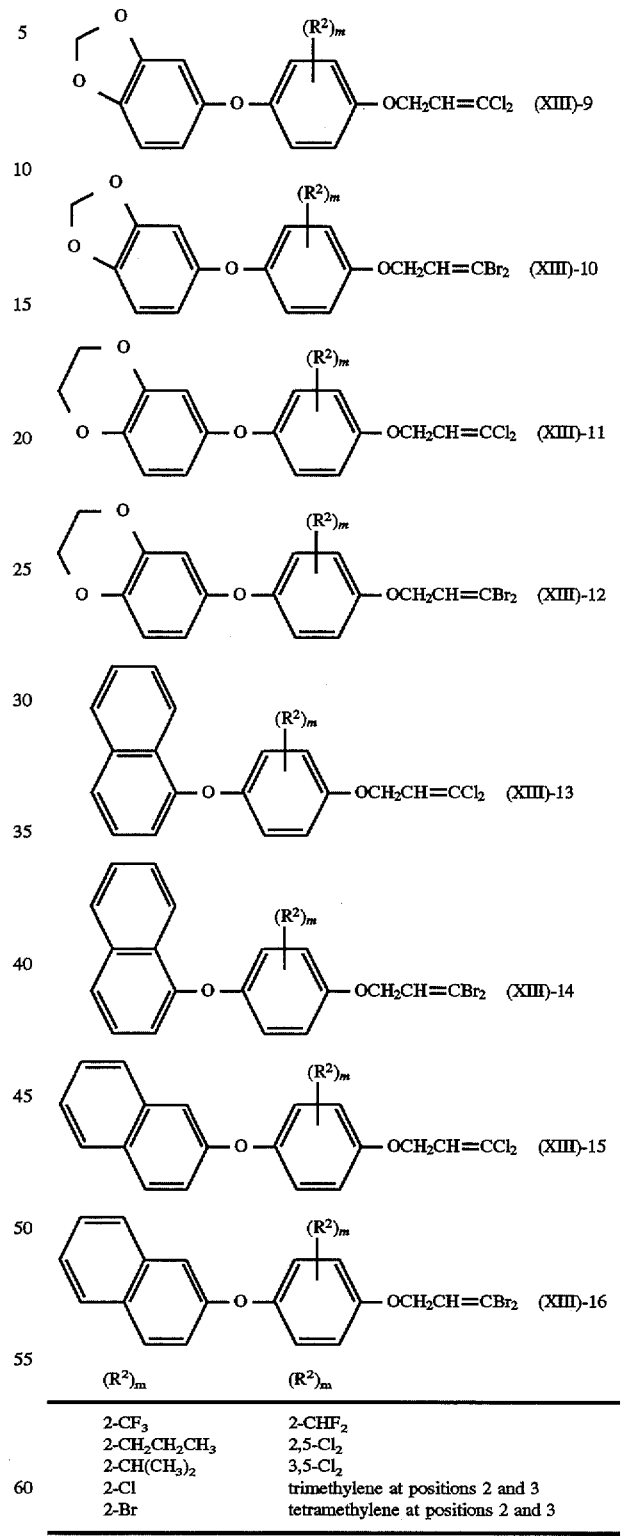

| $(R^2)_m$ | $(R^2)_m$ |
|---|---|
| 2-CF₃ | 2-CHF₂ |
| 2-CH₂CH₂CH₃ | 2,5-Cl₂ |
| 2-CH(CH₃)₂ | 3,5-Cl₂ |
| 2-Cl | trimethylene at positions 2 and 3 |
| 2-Br | tetramethylene at positions 2 and 3 |

The position of $R^2$ is numbered as shown in the formula XIII-1

The compounds of the formulae XIV-1 to 16 are shown in Table 9.

TABLE 9
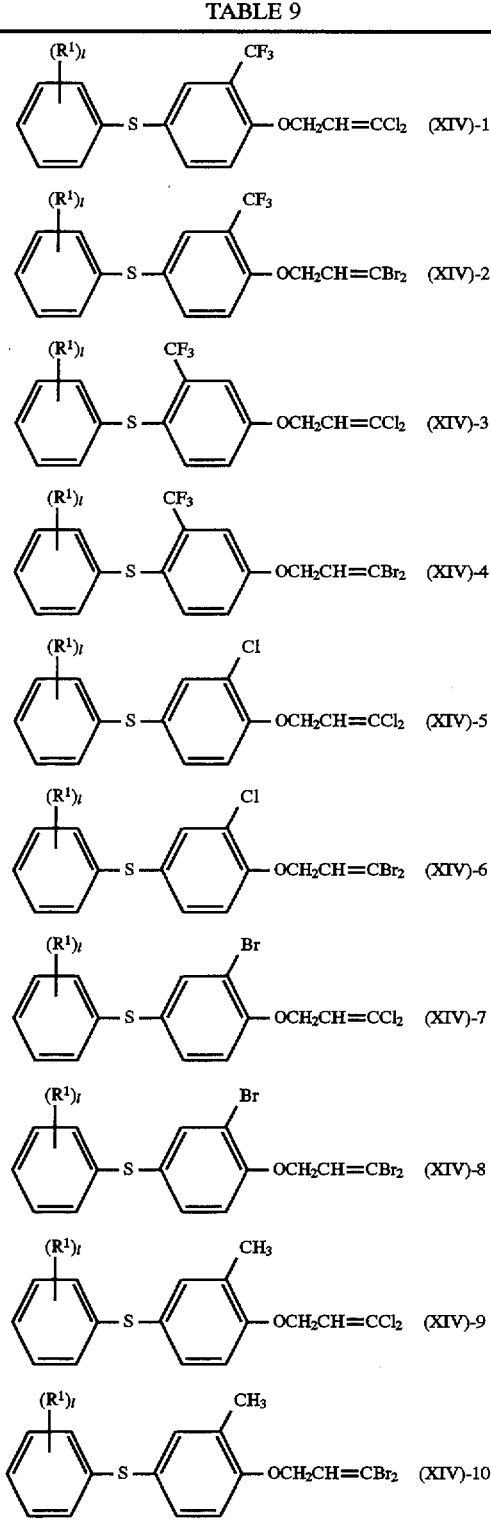
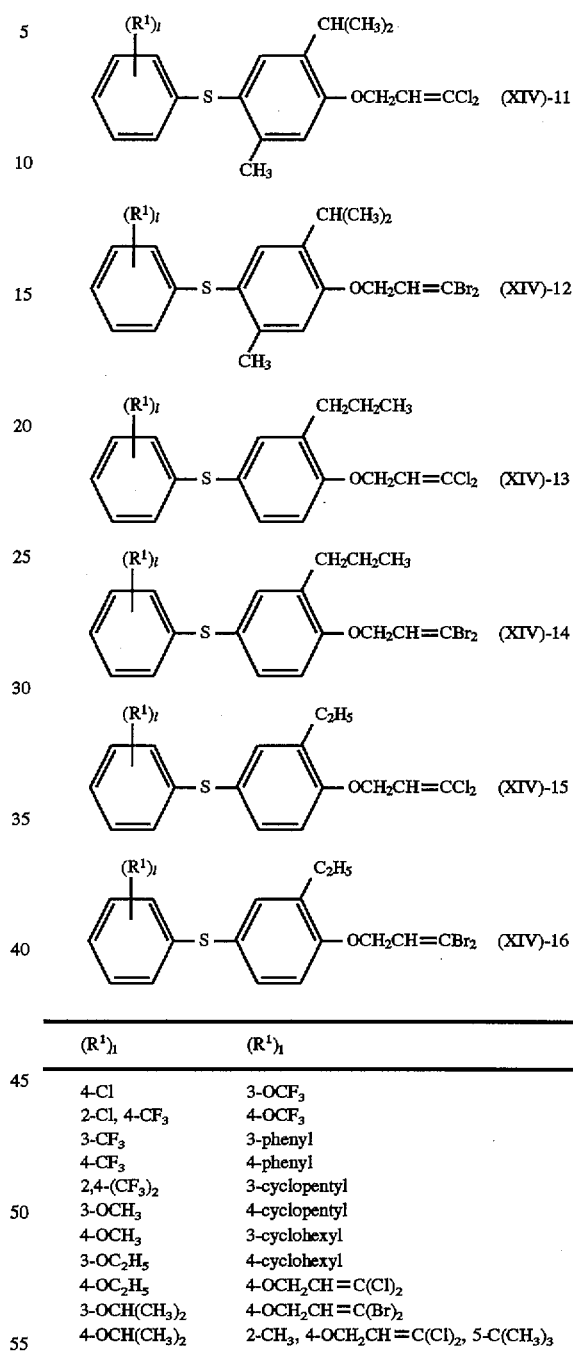
| $(R^1)_l$ | $(R^1)_l$ |
|---|---|
| 4-Cl | 3-OCF$_3$ |
| 2-Cl, 4-CF$_3$ | 4-OCF$_3$ |
| 3-CF$_3$ | 3-phenyl |
| 4-CF$_3$ | 4-phenyl |
| 2,4-(CF$_3$)$_2$ | 3-cyclopentyl |
| 3-OCH$_3$ | 4-cyclopentyl |
| 4-OCH$_3$ | 3-cyclohexyl |
| 3-OC$_2$H$_5$ | 4-cyclohexyl |
| 4-OC$_2$H$_5$ | 4-OCH$_2$CH=C(Cl)$_2$ |
| 3-OCH(CH$_3$)$_2$ | 4-OCH$_2$CH=C(Br)$_2$ |
| 4-OCH(CH$_3$)$_2$ | 2-CH$_3$, 4-OCH$_2$CH=C(Cl)$_2$, 5-C(CH$_3$)$_3$ |
The compounds of the formulae XV-1 to 20 are shown in Table 10.

TABLE 10
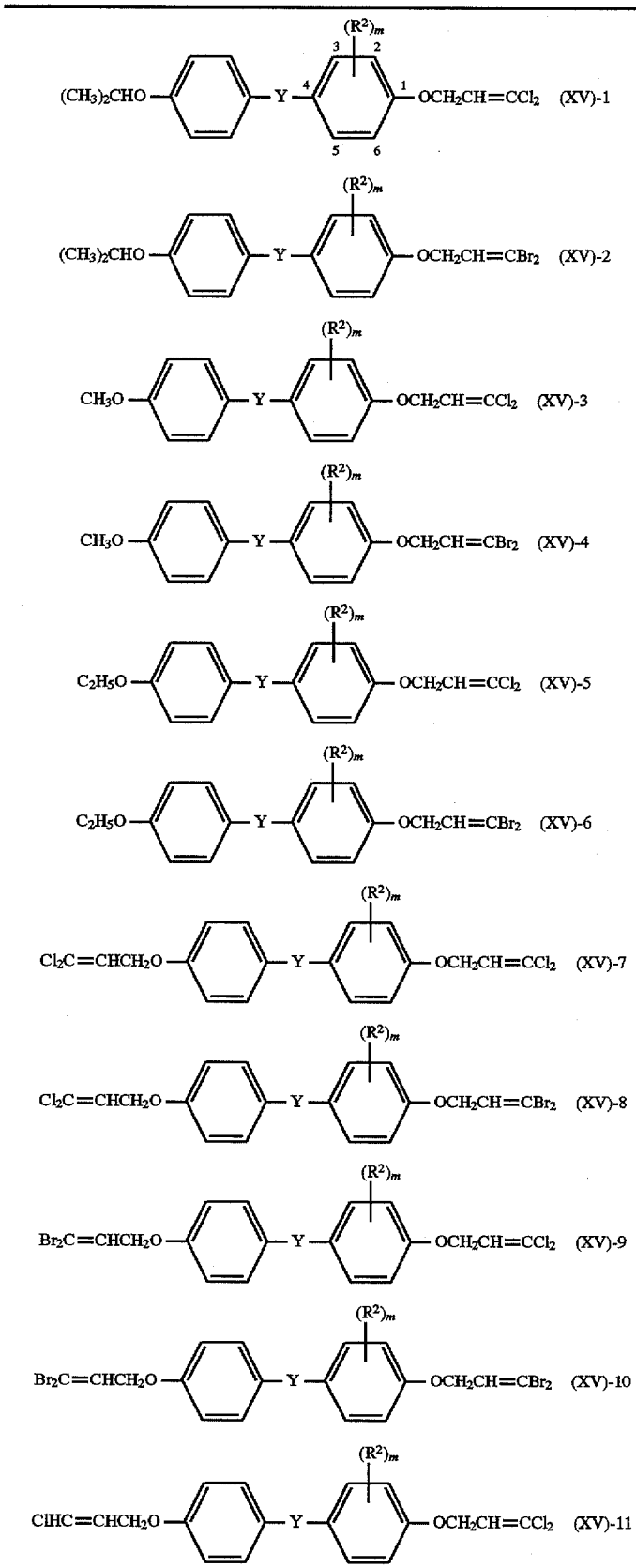

TABLE 10-continued
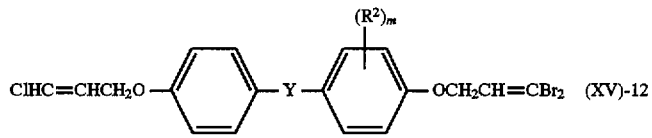 (XV)-12
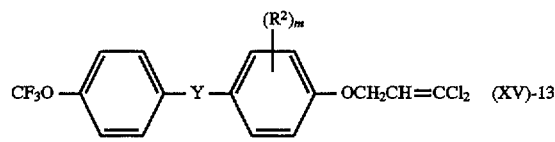 (XV)-13
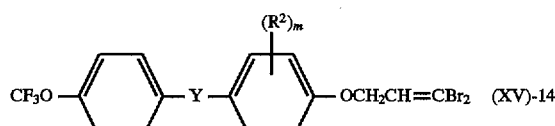 (XV)-14
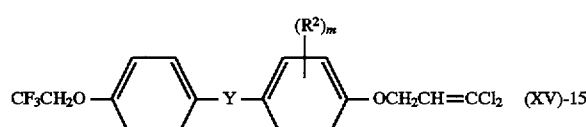 (XV)-15
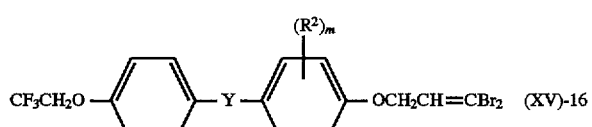 (XV)-16
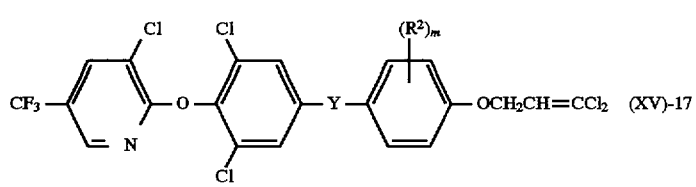 (XV)-17
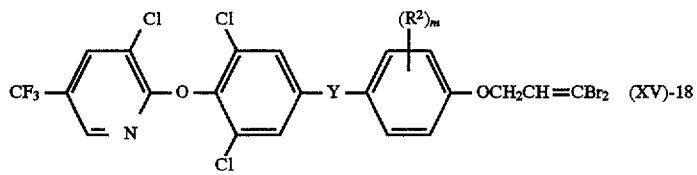 (XV)-18
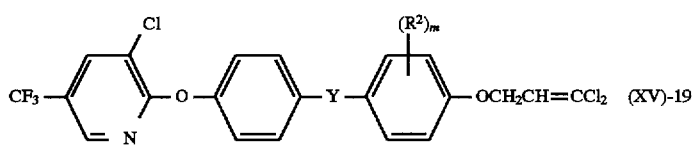 (XV)-19
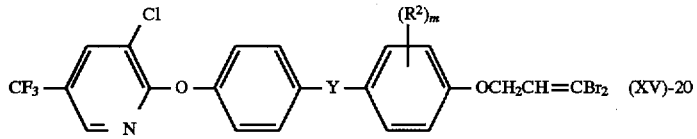 (XV)-20
| Y | $(R^2)_m$ |
|---|---|
| $CH_2$ | 2-Cl |
| $CH_2$ | 2-Br |
| $CH_2$ | 2-$CH_3$ |
| $CH(CH_3)$ | 2-Cl |
| $CH(CH_3)$ | 2-Br |
| $CH(CH_3)$ | 2-$CH_3$ |
| $C(CH_3)_2$ | 2-Cl |
| $C(CH_3)_2$ | 2-Br |

TABLE 10-continued

| | |
|---|---|
| C(CH₃)₂ | 2-CH₃ |
| CH(C₂H₅) | 2-Cl |
| CH(C₂H₅) | 2-Br |
| CH(C₂H₅) | 2-CH₃ |
| C(C₂H₅)₂ | 2-Cl |
| C(C₂H₅)₂ | 2-Br |
| C(C₂H₅)₂ | 2-CH₃ |
| C(CH₃)(C₂H₅) | 2-Cl |
| C(CH₃)(C₂H₅) | 2-Br |
| C(CH₃)(C₂H₅) | 2-CH₃ |
| C(CF₃)(CF₃) | 2-Cl |
| C(CF₃)(CF₃) | 2-Br |
| C(CF₃)(CF₃) | 2-CH₃ |
| C(CF₃)(CF₃) | 2,6-Br₂ |
| C=CH₂ | 2-Cl |
| C=CH₂ | 2-Br |
| C=CH₂ | 2-CH₃ |
| C(CH₃)₂ | 2,5-Cl₂ |
| C(CH₃)₂ | 2-Br |
| CH(CH(CH₃)₂) | 2-Br |

The position of $R^2$ is numbered as shown in the formula XV-1

The compounds of the formulae XVI-1 to 8 are shown in Table 11.

TABLE 11

(XVI)-1: phenyl(R¹)ₗ—O—[CF₃-substituted phenyl]—S—CH₂CH=CCl₂

(XVI)-2: phenyl(R¹)ₗ—O—[CF₃-substituted phenyl]—S—CH₂CH=CBr₂

(XVI)-3: phenyl(R¹)ₗ—O—[CH₂CH₂CH₃-substituted phenyl]—S—CH₂CH=CCl₂

(XVI)-4: phenyl(R¹)ₗ—O—[CH₂CH₂CH₃-substituted phenyl]—S—CH₂CH=CBr₂

(XVI)-5: phenyl(R¹)ₗ—O—[CF₃-substituted phenyl]—NH—CH₂CH=CCl₂

(XVI)-6: phenyl(R¹)ₗ—O—[CF₃-substituted phenyl]—NH—CH₂CH=CBr₂

(XVI)-7: phenyl(R¹)ₗ—O—[CH₂CH₂CH₃-substituted phenyl]—NH—CH₂CH=CCl₂

(XVI)-8: phenyl(R¹)ₗ—O—[CH₂CH₂CH₃-substituted phenyl]—NH—CH₂CH=CBr₂

| $(R^1)_1$ | $(R^1)_1$ |
|---|---|
| 3-C(CH₃)₃ | 4-cyclopentyl |
| 4-C(CH₃)₃ | 3-phenyl |
| 3-OC₂H₅ | 3-cyclopentyl |
| 4-OC₂H₅ | 4-cyclohexyl |
| 3-OCH(CH₃)₂ | 4-OCF₃ |
| 4-OCH(CH₃)₂ | 4-phenyl |
| 3-cyclohexyl | 3-OCF₃ |

The compounds of the formulae XVII-1 to 4 are shown in Table 12.

TABLE 12

(XVII)-1: phenyl(R¹)ₗ—Y—[Br-substituted phenyl]—S—CH₂CH=CCl₂

(XVII)-2: phenyl(R¹)ₗ—Y—[Br-substituted phenyl]—S—CH₂CH=CBr₂

(XVII)-3: phenyl(R¹)ₗ—Y—[Cl-substituted phenyl]—S—CH₂CH=CCl₂

TABLE 12-continued

[Structure: (R¹)ₗ-phenyl-Y-phenyl(Cl)-S-CH₂CH=CBr₂]  (XVII)-4

| (R¹)ₗ | Y |
|---|---|
| 4-OCH(CH₃)₂ | C(CH₃)₂ |
| 3-OCH(CH₃)₂ | C(CH₃)₂ |
| 4-OC₂H₅ | C(CH₃)₂ |
| 3-OC₂H₅ | C(CH₃)₂ |
| 4-OCH(CH₃)₂ | CH(CH₃) |
| 3-OCH(CH₃)₂ | CH(CH₃) |
| 4-OC₂H₅ | CH(CH₃) |
| 3-OC₂H₅ | CH(CH₃) |

The compounds of the formulae XVIII-1 to 36 are shown in Table 13.

TABLE 13

Pyridine (with (R¹)ₗ, positions 2,3,4,5,6,N labeled)—O—phenyl(2,6-diCl)—OCH₂CH=CCl₂   (XVIII)-1

Pyridine((R¹)ₗ)—O—phenyl(2,6-diCl)—OCH₂CH=CBr₂   (XVIII)-2

Pyridine((R¹)ₗ)—O—phenyl(2,6-diBr)—OCH₂CH=CCl₂   (XVIII)-3

Pyridine((R¹)ₗ)—O—phenyl(2,6-diBr)—OCH₂CH=CBr₂   (XVIII)-4

Pyridine((R¹)ₗ)—O—phenyl(2-Cl,6-Br)—OCH₂CH=CCl₂   (XVIII)-5

Pyridine((R¹)ₗ)—O—phenyl(2-Cl,6-Br)—OCH₂CH=CBr₂   (XVIII)-6

Pyridine((R¹)ₗ)—O—phenyl(2-Cl)—OCH₂CH=CCl₂   (XVIII)-7

Pyridine((R¹)ₗ)—O—phenyl(2-Cl)—OCH₂CH=CBr₂   (XVIII)-8

Pyridine((R¹)ₗ)—O—phenyl(2-Br)—OCH₂CH=CCl₂   (XVIII)-9

Pyridine((R¹)ₗ)—O—phenyl(2-Br)—OCH₂CH=CBr₂   (XVIII)-10

Pyridine((R¹)ₗ)—O—phenyl(2,5-diCl)—OCH₂CH=CCl₂   (XVIII)-11

Pyridine((R¹)ₗ)—O—phenyl(2,5-diCl)—OCH₂CH=CBr₂   (XVIII)-12

Pyridine((R¹)ₗ)—O—phenyl(2,5-diCl)—OCH₂CH=CCl₂   (XVIII)-13

Pyridine((R¹)ₗ)—O—phenyl(2,5-diCl)—OCH₂CH=CBr₂   (XVIII)-14

Pyridine((R¹)ₗ)—O—phenyl(2,5-diCH₃)—OCH₂CH=CCl₂   (XVIII)-15

TABLE 13-continued
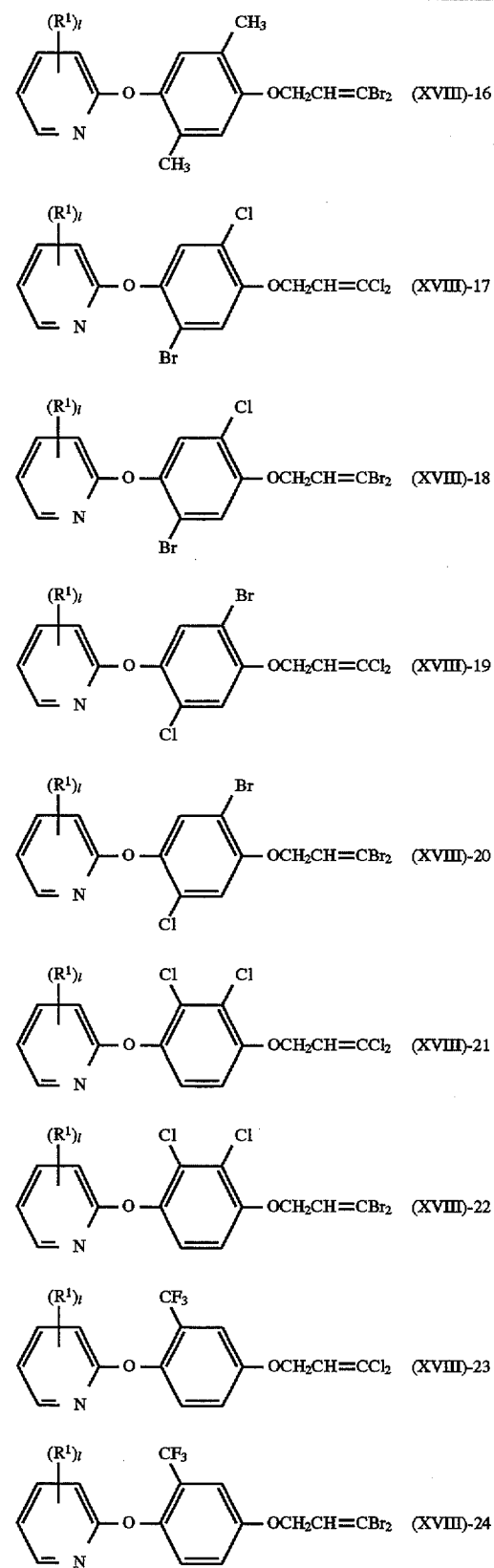
TABLE 13-continued
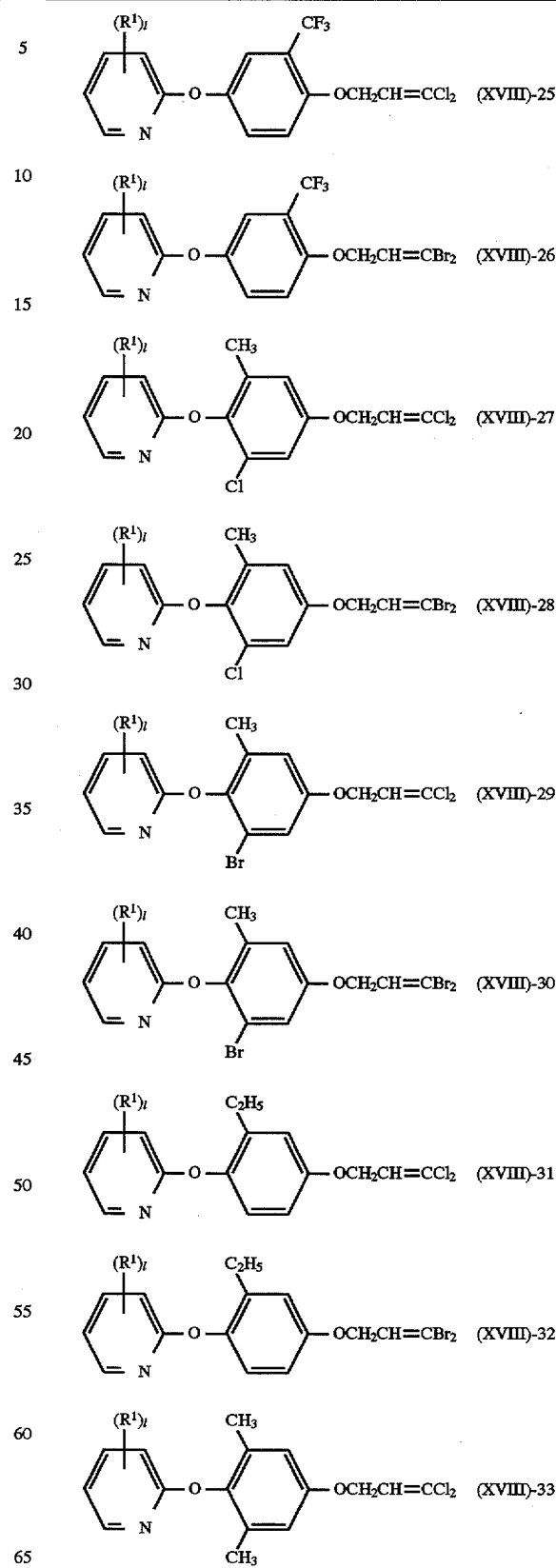

TABLE 13-continued (XVIII)-34 — pyridine-O-(2,6-dimethylphenyl)-OCH₂CH=CBr₂

(XVIII)-35 — pyridine-O-(2-isopropylphenyl)-OCH₂CH=CCl₂

(XVIII)-36 — pyridine-O-(2-isopropylphenyl)-OCH₂CH=CBr₂

| $(R^1)_l$ | $(R^1)_l$ |
|---|---|
| 6-CH₃ | 5-CH₂CH₃ |
| 6-CH₂CH₃ | 4-CH₃ |
| 6-CH₂CH₂CH₃ | 4-C₂H₅ |
| 6-phenyl | 4-CH(CH₃)₂ |
| 5-phenyl | 4-C(CH₃)₃ |
| 5-CH₃ | 4-Phenyl |
| 5-CH₃, 6-phenyl | 3,4,5,6-F₄ |
| 5,6-(CH₃)₂ | 3,5-Cl₂, 4,6-F₂ |
| 4,6-(CH₃)₂ | 3,4,5,6-Cl₄ |
| 4,5-(CH₃)₂ | 6-OCH₃ |
| 3,6-(CH₃)₂ | 6-OC₂H₅ |
| 3,5-(CH₃)₂ | 6-OCH(CH₃)₂ |
| 6-Cl | 4-OCH₃ |
| 6-Br | 4-OC₂H₅ |
| 3-Cl | 4-OCH(CH₃)₂ |
| 5-Cl | 5-OCH₃ |
| 3-Br | 5-OC₂H₅ |
| 5-Br | 5-OCH(CH₃)₂ |
| 4-Cl | 3-Br, 5-CF₃ |
| 4-Br | 3-F, 5-CF₃ |
| 5-CF₃ | 3-I, 5-CF₃ |
| 3,5-Cl₂ | 3,6-(CF₃)₂ |
| 3,5-(CF₃)₂ | 3-CF₃, 5-Cl |
| 4,5-(CF₃)₂ | 3-CF₃ |
| 4,6-(CF₃)₂ | 3,5-(CF₃)₂, 6-Cl |
| 3-Cl, 5-CF₃ | 4-CF₃ |
| 3,5,6-F₃ | 4-CF₃, 6-Cl |
| 3,5,6-F₃, 4-CH₃ | 3-CF₃, 6-Cl |
|  | 5-CF₃, 6-Cl |
|  | 5-NO₂ |
|  | 3-Br, 5-NO₂ |

The compounds of the formulae XIX-1 to 54 are shown in Table 14.

TABLE 14

(XIX)-1 — pyridine (positions 2,3,4,5,6,N₁)-O-(2-F-phenyl)-OCH₂CH=CCl₂

(XIX)-2 — pyridine-O-(2-F-phenyl)-OCH₂CH=CBr₂

(XIX)-3 — pyridine-O-(2-Cl-phenyl)-OCH₂CH=CCl₂

(XIX)-4 — pyridine-O-(2-Cl-phenyl)-OCH₂CH=CBr₂

(XIX)-5 — pyridine-O-(2-Br-phenyl)-OCH₂CH=CCl₂

(XIX)-6 — pyridine-O-(2-Br-phenyl)-OCH₂CH=CBr₂

(XIX)-7 — pyridine-O-(2-I-phenyl)-OCH₂CH=CCl₂

(XIX)-8 — pyridine-O-(2-I-phenyl)-OCH₂CH=CBr₂

(XIX)-9 — pyridine-O-(2-CH₃-phenyl)-OCH₂CH=CCl₂

(XIX)-10 — pyridine-O-(2-CH₃-phenyl)-OCH₂CH=CBr₂

(XIX)-11 — pyridine-O-(2-C₂H₅-phenyl)-OCH₂CH=CCl₂

TABLE 14-continued

| Structure | Label |
|---|---|
| Pyridine(R¹)ₗ–O–C₆H₃(C₂H₅)–OCH₂CH=CBr₂ | (XIX)-12 |
| Pyridine(R¹)ₗ–O–C₆H₃(CH₂CH₂CH₃)–OCH₂CH=CCl₂ | (XIX)-13 |
| Pyridine(R¹)ₗ–O–C₆H₃(CH₂CH₂CH₃)–OCH₂CH=CBr₂ | (XIX)-14 |
| Pyridine(R¹)ₗ–O–C₆H₃(CH(CH₃)₂)–OCH₂CH=CCl₂ | (XIX)-15 |
| Pyridine(R¹)ₗ–O–C₆H₃(CH(CH₃)₂)–OCH₂CH=CBr₂ | (XIX)-16 |
| Pyridine(R¹)ₗ–O–C₆H₃(F)–OCH₂CH=CCl₂ | (XIX)-17 |
| Pyridine(R¹)ₗ–O–C₆H₃(F)–OCH₂CH=CBr₂ | (XIX)-18 |
| Pyridine(R¹)ₗ–O–C₆H₃(I)–OCH₂CH=CCl₂ | (XIX)-19 |
| Pyridine(R¹)ₗ–O–C₆H₃(I)–OCH₂CH=CBr₂ | (XIX)-20 |
| Pyridine(R¹)ₗ–O–C₆H₃(CH₃)–OCH₂CH=CCl₂ | (XIX)-21 |
| Pyridine(R¹)ₗ–O–C₆H₃(CH₃)–OCH₂CH=CBr₂ | (XIX)-22 |
| Pyridine(R¹)ₗ–O–C₆H₂(Br)(Br)–OCH₂CH=CCl₂ | (XIX)-23 |
| Pyridine(R¹)ₗ–O–C₆H₂(Br)(Br)–OCH₂CH=CBr₂ | (XIX)-24 |
| Pyridine(R¹)ₗ–O–C₆H₂(CH(CH₃)₂)(Cl)–OCH₂CH=CCl₂ | (XIX)-25 |
| Pyridine(R¹)ₗ–O–C₆H₂(CH(CH₃)₂)(Cl)–OCH₂CH=CBr₂ | (XIX)-26 |
| Pyridine(R¹)ₗ–O–C₆H₂(CH₃)(Cl)–OCH₂CH=CCl₂ | (XIX)-27 |
| Pyridine(R¹)ₗ–O–C₆H₂(CH₃)(Cl)–OCH₂CH=CBr₂ | (XIX)-28 |
| Pyridine(R¹)ₗ–O–C₆H₂(CH₃)(Br)–OCH₂CH=CCl₂ | (XIX)-29 |
| Pyridine(R¹)ₗ–O–C₆H₂(CH₃)(Br)–OCH₂CH=CBr₂ | (XIX)-30 |

TABLE 14-continued

| Structure | Label |
|---|---|
| Pyridine-O-(2-Cl,5-methylphenyl)-OCH₂CH=CCl₂ | (XIX)-31 |
| Pyridine-O-(2-Cl,5-methylphenyl)-OCH₂CH=CBr₂ | (XIX)-32 |
| Pyridine-O-(2-Br,5-methylphenyl)-OCH₂CH=CCl₂ | (XIX)-33 |
| Pyridine-O-(2-Br,5-methylphenyl)-OCH₂CH=CBr₂ | (XIX)-34 |
| Pyridine-O-(2,6-dimethylphenyl)-OCH₂CH=CCl₂ | (XIX)-35 |
| Pyridine-O-(2,6-dimethylphenyl)-OCH₂CH=CBr₂ | (XIX)-36 |
| Pyridine-O-(2-allylphenyl)-OCH₂CH=CCl₂ | (XIX)-37 |
| Pyridine-O-(2-allylphenyl)-OCH₂CH=CBr₂ | (XIX)-38 |
| Pyridine-O-(2-CH=NOCH₃ phenyl)-OCH₂CH=CCl₂ | (XIX)-39 |
| Pyridine-O-(2-CH=NOCH₃ phenyl)-OCH₂CH=CBr₂ | (XIX)-40 |
| Pyridine-O-(2-CHF₂ phenyl)-OCH₂CH=CCl₂ | (XIX)-41 |
| Pyridine-O-(2-CHF₂ phenyl)-OCH₂CH=CBr₂ | (XIX)-42 |
| Pyridine-O-(2,3,6-trimethylphenyl)-OCH₂CH=CCl₂ | (XIX)-43 |
| Pyridine-O-(2,3,6-trimethylphenyl)-OCH₂CH=CBr₂ | (XIX)-44 |
| Pyridine-O-(2-CHF₂ phenyl)-OCH₂CH=CCl₂ | (XIX)-45 |
| Pyridine-O-(2-CHF₂ phenyl)-OCH₂CH=CBr₂ | (XIX)-46 |
| Pyridine-O-(biphenyl)-OCH₂CH=CCl₂ | (XIX)-47 |
| Pyridine-O-(biphenyl)-OCH₂CH=CBr₂ | (XIX)-48 |

TABLE 14-continued
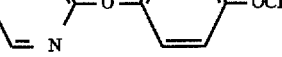
| (R¹)ₗ | (R¹)ₗ |
|---|---|
| 5-phenyl | 4-OCH(CH₃)₂ |
| 5-C₂H₅ | 5-OCH₃ |
| 4-CH(CH₃)₂ | 5-OC₂H₅ |
| 4-phenyl | 5-CH(CH₃)₂ |
| 5-CF₃ | 3-Br, 5-CF₃ |
| 3,5-(CF₃)₂ | 3,6-(CF₃)₂ |
| 4,5-(CF₃)₂ | 3-CF₃, 5-Cl |
| 4,6-(CF₃)₂ | 3-CF₃ |
| 3-Cl, 5-CF₃ | 3,5-(CH₃)₂, 6-Cl |
| 6-OCH₃ | 4-CF₃ |
| 6-OC₂H₅ | 4-CF₃, 6-Cl |
| 6-OCH(CH₃)₂ | 3-CF₃, .6-Cl |
| 4-OCH₃ | 3-CF₃, 6-Cl |
| 4-OC₂H₅ | 5-CF₃, 6-Cl |
The position of R¹ is numbered as shown in the formula XIX-1.
The compounds of the formulae XX-1 to 16 are shown in Table 15.
TABLE 15
TABLE 15-continued

TABLE 15-continued
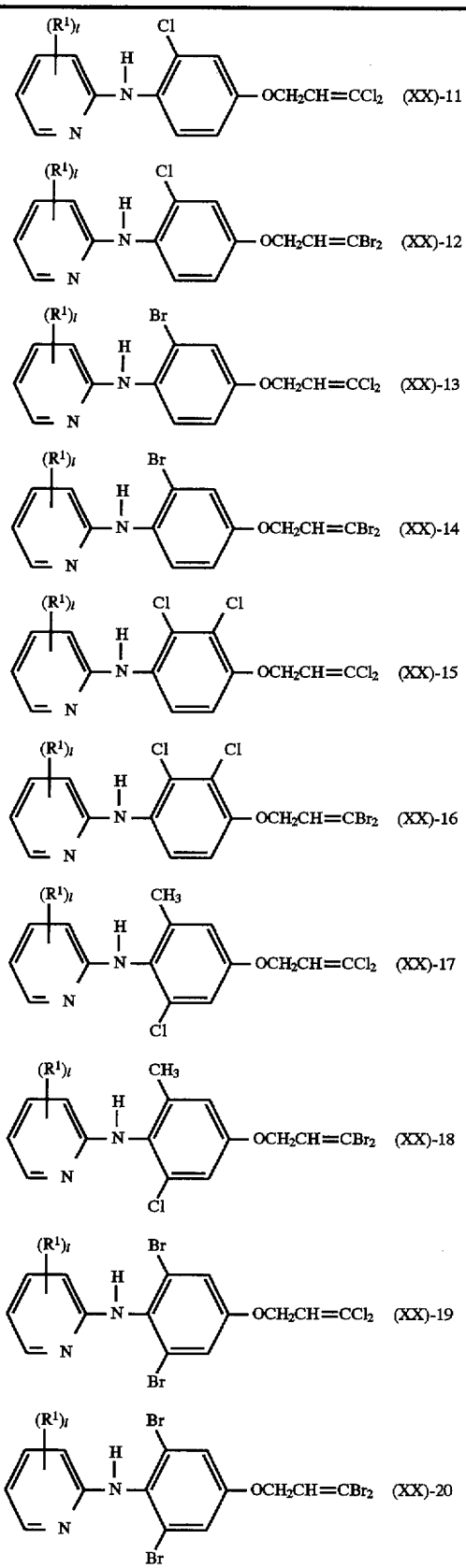
| $(R^1)_l$ | $(R^1)_l$ |
|---|---|
| 5-phenyl | 4-OCH(CH$_3$)$_2$ |
| 5-C$_2$H$_5$ | 5-OCH$_3$ |
| 4-CH(CH$_3$)$_2$ | 5-OC$_2$H$_5$ |
| 4-phenyl | 5-CH(CH$_3$)$_2$ |
| 5-CF$_3$ | 3-Br, 5-CF$_3$ |
| 3,5-(CF$_3$)$_2$ | 3,6-(CF$_3$)$_2$ |
| 4,5-(CF$_3$)$_2$ | 3-CF$_3$, 5-Cl |
| 4,6-(CF$_3$)$_2$ | 3-CF$_3$ |
| 3-Cl, 5-CF$_3$ | 3,5-(CF$_3$)$_2$, 6-Cl |
| 6-OCH$_3$ | 4-CF$_3$ |
| 6-OC$_2$H$_5$ | 4-CF$_3$, 6-Cl |
| 6-OCH(CH$_3$)$_2$ | 3-CF$_3$, 6-Cl |
| 4-OCH$_3$ | 5-CF$_3$, 6-Cl |
| 4-OC$_2$H$_5$ | |
The position of $R^1$ is numbered as shown in the formula XX-1.
The compounds of the formulae XXI-1 to 16 are shown in Table 16.

TABLE 16-continued
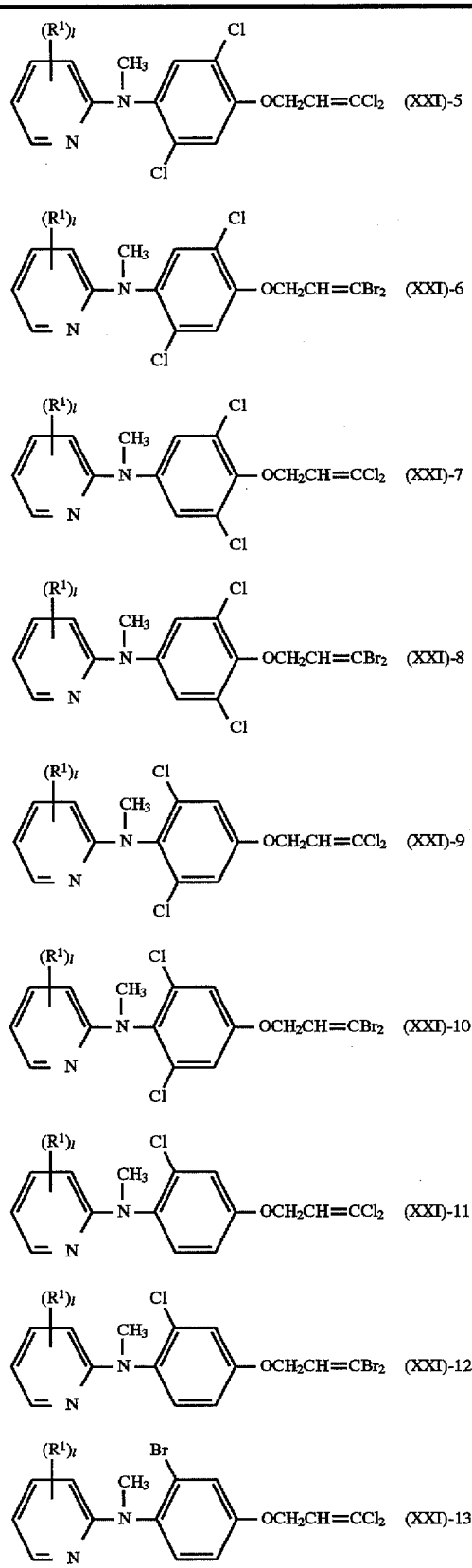
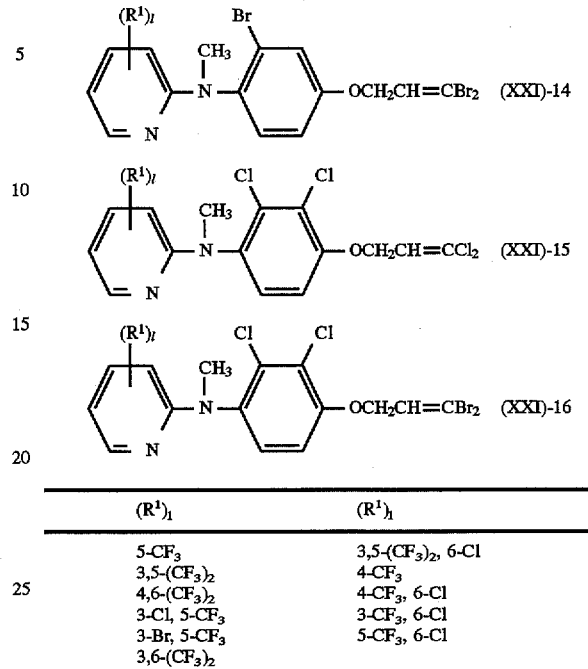
| $(R^1)_l$ | $(R^1)_l$ |
|---|---|
| 5-CF₃ | 3,5-(CF₃)₂, 6-Cl |
| 3,5-(CF₃)₂ | 4-CF₃ |
| 4,6-(CF₃)₂ | 4-CF₃, 6-Cl |
| 3-Cl, 5-CF₃ | 3-CF₃, 6-Cl |
| 3-Br, 5-CF₃ | 5-CF₃, 6-Cl |
| 3,6-(CF₃)₂ | |
The position of $R^1$ is numbered as shown in the formula XXI-1.
The compounds of the formulae XXII-1 to 14 are shown in Table 17.
TABLE 17
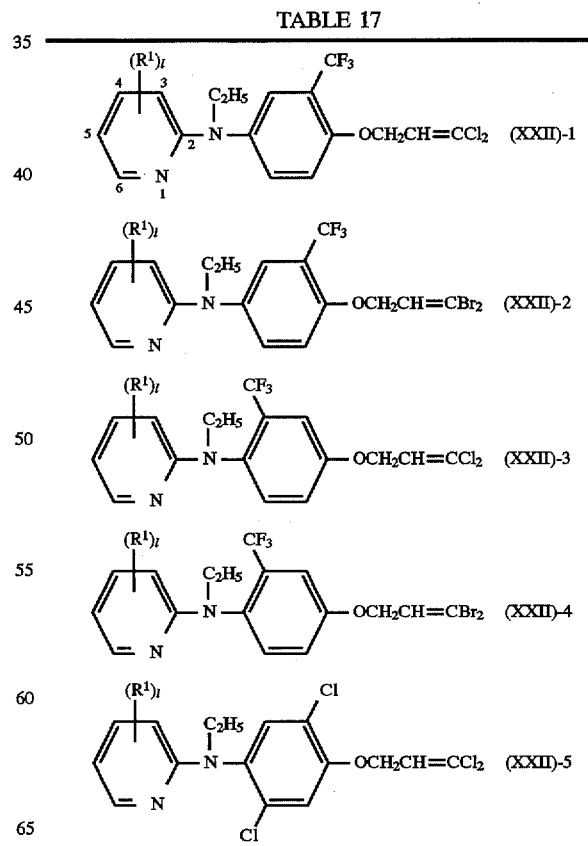

TABLE 17-continued (structures of compounds XXII-6 through XXII-14, each showing a pyridine ring with (R¹)ₗ substituents connected via N-C₂H₅ to a substituted phenyl group)

- (XXII)-6: 2,5-diCl, 4-OCH₂CH=CBr₂ phenyl
- (XXII)-7: 2,3,5-triCl, 4-OCH₂CH=CCl₂ phenyl
- (XXII)-8: 2,3,5-triCl, 4-OCH₂CH=CBr₂ phenyl
- (XXII)-9: 2,6-diCl, 4-OCH₂CH=CCl₂ phenyl
- (XXII)-10: 2,6-diCl, 4-OCH₂CH=CBr₂ phenyl
- (XXII)-11: 2-Cl, 4-OCH₂CH=CCl₂ phenyl
- (XXII)-12: 2-Cl, 4-OCH₂CH=CBr₂ phenyl
- (XXII)-13: 2-Br, 4-OCH₂CH=CCl₂ phenyl
- (XXII)-14: 2-Br, 4-OCH₂CH=CBr₂ phenyl

| (R¹)₁ | (R¹)ₗ |
|---|---|
| 5-CF₃ | 3,5-(CF₃)₂, 6-Cl |
| 3,5-(CF₃)₂ | 4-CF₃ |
| 4,6-(CF₃)₂ | 4-CF₃, 6-Cl |
| 3-Cl, 5-CF₃ | 3-CF₃, 6-Cl |
| 3-Br, 5-CF₃ | 5-CF₃, 6-Cl |
| 3,6-(CF₃)₂ | |

The position of R¹ is numbered as shown in the formula XXII-1.

The compounds of the formulae XXIII-1 to 8 are shown in Table 18.

TABLE 18

(structures of compounds XXIII-1 through XXIII-7, each showing a pyridine ring (positions numbered 1-6 with N at 1) with (R¹)ₗ substituents connected via N-COCF₃ or N-COCH₃ to a substituted phenyl group)

- (XXIII)-1: N-COCF₃; 2,6-diCl, 4-OCH₂=CCl₂ phenyl
- (XXIII)-2: N-COCF₃; 2,6-diCl, 4-OCH₂=CBr₂ phenyl
- (XXIII)-3: N-COCH₃; 2,6-diCl, 4-OCH₂=CCl₂ phenyl
- (XXIII)-4: N-COCH₃; 2,6-diCl, 4-OCH₂=CBr₂ phenyl
- (XXIII)-5: N-COCH₃; 3-Cl, 4-OCH₂=CCl₂ phenyl
- (XXIII)-6: N-COCH₃; 3-Cl, 4-OCH₂=CBr₂ phenyl
- (XXIII)-7: N-COCH₃; 3-Br, 4-OCH₂=CCl₂ phenyl

TABLE 18-continued (Structure with (R¹)ₗ, COCH₃, Br, N, OCH₂=CBr₂) (XXIII)-8

| (R¹)ₗ | (R¹)ₗ |
|---|---|
| 3,5-(CF₃)₂ | 3-Br, 5-CF₃ |
| 3-Cl, 5-CF₃ | |

The position of R¹ is numbered as shown in the formula XIII-1.

The compounds of the formulae XXIV-1 to 14 are shown in Table 19.

TABLE 19

(XXIV)-1 — pyridine-O-(2,6-dichlorophenyl)-NH-CH₂CH=CCl₂

(XXIV)-2 — pyridine-O-(2,6-dichlorophenyl)-NH-CH₂CH=CBr₂

(XXIV)-3 — pyridine-O-(2,3-dichlorophenyl)-NH-CH₂CH=CCl₂

(XXIV)-4 — pyridine-O-(2,3-dichlorophenyl)-NH-CH₂CH=CBr₂

(XXIV)-5 — pyridine-O-(3,5-dichlorophenyl)-NH-CH₂CH=CCl₂

(XXIV)-6 — pyridine-O-(3,5-dichlorophenyl)-NH-CH₂CH=CBr₂

(XXIV)-7 — pyridine-O-(3-chlorophenyl)-NH-CH₂CH=CCl₂

(XXIV)-8 — pyridine-O-(2-chlorophenyl)-NH-CH₂CH=CBr₂

(XXIV)-9 — pyridine-O-(2-bromophenyl)-NH-CH₂CH=CCl₂

(XXIV)-10 — pyridine-O-(2-bromophenyl)-NH-CH₂CH=CBr₂

(XXIV)-11 — pyridine-O-(2-chloro-6-bromophenyl)-NH-CH₂CH=CCl₂

(XXIV)-12 — pyridine-O-(2-chloro-6-bromophenyl)-NH-CH₂CH=CBr₂

(XXIV)-13 — pyridine-O-(2,6-dibromophenyl)-NH-CH₂CH=CCl₂

(XXIV)-14 — pyridine-O-(2,6-dibromophenyl)-NH-CH₂CH=CBr₂

| (R¹)ₗ | (R¹)ₗ |
|---|---|
| 3-Cl, 5-CF₃ | 5-CF₃ |
| 3-Br, 5-CF₃ | 5-phenyl |
| 3,5-(CF₃)₂ | 4-phenyl |
| 3,5-(CF₃)₂, 6-Cl | 6-phenyl |

The position of R¹ is numbered as shown in the formula XXIV-1.

The compounds of the formulae XXV-1 to 8 are shown in Table 20.

TABLE 20

(XXV)-1: pyridyl(R¹)ₗ–O–pyridyl(Cl)–OCH₂CH=CCl₂

(XXV)-2: pyridyl(R¹)ₗ–O–pyridyl(Cl)–OCH₂CH=CBr₂

(XXV)-3: pyridyl(R¹)ₗ–O–pyridyl(Br)–OCH₂CH=CCl₂

(XXV)-4: pyridyl(R¹)ₗ–O–pyridyl(Br)–OCH₂CH=CBr₂

(XXV)-5: pyridyl(R¹)ₗ–O–pyridyl(Cl)–OCH₂CH=CCl₂

(XXV)-6: pyridyl(R¹)ₗ–O–pyridyl(Cl)–OCH₂CH=CBr₂

(XXV)-7: pyridyl(R¹)ₗ–O–pyridyl(Br)–OCH₂CH=CCl₂

(XXV)-8: pyridyl(R¹)ₗ–O–pyridyl(Br)–OCH₂CH=CBr₂

| (R¹)ₗ | (R¹)ₗ |
|---|---|
| 5-CF₃ | 5-phenyl |
| 3-Cl, 5-CF₃ | 4-cyclohexyl |
| 3-Br, 5-CF₃ | 5-cyclohexyl |
| 3,5-(CF₃)₂ | 3,5-(CF₃)₂, 6-Cl |
| 4-phenyl | |

The position of R¹ is numbered as shown in the formula XXV-1.

The compounds of the formulae XXVI-1 to 8 are shown in Table 21.

TABLE 21

(XXVI)-1: phenyl(R²)ₗ–O–pyridyl(Cl)–OCH₂CH=CCl₂

(XXVI)-2: phenyl(R²)ₗ–O–pyridyl(Cl)–OCH₂CH=CBr₂

(XXVI)-3: phenyl(R²)ₗ–O–pyridyl(Br)–OCH₂CH=CCl₂

(XXVI)-4: phenyl(R²)ₗ–O–pyridyl(Br)–OCH₂CH=CBr₂

(XXVI)-5: phenyl(R²)ₗ–O–pyridyl(Cl)–OCH₂CH=CCl₂

(XXVI)-6: phenyl(R²)ₗ–O–pyridyl(Cl)–OCH₂CH=CBr₂

(XXVI)-7: phenyl(R²)ₗ–O–pyridyl(Br)–OCH₂CH=CCl₂

(XXVI)-8: phenyl(R²)ₗ–O–pyridyl(Br)–OCH₂CH=CBr₂

| (R¹)ₗ | (R¹)ₗ |
|---|---|
| 4-OCH₃ | 4-OCH₂CF₃ |
| 3-OCH₃ | 3-cyclohexyl |
| 4-OC₂H₅ | 4-cyclohexyl |
| 3-OC₂H₅ | 3-cyclopentyl |
| 4-OCH(CH₃)₂ | 4-cyclopentyl |
| 3-OCH(CH₃)₂ | 3-phenoxy |
| 3-OCF₃ | 4-phenoxy |
| 4-OCF₃ | 3-phenyl |
| 3-OCH₂CF₃ | 4-phenyl |

The intermediate compound II of the present invention can be produced, for example, by the methods of schemes 1 to 10.
Scheme 1.
Y¹ is O, NR³ or S; L¹ is a halogen; L² is methyl or benzyl; and other symbols are the same as above.
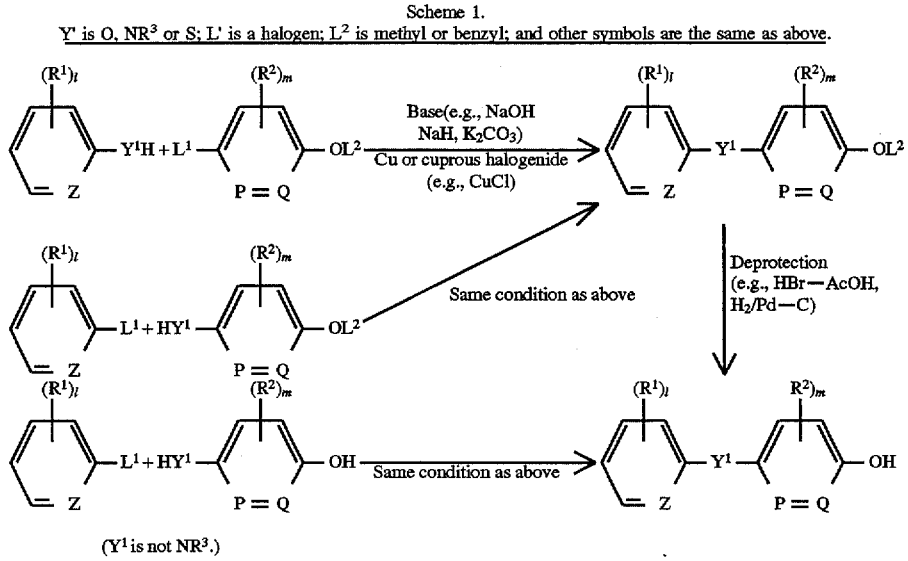
(Y¹ is not NR³.)
Scheme 2.
L³ is hydrogen or acetyl; and other symbols are the same as defined above
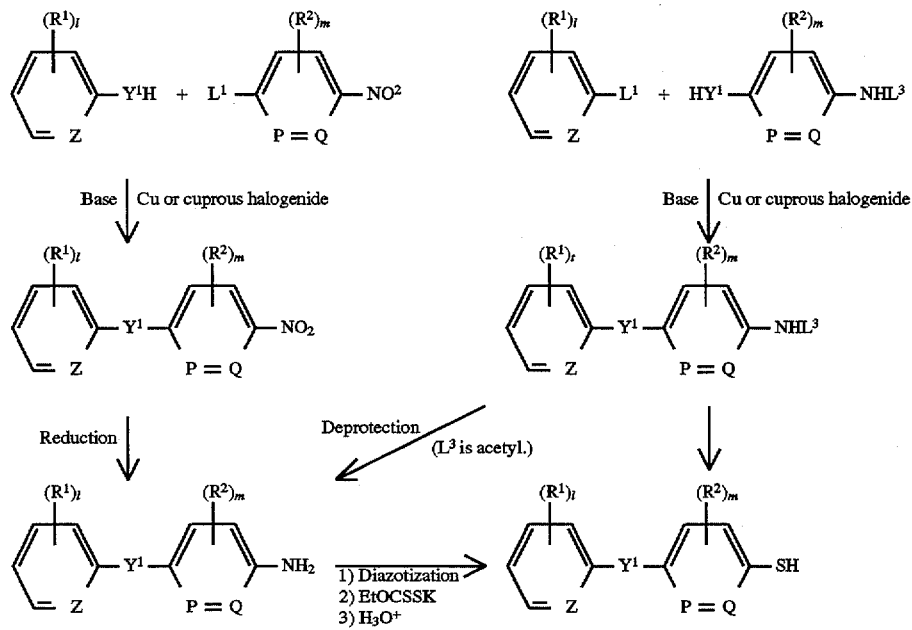

Scheme 3.
The symbols are the same as defined above.
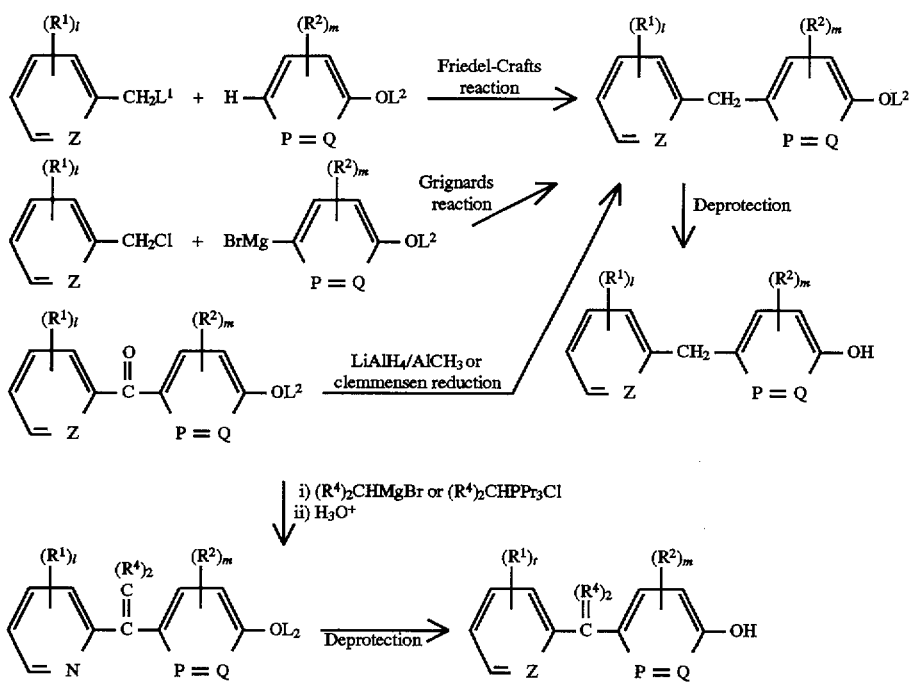
Scheme 4.
$q^1$ is an integer of 1 or 2, and other symbols are the same as above.
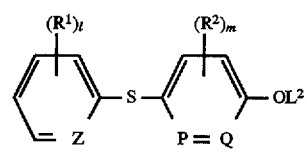
Oxidant
(e.g., $H_2O_2$—AcOH)
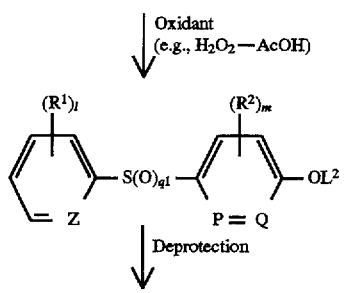
Deprotection
-continued
Scheme 4.
$q^1$ is an integer of 1 or 2, and other symbols are the same as above.
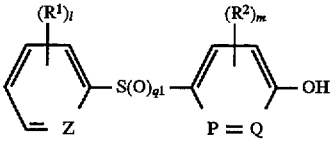

Scheme 5.
The symbols are the same as defined above.

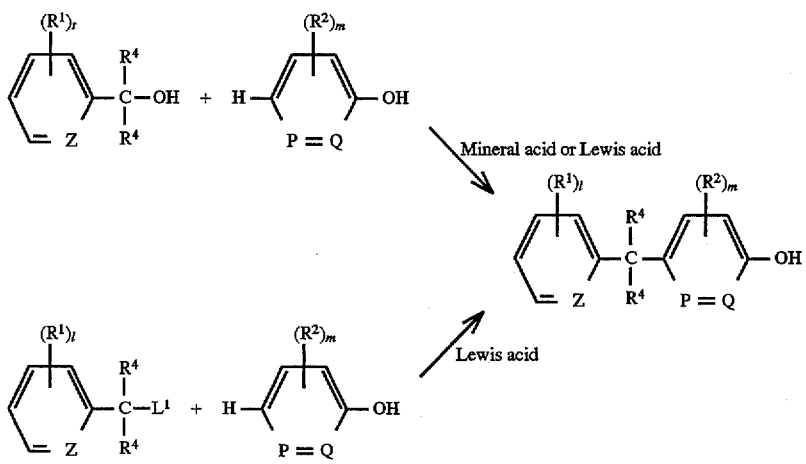

Scheme 6.
$Y^2$ is a Y other than NH; D' is oxygen or NH; $R^{21}$ and $R^{22}$ are the same or different and are independently hydrogen, chlorine, bromine or iodine, with the proviso that they are not simultaneously hydrogen; and others are the same as defined above.

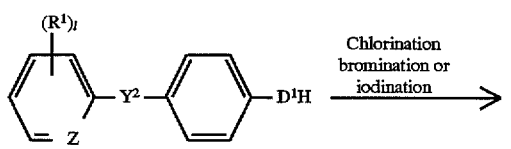

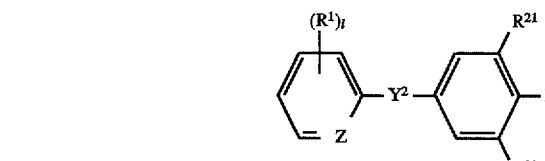

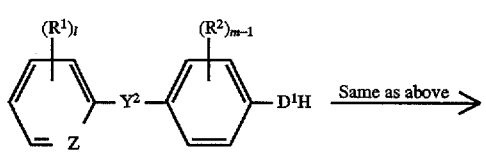

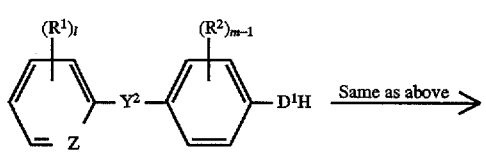

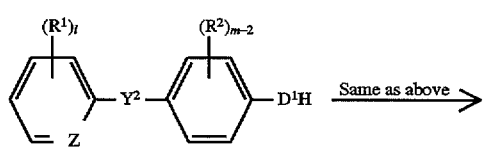

-continued
Scheme 6.
$Y^2$ is a Y other than NH; D' is oxygen or NH; $R^{21}$ and $R^{22}$ are the same or different and are independently hydrogen, chlorine, bromine or iodine, with the proviso that they are not simultaneously hydrogen; and others are the same as defined above.

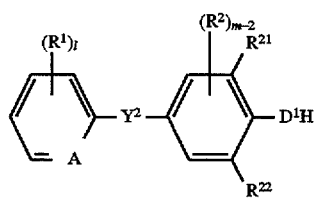

Scheme 7.

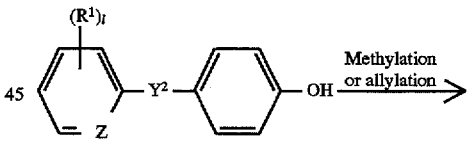

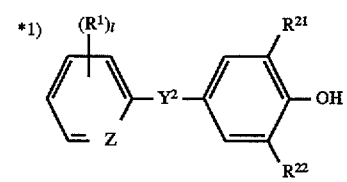

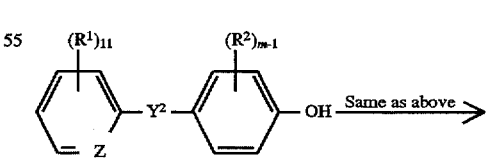

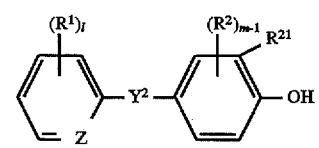

-continued
Scheme 7.

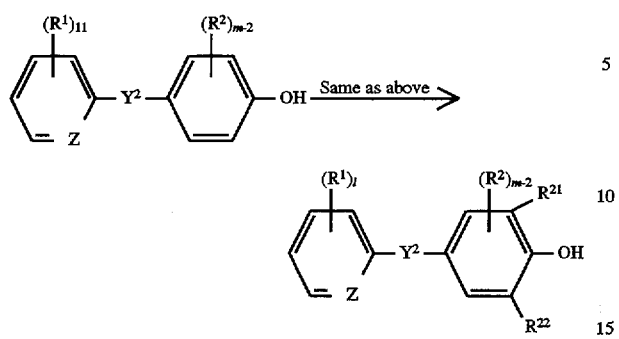

$Y^2$ is a Y other than NH; $R^{21}$ and $R^{22}$ are the same or different and are independently a hydrogen, methyl or an allyl, with the proviso that they are not simultaneously hydrogen; and others are the same as defined above

*1) See, e.g., Tetrahedron Lett., 889 (1974).

-continued
Scheme 9.

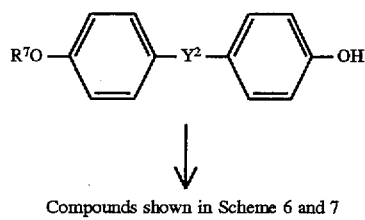

Compounds shown in Scheme 6 and 7

$R^7$ is a $C_1$-$C_7$ alkyl, $C_1$-$C_3$ haloalkyl, $C_3$-$C_6$ alkenyl or $C_3$-$C_6$ haloalkenyl; and $Y^2$ is the same as defined above.

The intermediate aldehyde compound of the formula V of the present invention can be produced by the following scheme:

Scheme 8.

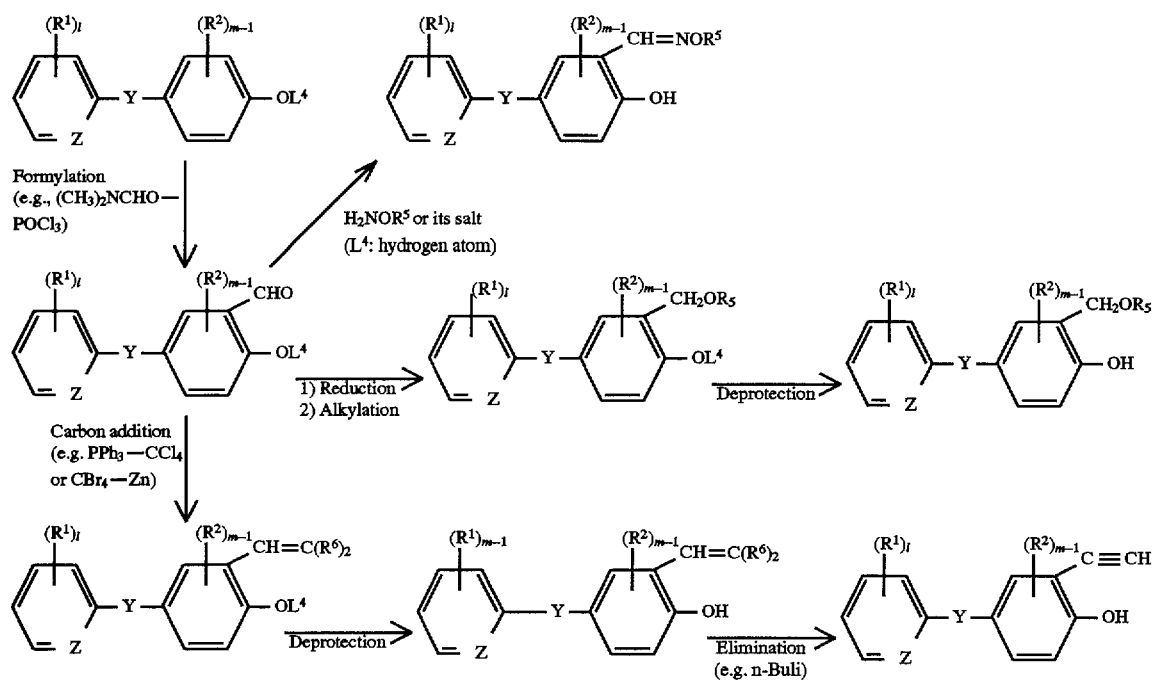

$L^{4a}$ hydrogen or methoxymethyl; $R^5$ is an alkyl of $C_1$-$C_3$; $R^6$ is chlorine or bromine; and other symbols are the same as defined above.

Scheme 9.

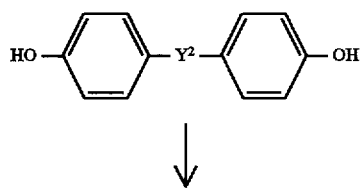

Scheme 10.

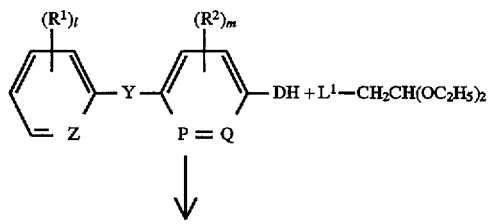

-continued
Scheme 10.

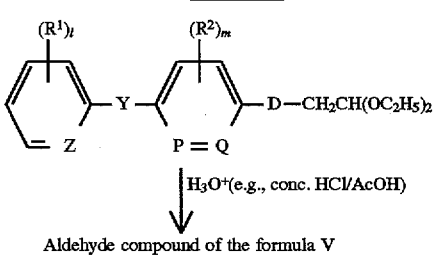

Aldehyde compound of the formula V

The symbols are the same as defined above.

The intermediate compound represented by the formula III and the alcohol compound represented by the formula IV can be produced by the scheme 11 below or commercially available.

Scheme 11.

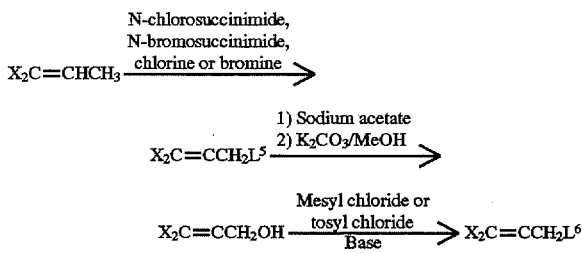

$L^5$ is chlorine or bromine, $L^6$ is mesyloxy or tosyloxy, and X is the same as defined above.

The dihalopropene compound of the present invention is effective for controlling noxious insects, mites and nematodes listed below:
Hemiptera Delphacidae (planthoppers) such as *Laodelphax striatellus, Nilaparvata lugens* and *Sogatella furcifera*; Deitocephalidae (leaf hoppers) such as *Nephotettix cincticeps* and *Nephotettix virescens*, Aphididae (aphids), Pentatomidae (stink bugs), Aleyrodidae, Coccoidea (scale insects), Tingidae (lacebugs), Psyllidae (jumping plant-lices), etc.;
Lepidoptera Pyralidae such as *Chilo suppressalis, Cnaphalocrocis medinalis, Ostrinia nubilalis, Parapediasia teterrella, Notarcha derogata* and *Plodia interpunctella*, Noctuidae (owlet moths) such as *Spodoptera litura, Pseudaletia separata, Mamestra brassicae, Agrotis ipsilon,* Heliothis moths, Helicoverpa moths, Pieridae such as *Pieris rapae crucivora,* Tortricidae (bell moths) such as *Grapholita molesta* and *Cydia pomonella, Carposina niponensis,* Lyonetiidae (leaf mining moths), Euproctis and Lymantria (gypsy) moths, Yponomeutidae such as *Plutella xylostella,* Gelechiidae such as *Pectinophora gossypiella,* Arctiidae such as *Hyphantria cunea, Tinea translucens, Tineola bisselliella,* etc.;
Diptera Culex (house mosquitos) such as *Culex pipiens pallens* and *Cules tritaeniorhynchus,* Aedes such as *Aedes albopictus* and *Aedes aegypti,* Anophelinae such as *Anophelies sinensis,* Chironomidae (midges), Muscidae such as *Musca domestica* (house fly) and *Muscina stabulans,* Calliphoridae (blow flies), Sarcophagidae (flesh flies), Anthomyiidae such as *Delia Platura* and *Delia antigua,* Trypetidae (fruit flies), Drosophilidae (wine flies), Psychodidae (moth flies), Tabanidae (deer flies), Simuliidae (black flies), Stomoxyinae, Agromyzidae (leaf miner flies) etc.;

Coleoptera (beetles)

Diabrotica (corn rootworms) such as *Diabrotica virgifera* and *Diabrotica undecimpunctata,* Scarabaeidae such as *Anomala cuprea* and *Anomala rufocuprea,* Curculionidae (snout beetles) such as *Sitophilus zeamais* (grain weevils), *Lissorhoptrus oryzophilus, Hypera postica,* and *Callosobruchus chinesis, Neatus ventralis* (darkling beetles) such as *Tenebrio molitor* and *Tribolium castaneum,* Chrysomelidae (leaf beetles) such as *Aulacophora femoralis,* and *Phyllotreta striolata,* Anobiidae (death-watch beetles), Epilachna spp. such as *Epilachna vigintioctopunctata,* Lyctidae (powder-post beetles), Bostrychidae (lesser grain borers), Cerambycidae, etc.;
Blattaria (cockroaches)

Blattella germanica (croton bugs), *Periplaneta fuliginosa, Periplaneta americana, Periplaneta brunnea, Blatta orientalis,* etc.;
Thysanoptera (thrips)

*Thrips palmi, Thrips tabaci, Thrips hawaiiensis,* etc.;
Hymenoptera

Formicidae (ants), Vespa (hornets), Bethylidae (bethylid wasps), Tenthredinoidae (sawflies) such as *Athalia rosae japonensis* (cabbage sawfly), etc.;
Orthoptera Gryllotalpha (mole crickets), Acridoidea (grasshoppers), etc.;
Siphonaptera (fleas)

Purex irritans, etc.;
Anoplura (sucking louses)

*Pediculus humanus capitis, Phthirus pubis,* etc.;
Isoptera (termites)

*Reticulitermes speratus, Coptotermes formosanus,* etc.;
Mites

Tetranychidae (spider mites) such as *Tetranychus cinnabarinus, Tetranychus urticae, Tetranychus kanzawai, Panonychus citri* and *Panonychus ulmi,* Eriophyidae such as *Aculops pelekassi* and *Calacarus carinatus,* Tarsonemidae such as *Polyphaqotarsonemus latus,* Tenuipalpidae, Tuckerellidae, Ixodidae (ticks) such as *Boophilus microplus,* Acaridae, Pyroglyphidae, Cheyletidae, Dermanyssidae, etc.;

Moreover, the dihalopropene compounds of the present invention are also effective for controlling various insects with increased resistance to commercially available insecticides.

For the practical use of the dihalopropene compound of the present invention as an active ingredient of insecticides, acaricide or nematocides, it may be used as such; however, the dihalopropene compound of the present invention is usually formulated into oil sprays, emulsifiable concentrates, wettable powders, flowable concentrates such as water suspensions or emulsions, granules, dusts, aerosols, heating fumigants such as combustible fumigant, chemical fumigant and porous ceramics fumigant, ULV formulations and poison baits. These formulations are usually prepared by mixing the dihalopropene compound of the present invention with a solid carrier, a liquid career, a gaseous carrier or bait, and a surfactant and any other auxiliary for formulation are added thereto, if necessary. These formulations usually contain the dihalopropene compound of the present invention as an active ingredient in an mount of 0.01% to 95% by weight.

Examples of the solid carrier to be used for the formulation are fine powder or granules of clays such as kaolin clay, diatomaceous earth, synthetic hydrated silicon oxide, bentonite and acid clay; talc, ceramics, inorganic minerals such as sericite, quartz, sulfur, active carbon, calcium carbonate and hydrated silica; and chemical fertilizers such as ammonium sulfate, ammonium phosphate, ammonium nitrate, urea and ammonium chloride. Examples of the liquid carrier are water; alcohols such as methanol and ethanol; ketones such as acetone and methylethyl ketone; aromatic hydrocarbons such as benzene, toluene, xylene, ethylbenzene and methylnaphthalene; aliphatic hydrocarbons such as hexane, cyclohexane, kerosine and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil. Examples of the gaseous carrier or propellant are CFCs (chlorofluorocarbons), butane gas, LPG (liquefied petroleum gas), diethyl ether and carbon dioxide.

Examples of the surfactant are alkyl sulfates, alkyl sulfonates, alkyl arylsulfonates, alkyl aryl ethers, polyethylene glycols, polyethylene glycol ethers, polyhydric alcohol derivatives and sugar alcohol derivatives.

Examples of the auxiliary for the formulation, such as a fixing agent or a dispersing agent, are casein, gelatin, polysaccharides such as starch, gum arabic, cellulose derivatives and alginic acid, lignin derivatives, bentonite, sugars and synthetic water-soluble polymers such as polyvinyl alcohol, polyvinyl pyrrolidone and polyacrylic acid. Examples of the stabilizer are PAP (isopropyl acid phosphate), BHT (2,6-di-t-butyl-4-methylphenol), BHA (mixture of 2-t-butyl-4-methoxyphenol and 3-t-butyl-4-methoxyphenol), vegetable oils, mineral oils, surfactants, fatty acids and esters of fatty acids.

Examples of the base material to be used in the combustible fumigant are exothermic agents such as nitrates, nitrites, guanidine salts, potassium chlorate, nitrocellulose, ethylcellulose or wood powder; pyrolytic stimulating agents such as alkaline metal salts, alkaline earth metal salts, dichromates or chromates; oxygen sources such as potassium nitrates; combustion assistants such as melamine or wheat starch; bulk fillers such as diatomaceous earth; and binding agents such as synthetic glue.

Examples of the base material to be used in the chemical fumigant are exothermic agents such as alkaline metal sulfides, polysulfides, hydrogensulfides, hydrated salts or calcium oxide; catalytic agents such as carbonaceous substances, iron carbide or active clay; organic foaming agents such as azodicarbonamide, benzenesulfonylhydrazide, N,N'-dinitrosopentamethylenetetramine, polystyrene or polyurethane; and fillers such as natural and synthetic fibers.

Examples of the base material to be used in the poison baits are bait materials such as grain powder, purified vegetable oil, sulfur or crystalline cellulose; antioxidants such as dibutylhydroxytoluene or nordihydroguaiaretic acid; preservatives such as dehydroacetic acid; substances for preventing erroneous eating, such as red pepper powder; attractant flavors such as cheese flavor or onion flavor.

The flowable concentrates such as water suspensions and emulsions are usually obtained by finely dispersing the dihalopropene compound of the present invention at a ratio of 1% to 75% in water containing a 0.5% to 15% dispersing agent, a 0.1% to 10% suspension assistant (e.g., protective colloid or a thixotropy-giving compound) and 0% to 10% additives (e.g., antifoamers, stabilizers, bactericides, rust preventive agents, antimolds, developing agents, penetrating assistants and anti freezing agents).

The dihalopropene compound of the present invention may be dispersed in oil having substantially no solubility thereof, to form oil suspensions. Examples of the protective colloid are casein, gelatin, gums, cellulose ethers and polyvinyl alcohol. Examples of the thixotropy-giving compound are bentonite, aluminum magnesium silicate, xanthan gum or polyacrylic acid.

The formulation thus obtained is used as such or after dilution with water. The formulations of the present invention may be used together with other insecticides, acaricides, nematocides, bactericides, herbicides, plant growth regulators, synergists, fertilizers and/or soil conditioners under non-mixing conditions or pre-mixing conditions.

Examples of the insecticide, acaricide and/or nematocide to be used are organophosphorous compounds such as Fenitrothion [(O,O-dimethyl O-(3-methyl-4-nitrophenyl) phosphorothionate], Fenthion [O,O-dimethyl O-(3-methyl-4-methylthiophenyl)phosphorothionate], Diazinon (Dimpylate) [O,O-diethyl-O-2-isopropyl-6-methylpyrimidin-4-ylphosphorothioate], Chlorpyriphos [O,O-diethyl-O-3,5,6-trichloro-2-pyridylphosphorothioate], Acephate [O,S-dimethyl acetylphosphoramidothioate], Methidachion (DMTP) [S-2,3-dihydro-5-methoxy-2-oxo-1,3,4-thiadiazol-3-ylmethyl O,O-dimethylphosphorothiolothionate], Disulfoton [O,O-diethyl S-2-ethylthioethyl phosphorothiolothionate], Dichlorvos (DDVP) [2,2-dichlorovinyl dimethyl phosphate], Sulprofos [O-ethyl O-4-methylthiophenyl S-propyl phosphorodithioate], Cyanophos [O-4-cyanophenyl-O,O-dimethylphosphorothioate], Dioxabenzofos [2-methoxy-4H-1,3,2-benzodioxaphosphorin-2-sulfide], Dimethoate [O,O-dimethyl S-(N-methyl-carbamoylmethyl) phosphorodithioate], Phenthoate [ethyl 2-dimethoxyphosphinothiaylthiophenylacetate], Malathion [1,2-bis(ethoxylcarbonyl)-ethyl O,O-dimethyl phosphorothiolothionate], Trichlorfon (Metrifonate) [dimethyl 2,2,2-trichloro-1-hydroxyethyl phosphonate], Azinphos-methyl [S-(3,4-dihydro-4-oxo-1,2,3-benzotriazine-3-ylmethyl) dimethyl phosphorothiolothionate], Monocrotophos [dimethyl-(E)-1-methyl-2-(methylcarbamoyl)vinyl phospahte]and Ethion [O,O,O',O'-tetraethyl-S,S'-methylenebis (phosphorothiolothionate)].

Other examples are carbamate compounds such as BPMC [2-sec-butylphenyl methyl carbamate], Benfuracarb [ethyl N-(2,3-dihydro-2,2-dimethyl benzofuran-7-yloxycarbonyl (methyl)aminothio)-N-isopropyl-β-alaninate], Propoxur (PHC) [2-isopropoxyphenyl N-methyl carbamate], Carbosulfan [2,3-dihydro-2,2-dimethyl-7-benzo[b]furanyl N-dibutylaminothio-N-methyl carbamate], Carbaril [1-naphthyl N-methylcarbamate], Methomyl [S-methyl-N-( (methylcarbamoyl)oxy)thioacetoimidate], Ethiofencarb [2-(ethylthiomethyl)phenyl methylcarbamate], Aldicarb [2-methyl-2-(methylthio)propionaldehyde O-(methylcarbamoyl)oxime], Oxamyl [N,N-dimethyl 2-methylcarbamoyloxyimino-2-(methylthio)acetamide] and Fenothiocarb [S-(4-phenoxybutyl)-N,N-dimethyl thiocarbamate].

Other examples are pyrethroid compounds such as Etofenprox [2-(4-ethoxyphenyl)-2-methylpropyl-3-phenoxybenzyl ether], Fenvalerate [(RS)-α-cyano-3-phenoxybenzyl-(RS)-2-(4-chlorophenyl)-3-methylbutyrate], S-Fenvalerate [(S)-α-cyano-3-phenoxybenzyl (S)-2-(4-chlorophenyl)-3-methylbutyrate], Fenpropathrin [(RS)-α-cyano-3-phenoxybenzyl 2,2,3,3-tetramethylcyclopropanecarboxylate], Cypermethrin [(RS)-α-cyano-3-phenoxybenzyl (1RS,3RS)-3-(2,2-dichlorovinyl) -2,2-dimethylcyclopropanecarboxylate], Permethrin [3-phenoxybenzyl (1RS,3RS)-3-(2,2-dichlorovinyl)-2,2-dimethylcyclopropanecarboxylate], Cyhalothrin [(RS)-α- cyano-3-phenoxybenzyl (Z)-(1RS)-cis-3-(2-chloro-3,3,3-trifluoropropen-1-yl)-2,2-dimethylcyclopropane carboxylate], Deltamethrin [(S)-α-cyano-3-phenoxybenzyl (1R,3R)-3-(2,2-dibromovinyl)-2,2-dimethylcyclopropanecarboxylate], Cycloprothrin [(RS)-α-cyano-3-phenoxybenzyl (RS)-2,2-dichloro-1-(4-ethoxyphenyl)cyclopropanecarboxylate], Fluvalinate [α-cyano-3-phenoxybenzyl N-(2-chloro-α,α,α-trifluoro-p-tolyl)-D-valinate], Bifenthrin [2-methylbiphenyl-3-ylmethyl) (Z)-(1RS)-cis-3-(2-chloro-3,3,3-trifluoropropen-1-yl)-2,2-dimethylcyclopropanecarboxylate], Acrinathrin [(S)-(α)-cyano-(3-phenoxyphenyl)methyl (1R)-(1α(S*),3α(Z))-2,2-dimethyl-3-(3-oxo-3-(2,2,2-trifluoro-1-(trifluoromethyl)ethoxy-1-propenyl) cyclopropanecarboxylate], 2-methyl-2-(4-bromodifluoromethoxyphenyl)propyl (3-phenoxybenzyl) ether, Traromethrin [(S)-α-cyano-3-phenoxylbenzyl (1R,3S)-3-((1'RS)(1',1',2',2'-tetrabromoethyl))-2,2-dimethylcyclopropanecarboxylate] and Silafluofen [4-ethoxylphenyl(3-(4-fluoro-3-phenoxyphenyl)propyl) dimethylsilane].

Other examples are thiadiazine derivatives such as Buprofezin [2-t-butylimino-3-isopropyl-5-phenyl-1,3,5-thiadiazin-4-one], nitroimidazolidine derivatives such as Imidacloprid [1-(6-chloro-3-pyridylmethyl)-N-nitroimidazolidin-2-ylidenamine], Nereistoxin derivatives such as Cartap [S,S'-(2-dimethylaminotrimethylene)bisthiocarbamate], Thiocyclam [N,N-dimethyl-1,2,3-trithian-5-ylamine] and Bensultap [S,S'-2-dimethylaminotrimethylene di(benzenethiosulfonate)], N-cyanoamidine derivatives such as N-cyano-N'-methyl-N'-(6-chloro-3-pyridylmethyl)acetoamidine, chlorinated hydrocarbons such as Endosulfan [6,7,8,9,10,10-hexachloro-1,5,5a,6,9,9a-hexahydro-6,9-methanobenzo[e]-2,4,3-dioxathiepin 3-oxide], γ-BHC [1,2,3,4,5,6-hexachlorocyclohexane], 1,1-bis(chlorophenyl)-2,2,2-trichloroethanol, benzoylphenylurea compounds such as Chlorofluazuron [1-(3,5-dichloro-4-(3-chloro-5-trifluoromethylpyrid-2-yloxy)phenyl)-3-(2,6-difluorobenzoyl)urea], Teflubenzuron [I-(3,5-dichloro-2,4-difluorophenyl)-3-(2,6-difluorobenzoyl)urea] and Fulphenoxron [1-(4-(2-chloro-4-trifluoromethylphenoxy)-2-fluorophenyl)-3-(2,6-difluorobenzoyl)urea], formamidine derivatives such as Amitraz [N'-(2,4-dimethylphenyl)-N-((2,4-dimethylphenyl)imino)methyl)-N-methylmethanimidamide] and Chlordimeform [N'-(4-chloro-2-methylphenyl)-N,N-dimethylmethanimidamide], thiourea derivatives such as Diafenthiuron [N-(2,6-diisopropyl-4-phenoxyphenyl)-N'-t-butylthiourea]; Fipronyl (5-amino-1-(2,6-dichloro-α,α,α-trifluoro-p-tolyl)-4-trifluoromethylsulfinylpyrazole-3-carbonitrite, Bromopropylate [isopropyl 4,4'-dibromobenzilate], Tetradifon [2,4,4',5-tetrachlorodiphenyl sulfone], Quinomethionate [6-methyl-2-oxo-1,3-dithiolo-(4,5-b)quinoxaline], Propargite [2-(4-(1,1-dimethylethyl)phenoxy)cyclohexyl-2-propynyl sulfite], Fenbutatin oxide [bis(tris(2-methyl-2-phenylpropyl)tin)oxide], Hexythiazox [(4RS,5RS)-5-(4-chlorophenyl)-N-chlorohexyl-4-methyl-2-oxo-1,3-thiazolidine-3-carboxamide], Chlofentezine [3,6-bis(2-chlorophenyl)-1,2,4,5-tetrazine], Pyridathioben [2-t-butyl-5-(4-t-butylbenzylthio)-4-chloropyridazin-3(2H)-one], Phenpyroxymate [t-butyl(E)-4-((1,3-dimethyl-5-phenoxypyrazol-4-yl)methyleneaminooxymethyl) benzoate], Debphenpyrad [N-4-t-butylbenzyl)-4-chloro-3-ethyl-1-methyl-5-pyrazol carboxamide], polynactin complexes including tetranactin, trinactin and dinactin; Milbemectin, Avermectin, Ivermectin, Azadilactin [AZAD] and Pyrimidifen [5-chloro-N-(2-(4-(2-ethoxyethyl)-2,3-dimethylphenoxy)ethyl)-6-ethylpyrimidine-4-amine].

When the dihalopropene compound of the present invention is applied as an active ingredient of insecticides, nematocides or acaricides for agricultural use, the amount for application is usually 0.1 to 100 g or more, preferably 10 to 100 g per 1000 m$^2$. When emulsifiable concentrates, wettable powders or flowable concentrates of the present compound are diluted with water, the concentration for application is 0.1 to 500 ppm. Granules and dusts are used without any dilution. When the dihalopropene compound of the present invention is applied as an active ingredient of insecticides or acaricides for domestic use, the emulsifiable concentrates, wettable powders, flowable concentrates and emulsifiable concentrates are diluted, for example, with water to a concentration of 0.1 to 500 ppm. Oil sprays, aerosols, fumigants, ULV agents and poisonous baits are used without any dilution, The amount and concentration for application may be changed optionally according to the type of the formulation used, time, place and method of application, the type of noxious organisms and the damage.

The present invention will be further illustrated by the following Examples, Formulation Examples and Biological Test Examples, which are not to be construed to limit thereof.

The following will describe some examples of the dihalopropene compound of the present invention.

EXAMPLE 1

Production of compound 208 by production process A

To a mixture of 93 mg of 3,5-dichloro-4-(3-chloro-5-trifluoromethyl-2-pyridyloxy)phenol, 40 mg of potassium carbonate and 10 ml of N,N-dimethylformamide, a solution prepared by dissolving 42 mg of 1,1,3-trichloro-1-propene in 3 ml of N,N-dimethylformamide was added dropwise at room temperature with stirring. After stirring at room temperature for 5 hours, the reaction solution was poured into ice-water, and extracted twice with 40 ml of diethyl ether. Then, the ether layers were combined, washed with water, dried over anhydrous magnesium sulfate and concentrated to give a crude product. This crude product was subjected to silica gel chromatography to give 96 mg of 3,5-dichloro-4-(3-chloro-5-trifluoromethyl-2-pyridyloxy)-1-(3,3-dichloro-2-propenyloxy)benzene, yield 79%; m.p., 97.8° C.

EXAMPLE 2

Production of compound 1 by production process A

To a mixture of 0.65 g of 3-ethyl-4-(4-isopropoxyphenoxy)phenol, 0.35 g of potassium carbonate and 10 ml of N,N-dimethylformamide, a solution prepared by dissolving 0.73 g of 1,1,3-tribromo-1-propene in 5 ml of N,N-dimethylformamide was added dropwise at room temperature with stirring. After stirring at room temperature for 12 hours, the reaction solution was poured into ice-water, and extracted twice with 50 ml of diethyl ether. Then, the ether layers were combined, washed with water, dried over anhydrous magnesium sulfate and then concentrated to give a crude product. This crude product was subjected to silica gel chromatography to give 0.80 g of 3-ethyl-4-(4-isopropoxyphenoxy)-1-(3,3-dibromo-2-propenyloxy)benzene, yield 71%: $n_D^{23.0}$ 1.5761.

EXAMPLE 3

Production of compound 130 by production process A

To a solution prepared by dissolving 0.44 g of 2-trifluoromethyl-4-(3-ethoxyphenoxy)phenol in 10 ml of N,N-dimethylformamide, 0.062 g of sodium hydride (60% oil-based) was added with stirring under ice cooling. After 10 minutes, a solution prepared by dissolving 0.24 g of 1,1,3-trichloro-1-propene in 5 ml of N,N-dimethylformamide was added dropwise under ice cooling. After stirring at room temperature for 10 hours, the reaction solution was poured into ice-water, and extracted twice with 50 ml of diethyl ether. Then, the ether layers were combined, washed with water, dried over anhydrous magnesium sulfate and concentrated to give a crude product. This crude product was subjected to silica gel chromatography to give 0.37 g of 2-trifluoromethyl-4-(3-ethoxyphenoxy)-1-(3,3-dichloro-2-propenyloxy)benzene, yield 62%; $n_D^{23.6}$ 1.5369.

EXAMPLE 4

Production of compound 206 by production process A

To a mixture of 0.77 g of 2,5-dichloro-4-(3-bromo-5-trifluoromethyl-2-pyridyloxy)phenol, 0.29 g of potassium carbonate and 20 ml of N,N-dimethylformamide, a solution prepared by dissolving 0.31 g of 1,1,3-trichloropropene in 5 ml of N,N-dimethylformamide was added dropwise at room temperature with stirring. After stirring at room temperature for 10 hours, the reaction solution was poured into ice-water, and extracted twice with 50 ml of ethyl acetate. Then, the ethyl acetate layers were combined, washed with water, dried over anhydrous magnesium sulfate and then concentrated to give a crude product. This crude product was subjected to silica gel chromatography to give 0.81 g of 2,5-dichloro-4-(3-bromo-5-trifluoromethyl-2-pyridyloxy)-1-(3,3-dichloro-2-propenyloxy)benzene, yield 83%; m.p., 95.4° C.

EXAMPLE 5

Production of compound 273 by production process A

To a mixture of 0.59 g of 2-bromo-4-(4-chlorophenylthio)phenol, 0.28 g of potassium carbonate and 20 ml of N,N-dimethylformamide, a solution prepared by dissolving 0.30 g of 1,1,3-trichloropropene in 5 ml of N,N-dimethylformamide was added dropwise at room temperature with stirring. After the mixture was stirred at room temperature for 6 hours, the reaction solution was poured into ice-water, and extracted twice with 50 ml of diethyl ether. Then, the ether layers were combined, washed with water, dried over anhydrous magnesium sulfate and then concentrated to give a crude product. This crude product was subjected to silica gel column chromatography to give 0.62 g of 2-bromo-4-(4-chlorophenylthio)-1-(3,3-dichloro-2-propenyloxy)benzene, yield 78%; $n_D^{25.0}$ 1.6514.

EXAMPLE 6

Production of compound 275 by production process B

To a solution prepared by dissolving 0.65 g of 2-bromo-4-(1-methyl-1-(4-ethoxyphenyl))ethylphenol, 0.25 g of 3,3-dichloroallyl alcohol and 0.51 g of triphenylphosphine in 10 ml of tetrahydrofuran, a solution prepared by dissolving 0.34 g of diethylazodicarboxylate in 5 ml of tetrahydrofuran was added dropwise at room temperature with stirring. After stirring at room temperature for 24 hours, the reaction solution was concentrated to give a residue. This residue was subjected to silica gel chromatography to give 0.28 g of 2-bromo-4-(1-methyl-1-(4-ethoxyphenyl))ethyl-1-(3,3-dichloro-2-propenyloxy)benzene, yield 32%; $n_D^{25.0}$ 1.5869.

EXAMPLE 7

Production of compound 196 by production process B

To a solution prepared by dissolving 0.55 g of 2-trifluoromethyl-4-(4-ethoxyphenoxy)phenol, 0.40 g of 3,3-dibromoallyl alcohol and 0.49 g of triphenylphosphine in 10 ml of tetrahydrofuran, a solution prepared by dissolving 0.38 g of diisopropylazodicarboxylate in 5 ml of tetrahydrofuran was added dropwise at room temperature with stirring. After stirring at room temperature for 12 hours, the reaction solution was concentrated. Then, 20 ml of diethyl ether was added thereto, and the precipitate was filtered off. The resulting filtrate was concentrated, and subjected to silica gel column chromatography to give 0.30 g of 2-trifluoromethyl-4-(4-ethoxyphenoxy)-1-(3,3-dibromo-2-propenyloxy)benzene, yield 32%; $n_D^{24.0}$ 1.5480.

Example 8

Production of compound 68 by production process C

First, 0.38 g of zinc dust, 1.54 g of triphenylphosphine, 1.94 g of carbon tetrabromide and 20 ml of methylene chloride were charged into a reaction vessel, and stirred at room temperature. After 24 hours, a solution prepared by dissolving 1.0 g of (2-bromo-4-(3-chlorophenoxy) phenoxy) acetaldehyde in 5 ml of methylene chloride was added dropwise to the solution with stirring. After stirring at room temperature for 6 hours, the reaction solution was concentrated to give a residue. This residue was subjected to silica gel column chromatography to give 0.48 g of 2-bromo-4-(3-chlorophenoxy)-1-(3,3-dibromo-2-propenyloxy) benzene, yield 33%; $n_D^{24.0}$ 1.6282.

EXAMPLE 9

Production of compound 212 by production process A

To a mixture of 0.56 g, of 3,5-dichloro-4-(3,5-bistrifluoromethyl-2-pyridyloxy)phenol, 0.22 g of potassium carbonate and 20 ml of N,N-dimethylformamide, a solution prepared by dissolving 0.23 g of 1,1,3-trichloro-1-propene in 5 ml of N,N-dimethylformamide was added dropwise at room temperature with stirring. After stirring at room temperature for 7 hours, the reaction solution was poured into ice-water, and extracted twice with 50 ml of diethyl ether. Then, the ether layers were combined, washed with water, dried over anhydrous magnesium sulfate and then concentrated to give a crude product. This crude product was subjected to silica gel chromatography to give 0.50 g of 3,5-dichloro-4-(3,5-bistrifluoromethyl-2-pyridyloxy)-2-(3,3-dichloro-2-propenyloxy)benzene, yield 70%; m.p., 78.2° C.

EXAMPLE 10

Production of compound 210 by production process A

To a mixture of 0.83 g of 3,5-dichloro-4-(3-bromo-5-trifluoromethyl-2-pyridyloxy)phenol, 0.31 g of potassium carbonate and 20 ml of N-dimethylformamide, a solution prepared by dissolving 0.33 g of 1,1,3-trichloro-1-propene in 5 ml of N,N-dimethylformamide was added dropwise at room temperature with stirring. After stirring at room temperature for 7 hours, the reaction solution was poured into ice-water, and extracted twice with 50 mi of diethyl ether. Then, the ether layers were combined, washed with water, dried over anhydrous magnesium sulfate and then concentrated to give a crude product. This crude product was subjected to silica gel chromatography to give 0.79 g of 3,5-dichloro-4-(3-bromo-5-trifluoromethyl-2-pyridyloxy)-2-(3,3-dichloro-2-propenyloxy)benzene, yield 75%; m.p., 90.7° C.

Other examples of the dihalopropene compound of the present invention will be described along with their compound numbers.

(1) 3-Ethyl-4-(4-isopropoxyphenoxy)-1-(3,3-dibromo-2-propenyloxy)benzene, $n_D^{23.0}$ 1.5761
(2) 2-Isopropyl-4-(3-phenylphenoxy)-1-(3,3-dichloro-2-propenyloxy)benzene, $n_D^{25.0}$ 1.6035
(3) 2-Isopropyl-4-(3-phenylphenoxy)-1-(3,3-dibromo-2-propenyloxy)benzene, $n_D^{25.0}$ 1.6223
(4) 2-Isopropyl-4-(2,4-diisopropylphenoxy)-1-(3,3-dichloro-2-propenyloxy)benzene, $n_D^{24.5}$ 1.5467
(5) 2-Isopropyl-4-(2,4-isopropylphenoxy)-1-(3,3-dibromo-2-propenyloxy)benzene, $n_D^{24.5}$ 1.5646
(6) 2-Phenyl-4-(4-isopropoxyphenoxy)-1-(3,3-dichloro-2-propenyloxy)benzene, $n_D^{23.0}$ 1.5966
(7) 2-Phenyl-4-(4-isopropoxyphenoxy)-1-(3,3-dibromo-2-propenyloxy)benzene, $n_D^{23.0}$ 1.6141
(8) 2-Isopropyl-4-(4-phenoxyphenoxy)-1-(3,3-dichloro-2-propenyloxy)benzene, $n_D^{23.0}$ 1.5887
(9) 2-Isopropyl-4-(4-phenoxyphenoxy)-1-(3,3-dibromo-2-propenyloxy)benzene, $n_D^{23.0}$ 1.6068
(10) 2-Allyl-4-(4-isopropoxyphenoxy)-1-(3,3-dichloro-2-propenyloxy)benzene, $n_D^{23.0}$ 5638
(11) 2-Allyl-4-(4-isopropoxyphenoxy)-1-(3,3-dibromo-2-propenyloxy)benzene, $n_D^{23.0}$ 1.5836
(12) 2-n-Propyl-4-(3-isopropoxyphenoxy)-1-(3,3-dibromo-2-propenyloxy)benzene, $n_D^{23.0}$ 1.5771
(13) 3-Isopropyl-4-(4-isopropoxyphenoxy)-1-(3,3-dichloro-2-propenyloxy)benzene, $n_D^{22.0}$ 1.5544
(14) 3-Isopropyl-4-(3-isopropoxyphenoxy)-1-(3,3-dibromo-2-propenyloxy)benzene, $n_D^{22.0}$ 1.5753
(15) 5-Isopropyl-2-n-propyl-4-(4-ethoxyphenoxy)-1-(3,3-dibromo-2-propenyloxy)benzene, m.p., 51° C.
(16) 2-n-Propyl-4-(4-cyclohexylphenoxy)-1-(3,3-dichloro-2-propenyloxy)benzene, $n_D^{22.0}$ 1.5671
(17) 2-n-Propyl-4-(4-cyclohexylphenoxy)-1-(3,3-dibromo-2-propenyloxy)benzene, m.p., 49.8° C.
(18) 3-Methyl-4-(4-isopropoxyphenoxy)-1-(3,3-dichloro-2-propenyloxy)benzene, $n_D^{23.5}$ 1.5623
(19) 3-Methyl-4-(4-isopropoxyphenoxy)-1-(3,3-dibromo-2-propenyloxy)benzene, $n_D^{23.5}$ 1.5834
(20) 2-n-Propyl-4-(3-phenylphenoxy)-1-(3,3-dichloro-2-propenyloxy)benzene, $n_D^{23.0}$ 1.6059
(21) 2-n-Propyl-4-(3-phenylphenoxy)-1-(3,3-dibromo-2-propenyloxy)benzene, $n_D^{23.0}$ 1.6244
(22) 3-Ethyl-4-(4-isopropoxyphenoxy)-1-(3,3-dichloro-2-propenyloxy)benzene, $n_D^{23.0}$ 1.5575
(23) 2-Methyl-4-(4-ethoxyphenoxy)-1-(3,3-dibromo-2-propenyloxy)benzene, $n_D^{22.5}$ 1.5961
(24) 2-Allyl-4-(4-ethoxyphenoxy)-1-(3,3-dibromo-2-propenyloxy)benzene, $n_D^{21.5}$ 1.5884
(25) 2-Isopropyl-4-(4-isopropoxyphenoxy)-1-(3,3-dichloro-2-propenyloxy)benzene, $n_D^{21.5}$ 1.5567
(26) 2-Isopropyl-4-(4-isopropoxyphenoxy)-1-(3,3-dibromo-2-propenyloxy)benzene, $n_D^{21.5}$ 1.5774
(27) 2-Isopropyl-4-(3-methoxyphenoxy)-1-(3,3-dichloro-2-propenyloxy)benzene, $n_D^{21.5}$ 1.5704
(28) 2-Isopropyl-4-(3-methoxyphenoxy)-1-(3,3-dibromo-2-propenyloxy)benzene, $n_D^{21.5}$ 1.5928
(29) 2-Tert-butyl-5-methyl-4-(4-ethoxyphenoxy)-1-(3,3-dichloro-2-propenyloxy)benzene, $n_D^{18.5}$ 1.5584
(30) 2-Tert-butyl-5-methyl-4-(4-ethoxyphenoxy)-1-(3,3-dibromo-2-propenyloxy)benzene, $n_D^{18.5}$ 1.5781
(31) 3-Isopropyl-4-(4-ethoxyphenoxy)-1-(3,3-dichloro-2-propenyloxy)benzene, $n_D^{23.0}$ 1.5625
(32) 3-Isopropyl-4-(4-ethoxyphenoxy)-1-(3,3-dibromo-2-propenyloxy)benzene, $n_D^{23.0}$ 1.5825
(33) 2-n-Propyl-4-(3-isopropoxyphenoxy)-1-(3,3-dichloro-2-propenyloxy)benzene, $n_D^{23.0}$ 1.5570
(34) 2,6-Dimethyl-4-(4-chlorophenoxy)-1-(3,3-dichloro2-propenyloxy)benzene, $n_D^{22.5}$ 1.5784
(35) 2,6-Dimethyl-4-(4-chlorophenoxy)-1-(3,3-dibromo-2-propenyloxy)benzene, $n_D^{22.5}$ 1.5970
(36) 2-Isopropyl-4-(4-ethoxyphenoxy)-1-(3,3-dichloro-2-propenyloxy)benzene, $n_D^{22.5}$ 1.5616
(37) 2-Isopropyl-4-(4-ethoxyphenoxy)-1-(3,3-dibromo-2-propenyloxy)benzene, $n_D^{22.5}$ 1.5787
(38) 2-Tert-butyl-4-(4-ethoxyphenoxy)-1-(3,3-dichloro-2-propenyloxy)benzene, $n_D^{23.0}$ 1.5601
(39) 2-Tert-butyl-4-(4-ethoxyphenoxy)-1-(3,3-dibromo-2-propenyloxy)benzene, $n_D^{23.0}$ 1.5809
(40) 2-Isopropyl-4-(4-ethoxyphenoxy)-1-(3,3-dibromo-2-propenyloxy)benzene, $n_D^{23.0}$ 1.5681
(41) 2-Isopropyl-4-(4-ethoxyphenoxy)-1-(3,3-dibromo-2-propenyloxy)benzene, $n_D^{23.0}$ 1.5900
(42) 2-Isopropyl-4-(2-chloro-4-ethoxyphenoxy)-1-(3,3-dichloro-2-propenyloxy)benzene, $n_D^{24.5}$ 1.5664
(43) 2-Isopropyl-4-(2-chloro-4-ethoxyphenoxy)-1-(3,3-dibromo-2-propenyloxy)benzene, $n_D^{24.5}$ 1.5874
(44) 2-Ethyl-4-(4-ethoxyphenoxy)-1-(3,3-dichloro-2-propenyloxy)benzene, $n_D^{22.5}$ 1.5741
(45) 2-Isopropyl-4-(3-chlorophenoxy)-1-(3,3-dichloro-2-propenyloxy)benzene, $n_D^{24.5}$ 1.5700
(46) 2,6-Diisopropyl-4-(3-chlorophenoxy)-1-(3,3-dichloro-2-propenyloxy)benzene, $n_D^{24.5}$ 1.5530
(47) 2-Isopropyl-4-(3-chlorophenoxy)-1-(3,3-dibromo-2-propenyloxy)benzene, $n_D^{24.5}$ 1.5961
(48) 2-Ethyl-4-(4-chlorophenoxy)-1-(3,3-dichloro-2-propenyloxy)benzene, $n_D^{25.0}$ 1.5821
(49) 2-Ethyl-4-(4-ethoxyphenoxy)-1-(3,3-dichloro-2-propenyloxy)benzene, $n_D^{22.0}$ 1.5701
(50) 2-Ethyl-4-(4-ethoxyphenoxy)-1-(3,3-dibromo-2-propenyloxy)benzene, $n_D^{22.0}$ 1.5912
(51) 2-n-Propyl-4-(4-ethoxyphenoxy)-1-(3,3-dichloro-2-propenyloxy)benzene, $n_D^{23.5}$ 1.5615
(52) 2-n-Propyl-4-(4-ethoxyphenoxy)-1-(3,3-dibromo-2-propenyloxy)benzene, $n_D^{23.0}$ 1.5849
(53) 3-Sec-butyl-4-(4-ethoxyphenoxy)-1-(3,3-dichloro-2-propenyloxy)benzene, $n_D^{23.5}$ 1.5572
(54) 2-Sec-butyl-4-(4-ethoxyphenoxy)-1-(3,3-dibromo-2-propenyloxy)benzene, $n_D^{23.0}$ 1.5784
(55) 3-Methyl-4-(4-methoxyphenoxy)-1-(3,3-dibromo-2-propenyloxy)benzene, $n_D^{24.5}$ 1.5788
(56) 3-Methyl-4-(4-methoxyphenoxy)-1-(3,3-dibromo-2-propenyloxy)benzene, $n_D^{24.5}$ 1.6018
(57) 3-Methyl-4-(4-ethoxyphenoxy)-1-(3,3-dichloro-2-propenyloxy)benzene, $n_D^{25.0}$ 1.5705
(58) 3-Methyl-4-(4-ethoxyphenoxy)-1-(3,3-dibromo-2-propenyloxy)benzene, $n_D^{25.0}$ 1.5930
(59) 2-Bromo-4-(3-chlorophenoxy)-1-(3,3-dichloro-2-propenyloxy)benzene, m.p. 42.7° C.
(60) 2-Bromo-4-(2-chloro-4-trifluoromethylphenoxy)-1-(3,3-dichloro-2-propenyloxy)benzene, $n_D^{24.3}$ 1.5546
(61) 2-Bromo-4-(3-bromophenoxy)-1-(3,3-dichloro-2-propenyloxy)benzene, $n_D^{22.5}$ 1.6202

(62) 2-Bromo-4-(3,5-dichlorophenoxy)-1-(3,3-dichloro-2-propenyloxy)benzene, $n_D^{22.5}$ 1.5950

(63) 2-Bromo-4-(4-chlorophenoxy)-1-(3,3-dichloro-2-propenyloxy)benzene, $n_D^{24.0}$ 1.6110

(64) 2-Bromo-4-(4-trifluoromethylphenoxy)-1-(3,3-dichloro-2-propenyloxy)benzene, $n_D^{25.0}$ 1.5616

(65) 2-Bromo-4-(2-chloro-4-trifluoromethylphenoxy)-1-(3,3-dibromo-2-propenyloxy)benzene, $n_D^{25.5}$ 1.5892

(66) 2-Bromo-4-(3-bromophenoxy)-1-(3,3-dibromo-2-propenyloxy)benzene, $n_D^{23.0}$ 1.6496

(67) 2-Bromo-4-(3,5-dichlorophenoxy)-1-(3,3-dibromo-2-propenyloxy)benzene, $n_D^{23.0}$ 1.6398

(68) 2-Bromo-4-(3-chlorophenoxy)-1-(3,3-dibromo-2-propenyloxy)benzene, $n_D^{24.0}$ 1.6282

(69) 2-Bromo-4-(3-bromo-4-(3,3-dichloro-2-propenyloxyphenoxy)-1-(3,3-dichloro-2-propenyloxy)benzene, $n_D^{24.2}$ 1.6208

(70) 2-Chloro-4-(3,4-dichlorophenoxy)-1-(3,3-dichloro-2-propenyloxy)benzene, $n_D^{23.0}$ 1.5820

(71) 2-Chloro-4-(2,4-dichlorophenoxy)-1-(3,3-dichloro-2-propenyloxy)benzene, $n_D^{22.0}$ 1.6060

(72) 2-Chloro-4-(2,4-difluorophenoxy)-1-(3,3-dibromo-2-propenyloxy)benzene, $n_D^{22.0}$ 1.5642

(73) 2-Chloro-4-(4-fluorophenoxy)-1-(3,3-dichloro-2-propenyloxy)benzene, $n_D^{22.0}$ 1.5802

(74) 2-Chloro-4-(3-chlorophenoxy)-1-(3,3-dibromo-2-propenyloxy)benzene, $n_D^{24.2}$ 1.6248

(75) 2-Chloro-4-(3-fluorophenoxy)-1-(3,3-dichloro-2-propenyloxy)benzene, $n_D^{24.0}$ 1.5728

(76) 2,5-Dichloro-4-(4-(3,3-dichloro-2-propenyloxy)phenoxy)-1-(3,3-dichloro-2-propenyloxy)benzene, $n_D^{23.4}$ 1.5998

(77) 2,5-Dichloro-4-(4-isopropoxyphenoxy)-1-(3,3-dichloro-2-propenyloxy)benzene, $n_D^{24.5}$ 1.5828

(78) 2,5-Dichloro-4-(4-isopropoxyphenoxy)-1-(3,3-dibromo-2-propenyloxy)benzene, $n_D^{24.5}$ 1.6021

(79) 2,6-Dichloro-4-(3-chlorophenoxy)-1-(3,3-dichloro-2-propenyloxy)benzene, $n_D^{24.2}$ 1.6003

(80) 2,6-Dichloro-4-(3,4-dichlorophenoxy)-1-(3,3-dichloro-2-propenyloxy)benzene, $n_D^{24.2}$ 1.5992

(81) 2,6-Dichloro-4-(3,5-difluorophenoxy)-1-(3,3-dichloro-2-propenyloxy)benzene, $n_D^{24.9}$ 1.5689

(82) 2,6-Dichloro-4-(4-chlorophenoxy)-1-(3,3-dichloro-2-propenyloxy)benzene, $n_D^{24.0}$ 1.5962

(83) 2,6-Dichloro-4-(3-fluorophenoxy)-1-(3,3-dichloro-2-propenyloxy)benzene, $n_D^{24.0}$ 1.5800

(84) 2,6-Dichloro-4-(2-chloro-4-trifluoromethylphenoxy)-1-(3,3-dichloro-2-propenyloxy)benzene, $n_D^{24.3}$ 1.5546

(85) 2,6-Dichloro-4-(3,4-dichlorophenoxy)-1-(3,3-dibromo-2-propenyloxy)benzene, $n_D^{24.0}$ 1.6275

(86) 2,5-Dichloro-4-(4-chlorophenoxy)-1-(3,3-dibromo-2-propenyloxy)benzene, $n_D^{24.0}$ 1.6154

(87) 2,5-Dichloro-4-(2,6-dichloro-4-trifluoromethylphenoxy)-1-(3,3-dichloro-2-propenyloxy)benzene, m.p., 86.1° C.

(88) 2,5-Dichloro-4-(2,6-dichloro-4-trifluoromethylphenoxy)-1-(3,3-dibromo-2-propenyloxy)benzene, m.p., 86.9° C.

(89) 2-Chloro-4-(2-chloro-4-trifluoromethylphenoxy)-1-(3,3-dichloro-2-propenyloxy)benzene, $n_D^{23.6}$ 1.5581

(90) 2-Bromo-4-(3-bromo-4-(3,3-dibromo-2-propenyloxy)phenoxy)-1-(3,3-dibromo-2-propenyloxy)benzene, m.p., 80.6° C.

(91) 2-Chloro-4-(4-chlorophenoxy)-1-(3,3-dichloro-2-propenyloxy)benzene, $n_D^{24.0}$ 1.5970

(92) 2-Chloro-4-(3-bromophenoxy)-1-(3,3-dichloro-2-propenyloxy)benzene, $n_D^{21.5}$ 1.6112

(93) 2-Chloro-4-(3,5-dichlorophenoxy)-1-(3,3-dichloro-2-propenyloxy)benzene, $n_D^{21.5}$ 1.6045

(94) 2-Chloro-4-(3,5-dichlorophenoxy)-1-(3,3-dibromo-2-propenyloxy)-benzene, $n_D^{25.5}$ 1.6198

(95) 2-Chloro-4-(3-bromophenoxy)-1-(3,3-dibromo-2-propenyloxy)benzene, $n_D^{25.5}$ 1.6365

(96) 2-Chloro-4-(2-chloro-4-trifluoromethylphenoxy)-1-(3,3-dibromo-2-propenyloxy)benzene, $n_D^{23.0}$ 1.5810

(97) 2-Chloro-4-(4-chlorophenoxy)-1-(3,3-dibromo-2-propenyloxy)benzene, $n_D^{24.0}$ 1.6232

(98) 2-Chloro-4-(3,5-difluorophenoxy)-1-(3,3-dichloro-2-propenyloxy)benzene, $n_D^{24.2}$ 1.5691

(99) 2-Chloro-4-(3-chlorophenoxy)-1-(3,3-dichloro-2-propenyloxy)benzene, m.p., 48.8° C.

(100) 2-Chloro-4-(3-methylphenoxy)-1-(3,3-dichloro-2-propenyloxy)benzene, $n_D^{23.8}$ 1.5830

(101) 2-Chloro-4-(4-methylphenoxy)-1-(3,3-dichloro-2-propenyloxy)benzene, $n_D^{23.8}$ 1.5835

(102) 2-Bromo-6-chloro-4-(3-chlorophenoxy)-1-(3,3-dichloro-2-propenyloxy)benzene, $n_D^{24.0}$ 1.6139

(103) 2-Bromo-6-chloro-4-(3-chloro-5-trifluoromethyl-2-pyridyloxy)-1-(3,3-dichloro-2-propenyloxy)benzene, m.p., 59.5° C.

(104) 2-Bromo-6-chloro-4-(3,4-dichlorophenoxy)-1-(3,3-dichloro-2-propenyloxy)benzene, $n_D^{22.0}$ 1.6198

(105) 2-Bromo-6-chloro-4-(3,4-dichlorophenoxy)-1-(3,3-dibromo-2-propenyloxy)benzene, $n_D^{24.0}$ 1.6395

(106) 2-Chloro-5-methyl-4-(4-(2,2,2-trifluoroethoxy)phenoxy)-1-(3,3-dichloro-2-propenyloxy)benzene, m.p., 55.4° C.

(107) 2-Chloro-5-methyl-4-(4-(2,2,2-trifluoroethoxy)phenoxy)-1-(3,3-dibromo-2-propenyloxy)benzene, $n_D^{24.2}$ 1.5645

(108) 2-Chloro-5-methyl-4-(4-isopropoxyphenoxy)-1-(3,3-dichloro-2-propenyloxy)benzene, $n_D^{23.5}$ 1.5723

(109) 2-Chloro-5-methyl-4-(4-isopropoxyphenoxy)-1-(3,3-dibromo-2-propenyloxy)benzene, $n_D^{23.5}$ 1.5929

(110) 2-Bromo-4-(4-isopropoxyphenoxy)-1-(3,3-dichloro-2-propenyloxy)benzene, $n_D^{23.5}$ 1.5836

(111) 2-Bromo-4-(4-isopropoxyphenoxy)-1-(3,3-dibromo-2-propenyloxy)benzene, $n_D^{23.5}$ 1.6043

(112) 2-Trifluoromethyl-4-(4-methoxyphenylthio)-1-(3,3-dibromo-2-propenyloxy)benzene, $n_D^{24.5}$ 1.5719

(113) 2,5-Dichloro-4-(2,4-bistrifluoromethylphenoxy)-1-(3,3-dichloro-2-propenyloxy)benzene, m.p., 78.5° C.

(114) 2,5-Dichloro-4-(2,4-bistrifluoromethylphenoxy)-1-(3,3-dibromo-2-propenyloxy)benzene, m.p., 74.3° C.

(115) 2-Difluoromethyl-4-(3-chlorophenoxy)-1-(3,3-dichloro-2-propenyloxy)benzene, $n_D^{23.5}$ 1.5632

(116) 2-Methoxyiminomethyl-4-(4-isopropoxyphenoxy)-1-(3,3-dibromo-2-propenyloxy)benzene, $n_D^{24.5}$ 1.5966

(117) 2-Methoxymethyl-4-(4-isopropoxyphenoxy)-1-(3,3-dibromo-2-propenyloxy)benzene, $n_D^{25.0}$ 1.5793

(118) 2-(2,2-Dibromoethynyl)-4-(4-isopropoxyphenoxy)-1-(3,3-dichloro-2-propenyloxy)benzene, $n_D^{25.0}$ 1.6102

(119) 2-(2,2-Dibromoethynyl)-4-(4-isopropoxyphenoxy)-1-(3,3-dibromo-2-propenyloxy)benzene, $n_D^{24.0}$ 1.6290

(120) 2-Ethynyl-4-(4-isopropoxyphenoxy)-1-(3,3-dibromo-2-propenyloxy)benzene, $n_D^{23.5}$ 1.6037

(121) 2-Difluoromethyl-4-(4-isopropoxyphenoxy)-1-(3,3-dichloro-2-propenyloxy)benzene, $n_D^{22.5}$ 1.5461

(122) 2-Difluoromethyl-4-(4-isopropoxyphenoxy)-1-(3,3-dibromo-2-propenyloxy)benzene, $n_D^{22.5}$ 1.5677

(123) 2-Dibromo-6-nitro-4-(4-isopropoxyphenoxy)-1-(3,3-dibromo-2-propenyloxy)benzene, $n_D^{23.0}$ 1.6086

(124) 2-Trifluoromethyl-4-(4-methoxyphenoxy)-1-(3,3-dibromo-2-propenyloxy)benzene, $n_D^{25.4}$ 1.5572

(125) 2-Trifluoromethyl-4-(3-trifluoromethylphenoxy)-1-(3,3-dibromo-2-propenyloxy)benzene, $n_D^{24.0}$ 1.5282

(126) 2-Trifluoromethyl-4-((4-methylthio)phenoxy)-1-(3,3-dichloro-2-propenyloxy)benzene, $n_D^{24.2}$ 1.5722

(127) 2-Trifluoromethyl-4-((4-methylthio)phenoxy)-1-(3,3-dibromo-2-propenyloxy)benzene, $n_D^{24.2}$ 1.5944

(128) 2-Trifluoromethyl-4-(3-methoxyphenoxy)-1-(3,3-dichloro-2-propenyloxy)benzene, $n_D^{23.6}$ 1.5418

(129) 2-Trifluoromethyl-4-(3-methoxyphenoxy)-1-(3,3-dibromo-2-propenyloxy)benzene, $n_D^{23.6}$ 1.5640

(130) 2-Trifluoromethyl-4-(3-ethoxyphenoxy)-1-(3,3-dichloro-2-propenyloxy)benzene, $n_D^{23.6}$ 1.5369

(131) 2-Trifluoromethyl-4-(3-ethoxyphenoxy)-1-(3,3-dibromo-2-propenyloxy)benzene, $n_D^{23.6}$ 1.5550

(132) 2-Trifluoromethyl-4-(3,5-dimethoxyphenoxy)-1-(3,3-dichloro-2-propenyloxy)benzene, m.p., 46.0° C.

(133) 2-Trifluoromethyl-4-(3,5-dimethylphenoxy)-1-(3,3-dibromo-2-propenyloxy)benzene, $n_D^{24.2}$ 1.5670

(134) 2-Trifluoromethyl-4-(3,4-dimethoxyphenoxy)-1-(3,3-dichloro-2-propenyloxy)benzene, $n_D^{24.2}$ 1.5670

(135) 2-Trifluoromethyl-4-(3,4-dimethoxyphenoxy)-1-(3,3-dibromo-2-propenyloxy)benzene, m.p., 76.1° C.

(136) 2-Trifluoromethyl-4-(2-chloro-4-ethoxyphenoxy)-1-(3,3-dibromo-2-propenyloxy)benzene, $n_D^{24.2}$ 1.5260

(137) 2-Trifluoromethyl-4-(4-n-propoxyphenoxy)-1-(3,3-dichloro-2-propenyloxy)benzene, $n_D^{24.2}$ 1.5399

(138) 2-Trifluoromethyl-4-(4-n-propoxyphenoxy)-1-(3,3-dibromo-2-propenyloxy)benzene, $n_D^{24.2}$ 1.5552

(139) 2-Trifluoromethyl-4-(4-isopropoxyphenoxy)-1-(3,3-dichloro-2-propenyloxy)benzene, $n_D^{24.2}$ 1.5322

(140) 2-Trifluoromethyl-4-(4-isopropoxyphenoxy)-1-(3,3-dibromo-2-propenyloxy)benzene, $n_D^{24.2}$ 1.5429

(141) 2-Trifluoromethyl-4-(4-n-butoxyphenoxy)-1-(3,3-dichloro-2-propenyloxy)benzene, $n_D^{24.2}$ 1.5302

(142) 2-Trifluoromethyl-4-(4-n-butoxyphenoxy)-1-(3,3-dibromo-2-propenyloxy)benzene, $n_D^{24.2}$ 1.5510

(143) 2-Trifluoromethyl-4-(4-(2,2,2-trifluoroethoxy)phenoxy)-1-(3,3-dichloro-2-propenyloxy)benzene, $n_D^{24.2}$ 1.5095

(144) 2-Trifluoromethyl-4-(4-(2,2,2-trifluoroethoxy)phenoxy)-1-(3,3-dibromo-2-propenyloxy)benzene, $n_D^{24.2}$ 1.5300

(145) 2-Trifluoromethyl-4-(4-phenoxyphenoxy)-1-(3,3-dichloro-2-propenyloxy)benzene, m.p., 49.3° C.

(146) 2-Trifluoromethyl-4-(4-phenoxyphenoxy)-1-(3,3-dibromo-2-propenyloxy)benzene, m.p., 61.9° C.

(147) 2-Trifluoromethyl-4-(4-phenylphenoxy)-1-(3,3-dichloro-2-propenyloxy)benzene, m.p., 59°–63° C.

(148) 2-Trifluoromethyl-4-(4-phenylphenoxy)-1-(3,3-dibromo-2-propenyloxy)benzene, m.p., 61°–62° C.

(149) 2-Trifluoromethyl-4-(3-isopropoxyphenoxy)-1-(3,3-dichloro-2-propenyloxy)benzene, $n_D^{21.6}$ 1.5302

(150) 2-Trifluoromethyl-4-(3-isopropoxyphenoxy)-1-(3,3-dibromo-2-propenyloxy)benzene, $n_D^{21.6}$ 1.5511

(151) 2-Trifluoromethyl-4-(4-cyclohexylphenoxy)-1-(3,3-dichloro-2-propenyloxy)benzene, $n_D^{18.6}$ 1.5416

(152) 2-Trifluoromethyl-4-(4-cyclohexylphenoxy)-1-(3,3-dibromo-2-propenyloxy)benzene, m.p., 71.5° C.

(153) 4-(4-Isopropoxyphenoxy)-1-(3,3-dichloro-2-propenyloxy)-5,6,7,8-tetrahydronaphthalene, $n_D^{18.6}$ 1.5575

(154) 4-(4-Isopropoxyphenoxy)-1-(3,3-dibromo-2-propenyloxy)-5,6,7,8-tetrahydronaphthalene, $n_D^{18.6}$ 1.5812

(155) 2-Trifluoromethyl-4-(2,6-dichloro-4-trifluoromethylphenoxy)-1-(3,3-dichloro-2-propenyloxy)benzene, $n_D^{18.6}$ 1.5220

(156) 2-Trifluoromethyl-4-(2,6-dichloro-4-trifluoromethylphenoxy)-1-(3,3-dibromo-2-propenyloxy)benzene, $n_D^{18.6}$ 1.5402

(157) 2-Trifluoromethyl-4-(4-cyclopentylphenoxy)-1-(3,3-dichloro-2-propenyloxy)benzene, $n_D^{22.5}$ 1.5472

(158) 2-Trifluoromethyl-4-(4-cyclopentylphenoxy)-1-(3,3-dibromo-2-propenyloxy)benzene, $n_D^{20.8}$ 1.5620

(159) 2-Trifluoromethyl-4-(4-(2-n-pentyl)phenoxy)-1-(3,3-dichloro-2-propenyloxy)benzene, $n_D^{24.2}$ 1.5278

(160) 2-Trifluoromethyl-4-(4-(2-n-pentyl)phenoxy)-1-(3,3-dibromo-2-propenyloxy)benzene, $n_D^{24.2}$ 1.5468

(161) 2-Trifluoromethyl-4-(4-tert-pentylphenoxy)-1-(3,3-dichloro-2-propenyloxy)benzene, $n_D^{24.2}$ 1.5308

(162) 2-Trifluoromethyl-4-(4-tert-pentylphenoxy)-1-(3,3-dibromo-2-propenyloxy)benzene, $n_D^{24.2}$ 1.5506

(163) 2-Trifluoromethyl-4-(3-phenylphenoxy)-1-(3,3-dichloro-2-propenyloxy)benzene, $n_D^{23.9}$ 1.5827

(164) 2-Trifluoromethyl-4-(3-phenylphenoxy)-1-(3,3-dibromo-2-propenyloxy)benzene, $n_D^{23.9}$ 1.5999

(165) 2-Trifluoromethyl-4-(3-phenoxyphenoxy)-1-(3,3-dichloro-2-propenyloxy)benzene, $n_D^{23.9}$ 1.5548

(166) 2-Trifluoromethyl-4-(3-phenoxyphenoxy)-1-(3,3-dibromo-2-propenyloxy)benzene, $n_D^{23.9}$ 1.5801

(167) 2-Trifluoromethyl-4-(5,6,7,g-tetrahydro-2-naphthoxy)-1-(3,3-dichloro-2-propenyloxy)benzene, $n_D^{23.9}$ 1.5432

(168) 2-Trifluoromethyl-4-(5,6,7,g-tetrahydro-2-naphthoxy)-1-(3,3-dibromo-2-propenyloxy)benzene, $n_D^{23.9}$ 1.5678

(169) 2-Trifluoromethyl-4-(5-indanoxy)-1-(3,3-dichloro-2-propenyloxy)benzene, $n_D^{23.4}$ 1.5504

(170) 2-Trifluoromethyl-4-(5-indanoxy)-1-(3,3-dibromo-2-propenyloxy)benzene, $n_D^{23.4}$ 1.5692

(171) 2-Trifluoromethyl-4-(3,5-bis(trifluoromethyl)phenoxy)-1-(3,3-dichloro-2-propenyloxy)benzene, $n_D^{23.4}$ 1.4832

(172) 2-Trifluoromethyl-4-(3,5-bis(trifluoromethyl)phenoxy)-1-(3,3-dibromo-2-propenyloxy)benzene, $n_D^{23.0}$ 1.5018

(173) 2-Trifluoromethyl-4-(4-sec-butylphenoxy)-1-(3,3-dichloro-2-propenyloxy)benzene, $n_D^{25.0}$ 1.5282

(174) 2-Trifluoromethyl-4-(4-sec-butylphenoxy)-1-(3,3-dibromo-2-propenyloxy)benzene, $n_D^{25.0}$ 1.5479

(175) 2-Trifluoromethyl-4-(4-tert-octylphenoxy)-1-(3,3-dichloro-2-propenyloxy)benzene, $n_D^{25.0}$ 1.5201

(176) 2-Trifluoromethyl-4-(4-tert-octylphenoxy)-1-(3,3-dibromo-2-propenyloxy)benzene, $n_D^{25.0}$ 1.5397

(177) 2-Trifluoromethyl-4-(4-tert-butylphenoxy)-1-(3,3-dichloro-2-propenyloxy)benzene, $n_D^{25.0}$ 1.5283

(178) 2-Trifluoromethyl-4-(4-tert-butylphenoxy)-1-(3,3-dibromo-2-propenyloxy)benzene, $n_D^{25.0}$ 1.5481

(179) 2-Trifluoromethyl-4-(3-(3,3-dichloro-2-propenyloxy)phenoxy)-1-(3,3-dichloro-2-propenyloxy)benzene, $n_D^{24.2}$ 1.5571

(180) 2-Trifluoromethyl-4-(3-(3,3-dibromo-2-propenyloxy)phenoxy)-1-(3,3-dibromo-2-propenyloxy)benzene, $n_D^{24.2}$ 1.5878

(181) 2-Trifluoromethyl-4-(13-naphthoxy)-1-(3,3-dichloro-2-propenyloxy)benzene, $n_D^{25.5}$ 1.5859

(182) 2-Trifluoromethyl-4-(13-naphthoxy)-1-(3,3-dibromo-2-propenyloxy)benzene, $n_D^{25.6}$ 1.5953

(183) 2-Trifluoromethyl-4-(3-tert-butylphenoxy)-1-(3,3-dichloro-2-propenyloxy)benzene, $n_D^{25.5}$ 1.5304

(184) 2-Trifluoromethyl-4-(3-tert-butylphenoxy)-1-(3,3-dibromo-2-propenyloxy)benzene, $n_D^{25.6}$ 1.5465

(185) 2-Trifluoromethyl-4-(4-(1-hydroxy-n-propyl)phenoxy)-1-(3,3-dibromo-2-propenyloxy)benzene, $n_D^{24.0}$ 1.5401

(186) 2-Trifluoromethyl-4-(2,4-diisopropylphenoxy)-1-(3,3-dichloro-2-propenyloxy)benzene, $n_D^{23.4}$ 1.5252

(187) 2-Trifluoromethyl-4-(2,4-diisopropylphenoxy)-1-(3,3-dibromo-2-propenyloxy)benzene, $n_D^{23.4}$ 1.5433

(188) 2-Trifluoromethyl-4-(5,6,7,8-tetrahydro-1-naphthoxy)-1-(3,3-dichloro-2-propenyloxy)benzene, $n_D^{23.4}$ 1.5538

(189) 2-Trifluoromethyl-4-(5,6,7,8-tetrahydro-1-naphthoxy)-1-(3,3-dibromo-2-propenyloxy)benzene, $n_D^{23.4}$ 1.5688

(190) 2-Trifluoromethyl-4-(3-chlorophenoxy)-1-(3,3-dichloro-2-propenyloxy)benzene, $n_D^{24.0}$ 1.5419

(191) 2-Trifluoromethyl-4-(3-chlorophenoxy)-1-(3,3-dibromo-2-propenyloxy)benzene, $n_D^{22.3}$ 1.5700

(192) 2-Trifluoromethyl-4-(3-(trifluoromethyl)phenoxy)-1-(3,3-dichloro-2-propenyloxy)benzene, $n_D^{25.5}$ 1.5081

(193) 2-Trifluoromethyl-4-(4-ethoxyphenoxy)-1-(3,3-dichloro-2-propenyloxy)benzene, $n_D^{25.5}$ 1.5375

(194) 2-Trifluoromethyl-4-(4-trifluoromethyl)phenoxy)-1-(3,3-dichloro-2-propenyloxy)benzene, $n_D^{25.0}$ 1.5091

(195) 2-Trifluoromethyl-4-(4-trifluoromethoxy)phenoxy)-1-(3,3-dichloro-2-propenyloxy)benzene, $n_D^{25.0}$ 1.4948

(196) 2-Trifluoromethyl-4-(4-ethoxyphenoxy)-1-(3,3-dibromo-2-propenyloxy)benzene, $n_D^{24.0}$ 1.5480

(197) 2-Trifluoromethyl-4-(4-methoxyphenoxy)-1-(3,3-dichloro-2-propenyloxy)benzene, $n_D^{24.0}$ 1.5448

(198) 2-Trifluoromethyl-4-(3,4-methylenedioxyphenoxy)-1-(3,3-dibromo-2-propenyloxy)benzene, $n_D^{24.2}$ 1.5480

(199) 2-Trifluoromethyl-4-(4-(trifluoromethyl)phenoxy)-1-(3,3-dibromo-2-propenyloxy)benzene, $n_D^{25.0}$ 1.5282

(200) 2-Trifluoromethyl-4-(4-(trifluoromethoxy)phenoxy)-1-(3,3-dichloro-2-propenyloxy)benzene, (201) 2,5-Dichloro-4-(3-chloro-5-trifluoromethyl-2-pyridyloxy)-1-(3,3-dichloro-2-propenyloxy)benzene, resinous (202) 2,5-Dichloro-4-(3-trifluoromethyl-5-chloro-2-pyridyloxy)-1-(3,3-dichloro-2-propenyloxy)benzene, m.p., 60.9° C.

(203) 2,5-Dichloro-4-(3-trifluoromethyl-5-chloro-2-pyridyloxy)-1-(3,3-dibromo-2-propenyloxy)benzene, m.p., 49.8° C.

(204) 2,5-Dichloro-4-(3,6-bistrifluoromethyl-2-pyridyloxy)-1-(3,3-dichloro-2-propenyloxy)benzene, m.p., 48.6° C.

(205) 2,5-Dichloro-4-(3,6-bistrifluoromethyl-2-pyridyloxy)-1-(3,3-dibromo-2-propenyloxy)benzene, m.p., 73.9° C.

(206) 2,5-Dichloro-4-(3-bromo-5-trifluoromethyl-2-pyridyloxy)-1-(3,3-dichloro-2-propenyloxy)benzene, m.p., 95.4° C.

(207) 2,5-Dichloro-4-(3-bromo-5-trifluoromethyl-2-pyridyloxy)-1-(3,3-dibromo-2-propenyloxy)benzene, m.p., 101.4° C.

(208) 3,5-Dichloro-4-(3-chloro-5-trifluoromethyl-2-pyridyloxy)-1-(3,3-dichloro-2-propenyloxy)benzene, m.p., 97.8° C.

(209) 3,5-Dichloro-4-(3-chloro-5-trifluoromethyl-2-pyridyloxy)-1-(3,3-dibromo-2-propenyloxy)benzene, m.p., 84.4° C.

(210) 3,5-Dichloro-4-(3-bromo-5-trifluoromethyl-2-pyridyloxy)-1-(3,3-dichloro-2-propenyloxy)benzene, m.p., 90.70° C. (211) 3,5-Dichloro-4-(3-bromo-5-trifluoromethyl-2-pyridyloxy)-1-(3,3-dibromo-2-propenyloxy)benzene, m.p., 85.0° C.

(212) 3,5-Dichloro-4-(3,5-bistrifluoromethyl-2-pyridyloxy)-1-(3,3-dichloro-2-propenyloxy)benzene, m.p., 77.6° C.

(213) 3,5-Dichloro-4-(3,5-bistrifluoromethyl-2-pyridyloxy)-1-(3,3-dibromo-2-propenyloxy)benzene, m.p., 79.5° C.

(214) 3-Chloro-4-(3,5-bistrifluoromethyl-2-pyridyloxy)-1-(3,3-dichloro-2-propenyloxy)benzene, $n_D^{23.0}$ 1.5130

(215) 3-Methyl-4-(3-chloro-5-trifluoromethyl-2-pyridyloxy)-1-(3,3-dichloro-2-propenyloxy)benzene, m.p., 48.7° C.

(216) 3-Chloro-4-(3-chloro-5-trifluoromethyl-2-pyridyloxy)-1-(3,3-dichloro-2-propenyloxy)benzene, m.p., 46.2° C.

(217) 2-Methyl-4-(3,5-bistrifluoromethyl-2-pyridyloxy)-1-(3,3-dichloro-2-propenyloxy)benzene, $n_D^{21.5}$ 1.5081

(218) 2-Methyl-4-(3,5-bistrifluoromethyl-2-pyridyloxy)-1-(3,3-dibromo-2-propenyloxy)benzene, $n_D^{21.5}$ 1.5299

(219) 3-Methyl-4-(3,5-bistrifluoromethyl-2-pyridyloxy)-1-(3,3-dichloro-2-propenyloxy)benzene, $n_D^{24.2}$ 1.5019

(220) 3-Methyl-4-(3,5-bistrifluoromethyl-2-pyridyloxy)-1-(3,3-dibromo-2-propenyloxy)benzene, $n_D^{24.2}$ 1.5271

(221) 3-Chloro-4-(3-chloro-5-trifluoromethyl-2-pyridyloxy)-1-(3,3-dibromo-2-propenyloxy)benzene, m.p., 42.8° C.

(222) 3-Methyl-4-(3-chloro-5-trifluoromethyl-2-pyridyloxy)-1-(3,3-dibromo-2-propenyloxy)benzene, m.p., 65.3° C.

(223) 2,5-Dichloro-4-(3-chloro-5-trifluoromethyl-2-pyridyloxy)-1-(3,3-dichloro-2-propenyloxy)benzene, m.p., 87.2° C.

(224) 2-Chloro-4-(4,5-bistrifluoromethyl-2-pyridyloxy)-1-(3,3-dibromo-2-propenyloxy)benzene, $n_D^{24.0}$ 1.5370

(225) 3-Chloro-4-(4,5-bistrifluoromethyl-2-pyridyloxy)-1-(3,3-dibromo-2-propenyloxy)benzene, $n_D^{24.0}$ 1.5359

(226) 2-Chloro-4-(3,5-bistrifluoromethyl-2-pyridyloxy)-1-(3,3-dibromo-2-propenyloxy)benzene, m.p., 54.5° C.

(227) 3-Chloro-4-(3,5-bistrifluoromethyl-2-pyridyloxy)-1-(3,3-dibromo-2-propenyloxy)benzene, $n_D^{24.2}$ 1.5161

(228) 2,5-Dichloro-4-(3,5-bistrifluoromethyl-2-pyridyloxy)-1-(3,3-dichloro-2-propenyloxy)benzene, m.p., 75°–76° C.

(229) 2,5-Dichloro-4-(3,5-bistrifluoromethyl-2-pyridyloxy)-1-(3,3-dibromo-2-propenyloxy)benzene, m.p., 73°–74° C.

(230) 2,6-Dichloro-4-(3,5-bistrifluoromethyl-2-pyridyloxy)-1-(3,3-dichloro-2-propenyloxy)benzene, m.p., 66.7° C.

(231) 2,6-Dichloro-4-(3,5-bistrifluoromethyl-2-pyridyloxy)-1-(3,3-dibromo-2-propenyloxy)benzene, m.p., 76.2° C.

(232) 2-Chloro-4-(4,5-bistrifluoromethyl-2-pyridyloxy)-1-(3,3-dichloro-2-propenyloxy)benzene, $n_D^{23.0}$ 1.5242

(233) 3-Chloro-4-(4,5-bistrifluoromethyl-2-pyridyloxy)-1-(3,3-dichloro-2-propenyloxy)benzene, $n_D^{23.0}$ 1.5196

(234) 2-Chloro-4-(3,5-bistrifluoromethyl-2-pyridyloxy)-1-(3,3-dichloro-2-propenyloxy)benzene, m.p., 58.8° C.

(235) 2-Chloro-4-(6-chloro-2-pyridyloxy)-1-(3,3-dichloro-2-propenyloxy)benzene, m.p., 68.220 C.

(236) 2,6-Dichloro-4-(3-chloro-5-trifluoromethyl-2-pyridyloxy)-1-(3,3-dichloro-2-propenyloxy)benzene, $n_D^{22.0}$ 1.5572

(237) 2-Bromo-6-chloro-4-(3-chloro-5-trifluoromethyl-2-pyridyloxy)-1-(3,3-chloro-2-propenyloxy)benzene, m.p., 59.5° C.

(238) 2,6-Dibromo-4-(3-chloro-5-trifluoromethyl-2-pyridyloxy)-1-(3,3-dichloro-2-propenyloxy)benzene, m.p., 71.2° C.

(239) 2,6-Dichloro-4-(3-chloro-5-trifluoromethyl-2-pyridyloxy)-1-(3,3-dibromo-2-propenyloxy)benzene, m.p., 58.2° C.

(240) 2-Trifluoromethyl-4-(3-chloro-5-trifluoromethyl-2-pyridyloxy)-1-(3,3-dichloro-2-propenyloxy)benzene, $n_D^{24.0}$ 1.5182

(241) 2-Trifluoromethyl-4-(3-chloro-5-trifluoromethyl-2-pyridyloxy)-1-(3,3-dibromo-2-propenyloxy)benzene, $n_D^{25.0}$ 1.5310

(242) 2-Bromo-4-(3-Chloro-5-trifluoromethyl-2-pyridyloxy)-1-(3,3-dibromo-2-propenyloxy)benzene, $n_D^{24.0}$ 1.5780

(243) 2,6-Dimethyl-4-(3-chloro-5-trifluoromethyl-2-pyridyloxy)-1-(3,3-dichloro-2-propenyloxy)benzene, $n_D^{24.0}$ 1.5413

(244) 2,6-Dimethyl-4-(3-chloro-5-trifluoromethyl-2-pyridyloxy)-1-(3,3-dibromo-2-propenyloxy)benzene, $n_D^{24.0}$ 1.5633

(245) 2,5-Dichloro-4-(3-chloro-5-trifluoromethyl-2-pyridyloxy)-1-(3,3-dichloro-2-propenyloxy)benzene, m.p., 105.9° C.

(246) 2,5-Dichloro-4-(3-chloro-5-trifluoromethyl-2-pyridyloxy)-1-(3,3-dibromo-2-propenyloxy)benzene, m.p., 104.2° C.

(247) 2-Tert-butyl-5-methyl-4-(5-tert-butyl-2-methyl-4-(3,3-dichloro-2-propenyloxy)phenylthio)-1-(3,3-dichloro-2-propenyloxy)benzene, $n_D^{25}$ 1.5643

(248) 2-Bromo-4-(1-methyl-1-(4-isopropoxyphenyl))ethyl-1-(3,3-dibromo-2-propenyloxy)benzene, m.p., 55.7° C.

(249) 2-Bromo-4-(1-methyl-1-(4-(3,3-dichloro-2-propenyloxy)phenyl))ethyl-2-(3,3-dichloro-2-propenyloxy)benzene, $n_D^{25}$ 1.5997

(250) 2-Chloro-4-(1-methyl-1-(4-isopropoxyphenyl))ethyl-1-(3,3-dichloro-1-propenyloxy)benzene, $n_D^{25}$ 1.5683

(251) 2-Chloro-4-(1-methyl-1-(4-isopropoxyphenyl))ethyl-1-(3,3-dibromo-2-propenyloxy)benzene, $n_D^{25}$ 1.5821

(252) 2-Chloro-4-(1-methyl-1-(4-bromophenyl))ethyl-1-(3,3-dichloro-2-propenyloxy)benzene, $n_D^{24}$ 1.6007

(253) 2-Chloro-4-(1-methyl-1-(4-bromophenyl))ethyl-1-(3,3-dibromo-2-propenyloxy)benzene, $n_D^{24}$ 1.6172

(254) 2,6-Dichloro-4-(1-methyl-1-(4-bromophenyl))ethyl-1-(3,3-dibromo-2-propenyloxy)benzene, $n_D^{25}$ 1.5752

(255) 2,6-Dichloro-4-(1-methyl-1-(4-bromophenyl))ethyl-1-(3,3-dibromo-2-propenyloxy)benzene, $n_D^{25}$ 1.6165

(256) 2-n-Propyl-4-(4-ethoxyphenylthio)-1-(3,3-dibromo-2-propenyloxy)benzene, $n_D^{20}$ 1.6152

(257) 2-n-Propyl-4-(4-isopropoxyphenylthio)-1-(3,3-dichloro-2-propenyloxy)benzene, $n_D^{20.5}$ 1.5851

(258) 2-n-Propyl-4-(4-isopropoxyphenylthio)-1-(3,3-dibromo-2-propenyloxy)benzene, $n_D^{20.5}$ 1.6041

(259) 2-Ethyl-4-(4-isopropoxyphenylthio)-1-(3,3-dichloro-2-propenyloxy)benzene, $n_D^{23.0}$ 1.5911

(260) 2-Ethyl-4-(4-isopropoxyphenylthio)-1-(3,3-dibromo-2-propenyloxy)benzene, $n_D^{23.0}$ 1.6105

(261) 2-Bromo-4-(4-isopropoxyphenylthio)-1-(3,3-dichloro-2-propenyloxy)benzene, $n_D^{20.5}$ 1.6202

(262) 2-Bromo-4-(4-isopropoxyphenylthio)-1-(3,3-dibromo-2-propenyloxy)benzene, $n_D^{21.0}$ 1.6413

(263) 2-Ethyl-4-(1-methyl-1-(4-isopropoxyphenyl))ethyl-1-(3,3-dibromo-2-propenyloxy)benzene, $n_D^{19}$ 1.5794

(264) 2-n-Propyl-4-(1-methyl-1-(4-isopropoxyphenyl))ethyl-1-(3,3-dibromo-2-propenyloxy)benzene, $n_D^{23}$ 1.5716

(265) 2-Bromo-4-(4-ethoxyphenylthio)-1-(3,3-dichloro-2-propenyloxy)benzene, $n_D^{23}$ 1.6286

(266) 2-Bromo-4-(4-ethoxyphenylthio)-1-(3,3-dibromo-2-propenyloxy)benzene, $n_D^{23}$ 1.6509

(267) 2-Bromo-4-(4-(3,3-dichloro-2-propenyloxy)phenylthio)-1-(3,3-dichloro-2-propenyloxy)benzene, $n_D^{25}$ 1.6360

(268) 2-n-Butyl-4-(4-ethoxyphenylthio)-1-(3,3-dichloro-2-propenyloxy)benzene, $n_D^{21}$ 1.6071

(269) 2-Bromo-4-(1-trifluoromethyl-1-(4-ethoxyphenyl)-2,2,2-trifluoroethyl)-1-(3,3-dibromo-2-propenyloxy)benzene, $n_D^{24}$ 1.5476

(270) 2,6-Dibromo-4-(1-trifluoromethyl-1-(4-ethoxyphenyl)-2,2,2-trifluoroethyl)-1-(3,3-dibromo-2-propenyloxy)benzene, resinous (271) 2-Trifluoromethyl-4-(4-methoxyphenylthio)-1-(3,3-dichloro-2-propenyloxy)benzene, $n_D^{24.5}$ 1.5523

(272) 2-n-Propyl-4-(4-ethoxyphenylthio)-1-(3,3-dichloro-2-propenyloxy)benzene, $n_D^{20}$ 1.5942

(273) 2-Bromo-4-(4-chlorophenylthio)-1-(3,3-dichloro-2-propenyloxy)benzene, $n_D^{25}$ 1.65 14

(274) 2-Bromo-4-(4-chlorophenylthio)-1-(3,3-dibromo-2-propenyloxy)benzene, $N_D^{23}$ 1.6757

(275) 2-Bromo-4-(1-methyl-1-(4-ethoxyphenyl))ethyl-1-(3,3-dichloro-2-propenyloxy)benzene, $n_D^{25}$ 1.5869

(276) 2-Bromo-4-(1-methyl-1-(4-ethoxyphenyl))ethyl-1-(3,3-dibromo-2-propenyloxy)benzene, $n_D^{25}$ 1.6018

(277) 2-Bromo-4-(1-methyl-1-(4-isopropoxyphenyl))ethyl-1-(3,3-dichloro-2-propenyloxy)benzene, $n_D^{23.5}$ 1.5793

(278) 2-Bromo-4-(1-methyl-1-(4-isopropoxyphenyl))ethynyl-1-(3,3-dichloro-2-propenyloxy)benzene, $n_D^{23.0}$ 1.5778

(279) 2-Bromo-4-(1-methyl-1-(4-isopropoxyphenyl))ethyl-1-(3,3-dichloro-2-propenyloxy)benzene, $n_D^{23.3}$ 1.5821

(280) 2-Bromo-4-(1-(4-isopropoxyphenyl))ethyl-1-(3,3-dibromo-2-propenyloxy)benzene, $n_D^{23.3}$ 1.6018

(281) 2-Chloro-6-(3-chlorophenoxy)-3-(3,3-dichloro-2-propenyloxy)benzene, (282) 2-n-Propyl-4-(4-isopropoxyphenoxy)-1-(3,3-dichloro-2-propenyloxy)benzene, $n_D^{22.5}$ 1.556

(283) 2-Bromo-4-(4-isopropoxyphenyl)methyl-1-(3,3-dichloro-2-propenyloxy)benzene, $n_D^{23.5}$ 1.5681

(284) 2-Bromo-4-(4-isopropoxyphenyl)methyl-1-(3,3-dibromo-2-propenyloxy)benzene, $n_D^{23.5}$ 1.6002

(285) 2,6-Dichloro-4-(3-chloro-5-trifluoromethyl-2-pyridyl)amino)-1-(3,3-dichloro-2-propenyloxy)benzene, m.p., 77.8° C.

(286) 2,6-Dichloro-4-(3-chloro-5-trifluoromethyl-2-pyridyl)amino-1-(3,3-dibromo-2-propenyloxy)benzene, m.p., 106.1° C.

(287) 2,6-Dibromo-4-(4-isopropyloxyphenyl)sulfonyl-1-(3,3-dichloro-2-propenyloxy)benzene, $^1$H-NMR (CDCl$_3$/TMS) δ (ppm): 1.35 (6H, d, J=6.0 Hz), 4.62 (1H, septet, J=6.0 Hz), 4.68 (2H, d, J=6.7 Hz), 6.31 (1H, t, J=6.7 Hz), 6.96 (2H, d, J=7.1 Hz), 7.83 (2H, d, J=7.0 Hz), 8.04 (2H, s), resinous (288) 2,6-Dibromo-4-(4-isopropyloxyphenyl)sulfonyl-1-(3,3-dibromo-2-propenyloxy)benzene, $^1$H-NMR (CDCl$_3$/TMS) δ (ppm): 1.34 (6H, d, J=6.0 Hz), 4.57 (2H, d, J=6.7 Hz), 4.60 (1H, septet, J=6.0 Hz), 6.85 (1H, t, J=6.6 Hz), 6.95 (2H, d, J=8.0 Hz), 7.81 (2H, d, J=7.9 Hz), 8.04 (2H, s), resinous (289) 3,5-Dichloro-4-(3-chloro-5-trifluoromethyl-2-pyridyloxy)-1-(3,3-dichloro-2-propenylamino)benzene, glassy (290) 3,5-Dichloro-4-(3-chloro-5-trifluoromethyl-2-pyridyloxy)-1-(3,3-dibromo-2-propenylamino)benzene, glassy (291) 2-Ethoxy-4-(4-isopropoxyphenoxy)-1-(3,3-dichloro-2-propenyloxy)benzene, $n_D^{23.5}$ 1.5580

(292) 2-Ethoxy-4-(4-isopropoxyphenoxy)-1-(3,3-dibromo-2-propenyloxy)benzene, m.p., 69.1° C.

(293) 2-Bromo-4-(1-ethyl-1-(4-isopropoxyphenoxy)propyl)-1-(3,3-dichloro-2-propenyloxy)benzene, $n_D^{24.5}$ 1.5685

(294) 2-Bromo-4-(1-methyl-1-(4-isopropoxyphenoxy)propyl)-1-(3,3-dibromo-2-propenyloxy)benzene, $n_D^{24.5}$ 1.5851

(295) 3-Methyl-4-(4-ethoxyphenoxy)-1-(3,3-dichloro-2-propenyloxy)benzene, $n_D^{23.0}$ 1.5705

(296) 3-Methyl-4-(4-ethoxyphenoxy)-1-(3,3-dibromo-2-propenyloxy)benzene, $n_D^{23.0}$ 1.5942

(297) 3,5-Dimethyl-4-(3-chloro-5-trifluoromethyl-2-pyridyloxy)-1-(3,3-dichloro-2-propenyloxy)benzene, $n_D^{26.0}$ 1.5410

(298) 3,5-Dimethyl-4-(3-chloro-5-trifluoromethyl-2-pyridyloxy)-1-(3,3-dibromo-2-propenyloxy)benzene, m.p., 60.2° C.

(299) 3-Bromo-4-(3-bromo-5-trifluoromethyl-2-pyridyloxy)-1-(3,3-dichloro-2-propenyloxy)benzene, $n_D^{24.6}$ 1.5624

(300) 3-Bromo-4-(3-bromo-5-trifluoromethyl-2-pyridyloxy)-1-(3,3-dibromo-2-propenyloxy)benzene, $n_D^{24.6}$ 1.5853

(301) 3-Bromo-4-(3-chloro-5-trifluoromethyl-2-pyridyloxy)-1-(3,3-dichloro-2-propenyloxy)benzene, $n_D^{24.6}$ 1.5581

(302) 3-Bromo-4-(3-chloro-5-trifluoromethyl-2-pyridyloxy)-1-(3,3-dibromo-2-propenyloxy)benzene, $n_D^{24.6}$ 1.5748

(303) 2,3-Dimethyl-4-(3-chloro-5-trifluoromethyl-2-pyridyloxy)-1-(3,3-dibromo-2-propenyloxy)benzene, m.p., 54.9

(304) 2-(Allyloxyimino)-4-(4-isopropoxyphenoxy)-1-(3,3-dichloro-2-propenyloxy)benzene, $n_D^{23}$ 1.5726

(305) 2-(Allyloxyimino)-4-(4-isopropoxyphenoxy)-1-(3,3-dibromo-2-propenyloxy)benzene, $n_D^{23}$ 1.5972

(306) 2-Isopropyl-4-(4-isopropoxyphenoxy)phenoxy-1-(3,3-dichloro-2-propenyloxy)benzene, $n_D^{23}$ 1.5748

(307) 2-Isopropyl-4-(4-isopropoxyphenoxy)phenoxy-1-(3,3-dibromo-2-propenyloxy)benzene, $n_D^{23}$ 1.5860

(308) 3-Methyl-4-(2-methyl-3,4-ethylenedioxyphenoxy)-1-(3,3-dichloro-2-propenyloxy)benzene, $n_D^{22.5}$ 1.5877

(309) 2,3-Dimethyl-4-(3-chloro-5-trifluoromethyl-2-pyridyloxy)-1-(3,3-dichloro-2-propenyloxy)benzene, $n_D^{23}$ 1.5444

(310) 2,3,6-Trimethyl-4-(3-chloro-5-trifluoromethyl-2-pyridyloxy)-1-(3,3-dichloro-2-propenyloxy)benzene, m.p., 49.9° C.

(311) 2,3,6-Trimethyl-4-(3-chloro-5-trifluoromethyl-2-pyridyloxy)-1-(3,3-dibromo-2-propenyloxy)benzene, m.p., 151.3° C.

(312) 2-[Isopropyl-4-(2-methyl-3,4-ethylenedioxyphenoxy)-1-(3,3-dichloro-2-propenyloxy)benzene, $n_D^{22}$ 1.5718

(313) 2-Isopropyl-4-(2-methyl-3,4-ethylenedioxyphenoxy)-1-(3,3-dibromo-2-propenyloxy)benzene, $n_D^{22}$ 1.5908

(314) 2,6-Dichloro-4-(1-methyl-1-(3,5-dichloro-4-(3-chloro-5-trifluoromethyl-2-pyridyloxy)phenyl)ethyl)-1-(3,3-dichloro-2-propenyloxy)benzene, $n_D^{21.5}$ 1.5726

(315) 2,6-Dichloro-4-(1-methyl-1-(3,5-dichloro-4-(3-chloro-5-trifluoromethyl-2-pyridyloxy)phenyl)ethyl)-1-(3,3-dibromo-2-propenyloxy)benzene, glassy (316) 3-Tert-butyl-4-(3-chloro-5-trifluoromethyl-2-pyridyloxy)-1-(3,3-dichloro-2-propenyloxy)benzene, $n_D^{22}$ 1.5388

(317) 3-Tert-butyl-4-(3-chloro-5-trifluoromethyl-2-pyridyloxy)-1-(3,3-dibromo-2-propenyloxy)benzene, $n_D^{22}$ 1.5591

(318) 2,6-Dimethyl-4-(3-chloro-5-trifluoromethyl-2-pyridyloxy)-1-(3,3-dichloro-2-propenyloxy)benzene, $n_D^{22}$ 1.5400

(319) 2,6-Dimethyl-4-(3-chloro-5-trifluoromethyl-2-pyridyloxy)-1-(3,3-dibromo-2-propenyloxy)benzene, $n_D^{22}$ 1.5621

(320) 2-Isopropyl-4-(3-chloro-5-trifluoromethyl-2-pyridyloxy)-1-(3,3-dichloro-2-propenyloxy)benzene, $n_D^{22}$ 1.5398

(321) 2-Isopropyl-4-(3-chloro-5-trifluoromethyl-2-pyridyloxy)-1-(3,3-dibromo-2-propenyloxy)benzene, $n_D^{22}$ 1.5587

(322) 2,6-Dimethyl-4-(5-trifluoromethyl-2-pyridyloxy)-1-(3,3-dichloro-2-propenyloxy)benzene, $n_D^{22}$ 1.5342

(323) 2,6-Dimethyl-4-(5-trifluoromethyl-2-pyridyloxy)-1-(3,3-dibromo-2-propenyloxy)benzene, $n_D^{22}$ 1.5549

(324) 3,5-Dichloro-4-(5-nitro-2-pyridyloxy)-1-(3,3-dichloro-2-propenyloxy)benzene, $n_D^{21}$ 1.6028

(325) 3,5-Dichloro-4-(5-nitro-2-pyridyloxy)-1-(3,3-dibromo-2-propenyloxy)benzene, $n_D^{21}$ 1.6247

(326) 2,6-Dichloro-4-(2,4-dinitrophenoxy)-1-(3,3-dichloro-2-propenyloxy)benzene, m.p., 74.9° C.

(327) 2-Bromo-4-(1-methyl-1-(3-chloro-5-trifluoromethyl-2-pyridyloxy)phenyl)ethyl)-1-(3,3-dichloro-2-propenyloxy)benzene, $n_D^{23}$ 1.5725

(328) 2-Bromo-4-(1-methyl-1-(3-chloro-5-trifluoromethyl-2-pyridyloxy)phenyl)ethyl)-1-(3,3-dibromo-2-propenyloxy)benzene, $n_D^{23}$ 1.5942

(329) 2-Bromo-4-(4-(3-chloro-5-trifluoromethyl-2-pyridyloxy)phenoxy)-1-(3,3-dichloro-2-propenyloxy)benzene, $n_D^{23}$ 1.5791

(330) 2-Bromo-4-(4-(3-chloro-5-trifluoromethyl-2-pyridyloxy)phenoxy)-1-(3,3-dibromo-2-propenyloxy)benzene, $n_D^{23}$ 1.5849

(331) 2-Methyl-5-chloro-4-(3-chloro-5-trifluoromethyl-2-pyridyloxy)-1-(3,3-dichloro-2-propenyloxy)benzene, $n_D$ 18.5 1.5530

(332) 2-Methyl-5-chloro-4-(3-chloro-5-trifluoromethyl-2-pyridyloxy)- 1-(3,3-dibromo-2-propenyloxy)benzene, $n_D^{8.5}$ 1.5687

(333) 2-(1-Methyl-2-propenyl)-4-(4-isopropoxyphenoxy)-1-(3,3-dichloro-2-propenyloxy)benzene, $n_D^{22.5}$ 1.5611

(334) 2-(1-Methyl-2-propenyl)-4-(4-isopropoxyphenoxy)-1-(3,3-dibromo-2-propenyloxy)benzene, $n_D^{22.5}$ 1.5791

(335) 3-Chloro-5-bromo-4-(3-chloro-5-trifluoromethyl-2-pyridyloxy)-1-(3,3-dichloro-2-propenyloxy)benzene, m.p., 95.5° C.

(336) 3-Chloro-5-bromo-4-(3-chloro-5-trifluoromethyl-2-pyridyloxy)-1-(3,3-dibromo-2-propenyloxy)benzene, m.p., 94.3° C.

(337) 3,5-Dichloro-4-(4-cyanophenoxy)-1-(3,3-dichloro-2-propenyloxy)benzene, m.p., 119.2° C.

(338) 2,6-Dibromo-4-(3-chloro-5-trifluoromethyl-2-pyridylamino)-1-(3,3-dichloro-2-propenyloxy)benzene, m.p., 117.1° C.

(339) 3,5-Dichloro-4-(3-bromo-5-nitro-2-pyridyloxy)-1-(3,3-dibromo-2-propenyloxy)benzene, m.p., 91.6° C.

(340) 3-Methyl-4-(3-methoxyphenoxy)-1-(3,3-dichloro-2-propenyloxy)benzene, $n_D^{23}$ 1.5787

(341) 2-Isopropyl-5-chloro-4-(3-chloro-5-trifluoromethyl-2-pyridyloxy)-1-(3,3-dichloro-2-propenyloxy)benzene, $n_D^{23.3}$ 1.5380

(342) 2-Isopropyl-5-chloro-4-(3-chloro-5-trifluoromethyl-2-pyridyloxy)-1-(3,3-dibromo-2-propenyloxy)benzene, $n_D^{23.3}$ 1.5552

(343) 2-Bromo-4-(2-methyl-1-(4-ethoxyphenyl))propyl-1-(3,3-dichloro-2-propenyloxy)benzene, $n_D^{23.5}$ 1.5791

(344) 2-Bromo-4-(2-methyl-1-(4-ethoxyphenyl))propyl-1-(3,3-dibromo-2-propenyloxy)benzene, m.p., 64.3° C.

(345) 2-Bromo-4-(2-methyl-1-(4-isopropoxyphenyl))propyl-1-(3,3-dichloro2-propenyloxy)benzene, $n_D^{23.5}$ 1.5694

(346) 2-Bromo-4-(2-methyl-1-(4-ethoxyphenyl))propyl-1-(3,3-dibromo-2-propenyloxy)benzene, $n_D^{23.5}$ 1.5820

(347) 2-Isopropyl-4-(2-methyl-4-(3,3-dichloro-2-propenyloxy))phenoxy-1-(3,3-dichloro-2-propenyloxy)benzene, $n_D^{20}$ 1.573

(348) 2-Isopropyl-4-(2-methyl-4-(3,3-dichloro-2-propenyloxy))phenoxy-1-(3,3-dibromo-2-propenyloxy)benzene, $n_D^{20}$ 1.6070

(349) 3,5-Dichloro-4-(2,6-dichloro-4-trifluoromethyl)phenoxy-1-(3,3-dichloro-2-propenyloxy)benzene, $n_D^{24}$ 1.5735

(350) 3,5-Dichloro-4-(2-fluoro-4-nitrophenoxy)-1-(3,3-dichloro-2-propenyloxy)benzene, m.p., 94.2° C.

(351) 3,5-Dichloro-4-(2-fluoro-4-nitrophenoxy)-1-(3,3-dibromo-2-propenyloxy)benzene, m.p., 79.3° C.

(352) 3,5-Dichloro-4-(2-chloro-4-nitrophenoxy)-1-(3,3-dichloro-2-propenyloxy)benzene, $n_D^{23.5}$ 1.6172

(353) 3,5-Dichloro-4-(2-chloro-4-nitrophenoxy)-1-(3,3-dibromo-2-propenyloxy)benzene, $n_D^{23.5}$ 1.6396

(354) 3,5-Dichloro-4-(6-chloro-3,5-bistrifluoromethyl-2-pyridyloxy)-1-(3,3-dichloro-2-propenyloxy)benzene, m.p., 108.9° C.

(355) 3,5-Dichloro-4-(2-nitro-4-trifluoromethylphenoxy)-1-(3,3-dichloro-2-propenyloxy)benzene, $n_D^{21.5}$ 1.5706

(356) 3,5-Dichloro-4-(2-nitro-4-trifluoromethylphenoxy)-1-(3,3-dibromo-2-propenyloxy)benzene, $n_D^{21.5}$ 1.5870

(357) 3,5-Dichloro-4-(2,4-dinitro-6-trifluoromethylphenoxy)-1-(3,3-dichloro-2-propenyloxy)benzene, $n_D^{21.5}$ 1.5778

(358) 3,5-Dichloro-4-(2,4-dinitro-6-trifluoromethylphenoxy)-1-(3,3-dibromo-2-propenyloxy)benzene, $n_D^{21.5}$ 1.588

(359) 3,5-Dichloro-4-(2-trifluoromethyl-4-nitrophenoxy)-1-(3,3-dichloro- 2-propenyloxy)benzene, $n_D^{21.5}$ 1.5757

(360) 3,5-Dichloro-4-(2-trifluoromethyl-4-nitrophenoxy)-1-(3,3-dibromo-2-propenyloxy)benzene, $n_D^{21.5}$ 1.5962

(361) 3,5-Dichloro-4-(2,4-bistrifluoromethylphenoxy)-1-(3,3-dichloro-2-propenyloxy)benzene, $n_D^{24}$ 1.5333

(362) 3,5-Dichloro-4-(2,4-dinitrophenoxy)-1-(3,3-dibromo-2-propenyloxy)benzene, $n_D^{23}$ 1.6290

(363) 3-Methyl-4-(4-(2,2,2-trifluoroethoxy)phenoxy)-1-(3,3-dichloro-2-propenyloxy)benzene, $n_D^{24.5}$ 1.5382

(364) 3-Methyl-4-(4-nitrophenoxy)-1-(3,3-dichloro-2-propenyloxy)benzene, $n_D^{24.5}$ 1.6057

(365) 3,5-Dichloro-4-(4-acetamidophenoxy)-1-(3,3-dichloro-2-propenyloxy)benzene, glassy (366) 3,5-Dichloro-4-(4-trifluoromethylacetamidophenoxy)-1-(3,3-dichloro-2-propenyloxy)benzene, $n_D^{22.5}$ 1.5708

(367) 3,5-Dichloro-4-(2,6-dichloro-4-trifluoromethylphenoxy)-1-(3,3-dibromo-2-allyloxy)benzene, $n_D^{24.5}$ 1.5878

The following will describe some production examples of the intermediate compound of the formula II.

EXAMPLE 11

Production of intermediate compound 67

First, 1.07 g of hydroquinone monobenzyl ether and 500 ml of carbon tetrachloride were charged into a reaction vessel, and a solution prepared by dissolving 1.01 g of t-butyl hypochlorite in $_D^{10}$ ml of carbon tetrachloride was slowly added dropwise with stirring under ice cooling. After 24 hours, the reaction solution was poured into water and the organic layer (carbon tetrachloride) was separated. Then, the organic layer was washed with water, dried over anhydrous magnesium sulfate and concentrated to give a crude product. This crude product was subjected to silica gel chromatography to give 0.85 g of 2,6-dichloro-4-benzyloxyphenol (yield, 59%).

Then, 0.85 g of 2,6-dichloro-4-benzyloxyphenol, 0.48 g of potassium carbonate, 0.75 g of 2,3-dichloro-5-trifluoromethylpyridine and 10 ml of N,N-dimethylformamide were charged into a reaction vessel, and stirred at 85° to 90° C. for 3 hours. Then, the reaction solution was cooled to room temperature, poured into water and extracted twice with 50 ml of diethyl ether. The ether layers were combined, washed with water, dried over anhydrous magnesium sulfate and then concentrated to give a crude product. This crude product was subjected to silica gel chromatography to give 1.39 g of 3,5-dichloro-4-(3-chloro-5-trifluoromethyl-2-pyridyloxy)-1-benzyloxybenzene, (yield, 98%).

Then, 1.39 g of 3,5-dichloro-4-(3-chloro-5-trifluoromethyl-2-pyridyloxy)-1-benzyloxybenzene, and 20 ml of methylene chloride were charged into a reaction vessel, and a solution of boron tribromide (1.63 g) in methylene chloride (10 ml) was added dropwise with stirring under ice cooling (−10° C. to 0° C.). After stirring for one hour under ice cooling, the mixture was poured into 10% hydrochloric acid and extracted twice with 50 ml of methylene chloride. Then, the organic layers were combined, washed with water, dried over anhydrous magnesium sulfate and concentrated to give a crude product. This crude product was subjected to silica gel column chromatography to give 1.03 g of 3,5-dichloro-4-(3-chloro-5-trifluoromethyl-2-pyridyloxy)phenol (yield, 93%), m.p., 152.6° C.

EXAMPLE 12

Production of intermediate compound 63

To a solution prepared by dissolving 2.8 g of hydroquinone in 20 ml of N,N-dimethylformamide, 1.39 g of sodium hydride (60% oil-based) was added, slowly, with stirring under ice cooling. After completion of the generation of hydrogen gas from the reaction solution, a solution prepared by dissolving 5 g of 2,3-dichloro-5-trifluoromethylpyridine in 10 ml of N,N-dimethylformamide was added dropwise. After stirring at room temperature for 3 hours, the reaction solution was poured into ice-water, and extracted twice with 200 ml of diethyl ether. Then, the ether layers were combined, washed with water, dried over anhydrous magnesium sulfate and then concentrated to give a crude product. This crude product was subjected to silica gel chromatography to give 2.88 g of 4-(3-chloro-5-trifluoromethyl-2-pyridyloxy) phenol (yield, 43%).

To a solution prepared by dissolving the resulting 2.88 g of 4-(3-chloro-5-trifluoromethyl-2-pyridyloxy)phenol in 300 ml of chloroform, 4.80 g of tetra-n-butylammonium tribromide was slowly added with stirring under room temperature. After 12 hours, the reaction solution was concentrated, and the residue was extracted twice with 100 ml of diethyl ether. Then, the ether layers were combined, washed with water, dried over anhydrous magnesium sulfate and then concentrated to give a crude product. This crude product was subjected to silica gel chromatography to give 2.53 g of 2-bromo-4-(3-chloro-5-trifluoromethyl-2-pyridyloxy)phenol (yield, 69%).

$^1$H-NMR (CDCl$_3$/TMS) δ (ppm): 5.54 (1H, br), 7.06 (3H, brs), 7.33 (1H, d), 7.97 (1H, d), 8.27 (1H, d)

EXAMPLE 13

Production of intermediate compound 5

First, 20.4 g of 2-isopropylphenol and 750 ml of chloroform were charged into a reaction vessel, and 80 g of tetra-n-butylammonium tribromide was added at room temperature (about 20° C.) with stirring and the mixture was stirred at room temperature for additional 24 hours. To the reaction solution, 750 ml of a saturated sodium sulfite solution was added, and the mixture was shaken vigorously to concentrate the chloroform layer. To the residue, 500 ml of diethyl ether and 500 ml of 10% hydrochloric acid were added, and the mixture was shaken vigorously. The ether layer was dried over anhydrous magnesium sulfate and concentrated to give 32 g of 4-bromo-2-isopropylphenol (yield, 100%).

A mixture of 32 g of 4-bromo-2-isopropylphenol, 25.7 g of benzyl bromide, 23 g of potassium carbonate and 300 ml of N,N-dimethylformamide was stirred at room temperature for 24 hours. The reaction solution was poured into ice-water, acidified by adding 10% hydrochloric acid and then extracted with 500 ml of diethyl ether. Then, the ether layer was washed with a saturated saline solution, dried over anhydrous magnesium sulfate and concentrated. The residue was subjected to silica gel column chromatography to give 30 g of 4-bromo-2-isopropylphenyl benzyl ether (yield, 65%).

A mixture of 10 g of 4-bromo-2-isopropylphenyl benzyl ether, 4.7 g of 4-ethoxyphenol, 4.7 g of potassium carbonate, 0.30 g of copper powder, 0.30 g of cuprous iodide and 30 ml of pyridine was stirred at 130° C. to 140° C. for 24 hours. The reaction solution was cooled to room temperature, poured into ice-water and then acidified by adding 10% hydrochloric acid. The solution was extracted with 100 ml of diethyl ether, washed in turn with 10% hydrochloric acid, an aqueous 10% sodium hydroxide solution and a saturated saline solution, dried over anhydrous magnesium sulfate and then concentrated. The residue was subjected to silica gel column chromatography to give 4.4 g of 4-(4-ethoxyphenoxy)-2-isopropylphenyl benzyl ether (yield, 37%).

Then, 4.4 g of 4-(4-ethoxyphenoxy)-2-isopropylphenyl benzyl ether and 100 ml of ethyl acetate were charged into a reaction vessel, and air in the vessel was replaced with nitrogen. Then, 0.50 g of 5% palladium-carbon was added, and nitrogen in the vessel was replaced with hydrogen, followed by vigorous stirring at room temperature for 24 hours. After hydrogen in the vessel was replaced with nitrogen, the reaction vessel was filtered with Celite, and the filtrate was concentrated. The residue was subjected to silica gel chromatography to give 3.1 g of 2-isopropyl-4-(4-ethoxyphenoxy)phenol (yield, 93%).

$n_D^{25.5}$ 1.5612

$^1$H-NMR (CDCl$_3$/TMS) δ (ppm): 1.22 (6H, d), 1.41 (3H, t), 3.13–3.22 (1H, m), 4.01 (2H, q), 4.69 (1H, s), 6.62–6.93 (7H, m)

EXAMPLE 14

Production of intermediate compound 87

First, 7.44 g of 4,4'-bispropylidenebiphenol, 4.63 g of 2-bromopropane, 4.53 g of Potassium carbonate and 50 ml of N,N dimethylformide were charged into a reaction vessel, and the mixture was stirred at an oil bath temperature of 80° C. to 90° C. for 6 hours. The reaction solution was poured into water and extracted three times with 30 ml of ethyl acetate. Then, the ethyl acetate layers were combined, washed with water, dried over anhydrous magnesium sulfate and concentrated to give a crude product. This crude product was subjected to silica gel chromatography to give 3.89 g of 4-(1-(4-isopropyloxyphenyl)-1-methylethyl)phenol (yield, 44%).

To a solution of 4-(1-(4-isopropyloxyphenyl)-1-methylethyl)phenol (0.51 g) in carbon tetrachloriode (1.3 ml), a solution prepared by dissolving 0.23 g of tert-butyl hypochlorite in 0.5 ml of carbon tetrachloride was added dropwise with stirring under ice cooling. After 30 minutes, an ice bath was removed, and the mixture was stirred at room temperature for 30 minutes. The reaction solution was poured into water and extracted three times with 5 ml of carbon tetrachloride. Then, the carbon tetrachloride layers were combined, washed with water, dried over anhydrous magnesium sulfate and then concentrated to give a crude product. This crude product was subjected to silica gel column chromatography to give 0.49 g of 4-(1-(4-isopropyloxyphenyl)-1-methylethyl)-2-chlorophenol (yield, 85%).

$n_D^{26}$ 1.5557;

$^1$H-NMR (CDCl$_3$/TMS) δ (ppm): 1.33 (6H, d), 1.62 (6H, s), 5.43 (1H, s), 6.78 (2H, d), 6.89 (1H, d), 7.02 (1H, dd), 7.11 (2H, d), 7.18 (1H, d)

EXAMPLE 15

Production of intermediate compound 23

A mixture of 6.3 g of 4-isopropoxyphenol, 10.5 g of 4-bromophenyl benzyl ether, 8.3 g of potassium carbonate, 0.5 g of copper powder, 0.5 g of cuprous chloride and 3.5 g of pyridine was stirred at 130° C. to 140° C. for 24 hours. The reaction solution was cooled to room temperature, pound into water and then acidified by adding 10% hydrochloric acid. The solution was extracted with 100 ml of diethyl ether, washed in turn with 10% hydrochloric acid, an aqueous 10% sodium hydroxide solution and a saturated saline solution, dried over anhydrous magnesium sulfate and then concentrated. The crude product was subjected to silica gel column chromatography to give 4.3 g of 4-(4-isopropyloxy)phenyl benzyl ether (yield, 32%).

Then, 4.3 g of 4-(4-isopropyloxy)phenyl benzyl ether and 100 ml of ethyl acetate were charged into a reaction vessel, and air in the vessel was replaced with nitrogen. Then, 0.50 g of 10% palladium-carbon was added, and nitrogen in the vessel was replaced with hydrogen, followed by vigorous stirring at room temperature for 24 hours. After hydrogen in the vessel was replaced with nitrogen, the reaction vessel was filtered with Celite, and the filtrate was concentrated. The residue was subjected to silica gel column chromatography to give 2.8 g of 4-(4-isopropoxyphenoxy)phenol (yield, 89%).

To a mixture of 1.23 g of 4-(4-isopropoxyphenoxy)phenol, 1.4 g of potassium carbonate and 10 ml of N,N-dimethylformamide 0.65 ml of allyl bromide was added dropwise at room temperature with stirring. After 24 minutes, the reaction solution was poured into water, and acidified by adding 10% hydrochloric acid. The solution was extracted with 50 ml of diethyl ether, washed in turn with 10% hydrochloric acid, an aqueous 10% sodium hydroxide and a saturated saline solution, dried over anhydrous magnesium sulfate and then concentrated. The residue was subjected to silica gel column chromatography to give 0.98 g of 4-(4-isopropoxyphenoxy)phenyl allyl ether (yield, 69%).

Then, 0.98 g of 4-(4-isopropoxyphenoxy)phenyl allyl ether was heated at 190° C. to 200° C. for 6 hours with stirring. The reaction product was cooled to room temperature and then subjected to silica gel column chromatography to give 0.85 g of 2-allyl-4-(4-isopropoxyphenoxy)phenol (yield, 87%).

$^1$H-NMR (CDCl$_3$/TMS) δ (ppm): 1.32 (6H, d), 3.35–3.38 (2H, m), 4.41–4.51 (1H, m), 4.77 (1H, s), 5.11–5.20 (2H, m), 5.97–6.07 (1H, m), 6.73–6.91 (7H, m)

EXAMPLE 16

Production of intermediate compound 29

First, 41.33 g of 2-trifluoromethylphenol and 1800 ml of chloroform were charged into a reaction vessel, and 129.16 g of tetra-n-butylammonium tribromide was slowly added at room temperature over about one hour with stirring. After stirring at room temperature for 72 hours, the reaction solution was concentrated. Then, 500 ml of 10% hydrochloric acid was added to the resultant residue, and the mixture was extracted four times with 200 ml of diethyl ether. The ether layers were combined, washed with water, dried over anhydrous magnesium sulfate and then concentrated to give 49.5 g of 4-bromo-2-trifluoromethylphenol as a crude product (yield, 81%).

Then, 8.47 g of 4-bromo-2-trifluoromethylphenol, 5.34 g of potassium carbonate, 4.49 g of benzyl chloride and 100 ml of N,N-dimethylformamide were charged into a reaction vessel, and stirred under ice cooling. After 24 hours, the reaction solution was poured into ice-water and extracted three times with 50 ml of diethyl ether. The ether layers were combined, washed with an aqueous 10 % sodium hydroxide solution, dried over anhydrous magnesium sulfate and then concentrated to give a crude product. This crude product was subjected to silica gel chromatography to give 9.38 g of 4-bromo-2-trifluoromethyl-1-benzyloxybenzene, (yield, 81%).

Then, 5.10 g of 4-bromo-2-trifluoromethyl-1-benzyloxybenzene, 2.34 g of p-ethoxyphenol, 2.13 g of potassium carbonate, 100 mg of copper and 200 mg of cuprous chloride were charged into a reaction vessel, and stirred at 130° C. to 140° C. for 5 hours. The reaction solution was cooled to room temperature, poured into ice-water and then acidified by adding 10% hydrochloric acid. The solution was extracted twice with 100 ml of diethyl ether. Then, the ether layers were combined, washed with water, dried over anhydrous magnesium sulfate and concentrated to give a crude product. This crude product was subjected to silica gel chromatography to give 2.50 g of 2-trifluoromethyl-4-(4-ethoxyphenoxy)-1-benzyloxybenzene, (yield, 41%).

Then, 2.50 g of 2-trifluoromethyl-4-(4-ethoxyphenoxy)-1-benzyloxybenzene, 100 ml of ethyl acetate and 0.50 g of 10% palladium-carbon were charged into a reaction vessel, and air in the vessel was replaced with nitrogen. Then, nitrogen was replaced with hydrogen at room temperature with stirring. After stirring at room temperature for 24 hours, the reaction solution was filtered, and the filtrate was concentrated to give a crude product. This crude product was subjected to silica gel chromatography to give 1.75 g of 2-trifluoro-4-(4-ethoxyphenoxy)phenol (yield, 91%).

$n_D^{23.5}$ 1.5322

Other examples of the intermediate compound of the formula II will be described below.

1) 2-n-Propyl-4-(4-ethoxyphenoxy)phenol $^1$H-NMR (CDCl$_3$/TMS) δ (ppm): 0.96 (3H, t), 1.41 (3H, t), 1.55–1.67 (2H, m), 2.53 (2H, t), 4.01 (2H, q), 4.62 (1H, s), 6.70–6.93 (7H, m)

2) 2-Isopropyl-4-(2-chloro-4-ethoxyphenoxy)phenol $^1$H-NMR (CDCl$_3$/TMS) δ (ppm): 1.23 (6H, d), 1.41 (3H, t), 3.12–3.22 (1H, m), 4.01 (2H, q), 4.62 (1H, s), 6.56–6.99 (6H, m)

3) 2-Ethyl-4-(4-ethoxyphenoxy)phenol $^1$H-NMR (CDCl$_3$/TMS) δ (ppm): 1.20 (3H, t), 1.39 (3H, t), 2.58 (2H, q), 3.99 (2H, q), 4.54 (1H, s), 6.57–7.08 (7H, m)

4) 2-Sec-butyl-4-(4-ethoxyphenoxy)phenol
¹H-NMR (CDCl₃/TMS) δ (ppm): 0.86 (3H, t), 1.19 (3H, d), 1.40 (3H, t), 1.46–1.68 (2H, m), 2.87–2.98 (1H, m), 4.00 (2H, q), 4.62 (1H, s), 6.62–6.90 (m, 7H)

5) 2-Isopropyl-4-(4-ethoxyphenoxy)phenol
¹H-NMR (CDCl₃/TMS) δ (ppm): 1.22 (6H, d), 1.41 (3H, t), 3.13–3.22 (1H, m), 4.01 (2H, q), 4.69 (1H, s), 6.62–6.93 (7H, m)

6) 2-Tert-butyl-4-(4-ethoxyphenoxy)phenol
¹H-NMR (CDCl₃/TMS) δ (ppm): 1.39 (9H, s), 1.41 (3H, t), 4.00 (2H, q), 4.75 (1H, s), 6.56–6.98 (7H, m)

7) 2-Isopropyl-4-(4-ethoxyphenoxy)phenol
¹H-NMR (CDCl₃/TMS) δ (ppm): 1.23 (6H, d), 3.13–3.22 (1H, m), 3.77 (3H, s), 4.67 (1H, s), 6.49–7.21 (7H, m)

8) 2-n-Propyl-4-(3-ethoxyphenoxy)phenol
¹H-NMR (CDCl₃/TMS) δ (ppm): 0.96 (3H, t), 1.38 (3H, t), 1.58–1.68 (2H, m), 2.55 (2H,t), 3.98 (2H, q), 4.65 (1H, s), 6.46–7.20 (7H, m)

9) 2-Methyl-4-(4-ethoxyphenoxy)phenol
¹H-NMR (CDCl₃/TMS) δ (ppm): 1.40 (3H, t), 2.20 (3H, s), 4.00 (2H, q), 4.58 (1H, s), 6.70–6.91 (7H, m)

10) 2-Isopropyl-4-(4-isopropoxyphenoxy)phenol
¹H-NMR (CDCl₃TMS) δ (ppm): 1.22 (6H, d), 1.32 (6H, d), 3.14–3.23 (1H, m), 4.41–4.49 (1H, m), 4.61 (1H, s), 6.63–6.90 (7H, m)

11) 2-Allyl-4-(4-ethoxyphenoxy)phenol
¹H-NMR (CDCl₃/TMS) δ (ppm): 1.40 (3H, t), 3.35–3.38 (2H, m), 4.01 (2H, q), 4.78 (1H, s), 5.12–5,19 (2H, m), 5.92–6.05 (1H, m), 6.75–6.92 (7H, m)

12) 2-Chloro-5-methyl-4-(4-2,2,2-trifluoroethoxyphenoxy)phenol
$n_D^{23.5}$ 1.5342

13) 2-Isopropyl-4-(4-ethoxyphenoxy)phenol
¹H-NMR (CDCl₃/TMS) δ (ppm): 1.18 (6H, d), 1.39 (3H, t), 3.18–3.27 (1H, m), 3.99 (2H, q), 4.65 (1H, s), 6.57–6.81 (7H, m)

14) 2-n-Propyl-4-(4-isopropoxyphenoxy)phenol
¹H-NMR (CDCl₃/TMS) δ (ppm): 0.96 (3H, t), 3.32 (6H, d), 1.55–1.68 (2H, m), 2.54 (2H, t), 4.41–4.49 (1H, m), 4.52 (1H, s), 6.70–6.90 (7H, m)

15) 3-Isopropyl-4-(4-isopropoxyphenoxy)phenol
¹H-NMR (CDCl₃/TMS) δ (ppm): 1.18 (6H, d), 1.31 (6H, d), 3.17–3.28 (1H, m), 4.39–4.49 (1H, m), 4.71 (1H, s), 6.57–6.81 (7H, m)

16) 2-n-Propyl-4-(4-cyclohexylphenoxy)phenol
¹H-NMR (CDCl₃/TMS) δ (ppm): 0.97 (3H, t), 1.15–1.90 (12H, m), 2.41–2.58 (3H, m), 4.62 (1H, s), 6.62–7.23 (7H, m)

17) 3-Isopropyl-4-(4-ethoxyphenoxy)phenol
¹H-NMR (CDCl₃/TMS) δ (ppm): 1.18 (6H, d), 1.40 (3H, t), 3.17–3.28 (1H, m), 3.99 (2H, q), 4.64 (1H, s), 6.57–6.81 (7H, m)

18) 3-Methyl-4-(4-isopropoxyphenoxy)phenol
¹H-NMR (CDCl₃/TMS) δ (ppm): 1.31 (6H, d), 2.18 (3H, s), 4.39–4.48 (1H, m), 4.54 (1H, s), 6.59–6.84 (7H, m)

19) 3-Ethyl-4-(4-isopropoxyphenoxy)phenol
¹H-NMR (CDCl₃/TMS) δ (ppm): 1.17 (3H, t), 1.31 (6H, d), 2.58 (2H, q), 4.39–4.49 (1H, m), 4.62 (1H, s), 6.58–6.80 (7H, m)

20) 2-Phenyl-4-(4-isopropoxyphenoxy)phenol
¹H-NMR (CDCl₃/TMS) δ (ppm): 1.30 (6H, d), 4.41–4.50 (1H, m), 4.99 (1H, s), 6.82–6.95 (7H, m), 7.36–7.51 (5H, m)

21) 2-Isopropyl-4-(4-phenoxyphenoxy)phenol
¹H-NMR (CDCl₃/TMS) δ (ppm): 1.24 (6H, d), 3.15–3.24 (1H, m), 4.57 (1H, s), 6.71–7.34 (12H, m)

22) 2,5-Dichloro-4-(4-isopropoxyphenoxy)phenol
¹H-NMR (CDCl₃/TMS) δ (ppm): 1.33 (6H, d), 4.43–4.51 (1H, m), 5.37 (1H, brs), 6.82–6.90 (4H, m), 6.92 (1H, s), 7.13 (1H, s)

23) 2-Allyl-4-(4-isopropoxyphenoxy)phenol
¹H-NMR (CDCl₃/TMS) δ (ppm): 1.32 (6H, d), 3.35–3.38 (2H, m), 4.41–4.51 (1H, m), 4.77 (1H, s), 5.11–5.20 (2H, m), 5.91–6.07 (1H, m), 6.73–6.91 (7H, m)

24) 2-n-Propyl-4-(3-methoxyphenoxy)phenol
¹H-NMR (CDCl₃/TMS) δ (ppm): 0.97 (3H, t), 1.57–1.69 (2H, m), 2.56 (2H, t), 3.77 (3H, s), 4.67 (1H, s), 6.49–7.20 (7H, m)

25) 2-Isopropyl-4-(3-methoxyphenoxy)phenol
¹H-NMR (CDCl₃/TMS) δ (ppm): 1.23 (6H, d), 3.13–3.23 (1H, m), 3.76 (3H, s), 4.67 (1H, s), 6.50–7.21 (7H, m)

26) 2-n-Propyl-4-(3-isopropoxyphenoxy)phenol
¹H-NMR (CDCl₃/TMS) δ (ppm): 0.96 (3H, t), 1.31 (3H, d), 1.56–1.69 (2H, m), 2.55 (2H, t), 4.44–4.52 (1H, m), 4.55 (1H, s), 6.47–7.18 (7H, m)

27) 2-Isopropyl-4-(3-biphenyloxy)phenol
¹H-NMR (CDCl₃/TMS) δ (ppm): 1.24 (6H, d), 3.15–3.26 (1H, m), 4.62 (1H, s), 6.71–7.57 (12H, m)

28) 2-Trifluoromethyl-4-(3-chlorophenoxy)phenol
$n_D^{23.5}$ 1.5316

29) 2-Trifluoromethyl-4-(4-ethoxyphenoxy)phenol
$n_D^{23.5}$ 1.5322

30) 2-Trifluoromethyl-4-(4-trifluoromethylphenoxy)phenol m.p., 63.1° C.

31) 2-Trifluoromethyl-4-(4-trifluoromethoxyphenoxy)phenol $n_D^{23.5}$ 1.4910

32) 2-Trifluoromethyl-4-(4-methoxyphenoxy)phenol 33) 2-Trifluoromethyl-4-(3,4-dimethoxyphenoxy)phenol
¹H-NMR (CDCl₃/TMS) δ (ppm): 3.84 (3H, s), 3.89 (3H, s), 5.46 (1H, br), 6.50 (1H, dd), 6.60 (1H, d), 6.82 (1H, d), 6.90 (1H, d), 7.05 (1H, dd), 7.14 (1H, d)

34) 2-Trifluoromethyl-4-(3-methoxyphenoxy)phenol 35) 2-Trifluoromethyl-4-(3,5-dimethoxyphenoxy)phenol
¹H-NMR (CDCl₃/TMS) δ (ppm): 3.76 (6H, s), 5.54 (1H, br), 6.10 (2H, d), 6.20 (1H, t), 6.92 (1H, d), 7.12 (1H, dd), 7.22 (1H, d)

36) 2-Trifluoromethyl-4-(3,4-methylenedioxyphenoxy)phenol 37) 2-Trifluoromethyl-4-(3-ethoxy-4-methoxyphenoxy)phenol
¹H-NMR (CDCl₃/TMS) δ (ppm): 1.45 (3H, t), 3.87 (3H, s), 4.05 (2H, q), 5.58 (1H, brs), 6.49 (1H, dd), 6.60 (1H, d), 6.83 (1H, d), 6.92 (1H, d), 7.06 (1H, dd), 7.16 (1H, d)

38) 2-Trifluoromethyl-4-(2-chloro-4-ethoxyphenoxy)phenol
$n_D^{23.5}$ 1.5448

39) 2-Trifluoromethyl-4-(4-n-propoxyphenoxy)phenol
$n_D^{23.5}$ 1.5229

40) 2-Trifluoromethyl-4-(4-isopropoxyphenoxy)phenol
¹H-NMR (CDCl₃/TMS) δ (ppm): 1.33 (6H, d), 4.48 (1H, m), 5.37 (1H, br), 6.88 (4H, m), 6.90 (1H, d), 7.04 (1H, dd), 7.12 (1H, d)

41) 2-Trifluoromethyl-4-(4-n-butoxyphenoxy)phenol
$n_D^{23.5}$ 1.5186

42) 2-Trifluoromethyl-4-(4-(2,2,2-trifluoroethoxy)phenoxy)phenol m.p., 66.7° C.

43) 2-Trifluoromethyl-4-(3-isopropoxyphenoxy)phenol
$n_D^{23.5}$ 1.5251

44) 2-Trifluoromethyl-4-(4-cyclohexylphenoxy)phenol m.p., 83.7° C.

45) 2-Trifluoromethyl-4-(3-ethoxyphenoxy)phenol
$n_D^{23.5}$ 1.5316

46) 2-Trifluoromethyl-4-(4-phenoxyphenoxy)phenol
$n_D^{23.5}$ 1.5673

47) 2-Trifluoromethyl-4-(4-biphenyloxy)phenol
$^1$H-NMR (CDCl$_3$/TMS) δ (ppm): 5.55 (1H, br), 6.90–7.70 (12H, m)

48) 2-Trifluoromethyl-4-(4-cyclopentylphenyl)phenol
$^1$H-NMR (CDCl$_3$/TMS) δ (ppm): 1.4–2.2 (8H, m), 2.97 (1H, m), 5.32 (1H, br), 6.88 (2H, d), 7.20 (2H, d), 6.92 (1H, d), 7.08 (1H, dd), 7.17 (1H, d)

49) 2-Trifluoromethyl-4-(2,6-dichloro-4-trifluoromethylphenoxy)phenol
$^1$H-NMR (CDCl$_3$/TMS) δ (ppm): 5.46 (1H, br), 6.80–6.96 (2H, m), 7.04 (1H, d), 7.70 (2H, s)

50) 2-Trifluoromethyl-4-(4-methoxythiophenoxy)phenol
$^1$H-NMR (CDCl$_3$/TMS) δ (ppm): 2.50 (3H, s), 5.72 (1H, br), 6.88 (2H, d), 7.28 (2H, d), 6.92 (1H, d), 7.08 (1H, dd), 7.19 (1H, d)

51) 2,5-Dichloro-4-(2,6-dichloro-4-trifluoromethylphenoxy)phenol m.p., 110.2° C.

52) 2-Trifluoromethyl-4-(3-biphenyloxy)phenol
$n_D^{23.5}$ 1.5872

53) 2,6-Dichloro-4-(3-chloro-5-trifluoromethyl-2-pyridyl)aminophenol m.p., 158.6° C.

54) 2-Trifluoromethyl-4-(4-sec-butylphenoxy)phenol
$n_D^{23.5}$ 1.5218

55) 2-Trifluoromethyl-4-(4-(1-hydroxypropyl)phenoxy)phenol
$^1$H-NMR (CDCl$_3$/TMS) δ (ppm): 0.93 (3H, t), 1.80 (2H, m), 4.60 (1H, t), 5.54 (1H, br), 6.93 (1H, d), 7.10 (1H, dd), 7.19 (1H, d), 6.93 (2H, d), 7.32 (2H, d)

56) 2-Trifluoromethyl-4-(4-(1-methylbutyl)phenoxy)phenol
$^1$H-NMR (CDCl$_3$/TMS) δ (ppm): 0.65–1.00 (5H, m), 1.15–1.40 (5H, m), 2.68 (1H, m), 5.46 (1H, br), 6.80–7.40 (7H, m)

57) 2-Trifluoromethyl-4-(4-(1,1-dimethylpropyl)phenoxy)phenol
$n_D^{23.5}$ 1.5182

58) 2-Trifluoromethyl-4-(4-(1,1,3,3-tetramethylbutyl)phenoxy)phenol
$n_D^{23.5}$ 1.4113

59) 2-Trifluoromethyl-4-(4-tert-butylphenoxy)phenol
$^1$H-NMR (CDCl$_3$/TMS) δ (ppm): 1.31 (9H, s), 5.32 (1H, br), 6.87 (2H, d), 7.33 (2H, d), 6.93 (1H, d), 7.10 (1H, ddd), 7.19 (1H, d)

60) 2-Trifluoromethyl-4-(3-tert-butylphenoxy)phenol
$^1$H-NMR (CDCl$_3$/TMS) δ (ppm): 1.30 (9H, s), 5.34 (1H, br), 6.70 (1H, m), 6.95 (1H, d), 7.02–7.40 (5H, m)

61) 2-Trifluoromethyl-4-(5,6,7,8-tetrahydro-2-naphthoxy)phenol
$^1$H-NMR (CDCl$_3$/TMS) δ (ppm): 1.78 (4H, brs), 2.73 (4H, brs), 5.34 (1H, br), 6.60–7.40 (6H, m)

62) 2-Trifluoromethyl-4-(2-naphthoxy)phenol
$^1$H-NMR (CDCl$_3$/TMS) δ (ppm): 5.38 (1H, br), 6.60–7.96 (10H, m)

63) 2-Bromo-4-(3-chloro-5-trifluoromethylpyridyloxy)phenol m.p., 101.3° C.

64) 2-Trifluoromethyl-4-(3-chloro-5-trifluoromethyl-2-pyridyloxy)phenol
$^1$H-NMR (CDCl$_3$/TMS) δ (ppm): 5.79 (1H, br), 7.02 (1H, d), 7.26 (1H, dd), 7.37 (1H, d), 8.00 (1H, brs), 8.29 (1H, brs)

65) 3-Chloro-4-(3-chloro-5-trifluoromethyl-2-pyridyloxy)phenol
$^1$H-NMR (CDCl$_3$/TMS) δ (ppm): 5.89 (1H, s), 6.79 (1H, dd), 6.93 (1H, d), 7.10 (1H, d), 8.05 (1H, br), 8.28 (1H, br)

66) 2,5-Dichloro-4-(3-chloro-5-trifluoromethyl-2-pyridyloxy)phenol
$^1$H-NMR (CDCl$_3$/TMS) δ (ppm): 5.99 (1H, s), 7.11 (1H, s), 7.20 (1H, s), 7.93 (1H, brs), 8.20 (1H, brs)

67) 3,5-Dichloro-4-(3-chloro-5-trifluoromethyl-2-pyridyloxy)phenol
$^1$H-NMR (CDCl$_3$/TMS) δ (ppm): 5.81 (1H, s), 6.89 (2H, s), 8.02 (1H, brs), 8.27 (1H, brs)

68) 2,6-Dichloro-4-(3-chloro-5-trifluoromethyl-2-pyridyloxy)phenol
$^1$H-NMR (CDCl$_3$/TMS) δ (ppm): 5.94 (1H, br), 7.18 (2H, s), 7.99 (1H, brs), 8.30 (1H, brs)

69) 2-Chloro-4-(3,5-bis(trifluoromethyl)-2-pyridyloxy)phenol
$^1$H-NMR (CDCl$_3$/TMS) δ (ppm): 5.60 (1H, brs), 7.02 (1H, dd), 7.08 (1H, d), 7.21 (1H, d), 8.21 (1H, brs), 8.55 (1H, brs)

70) 3-Chloro-4-(3,5-bis(trifluoromethyl)-2-pyridyloxy)phenol
$^1$H-NMR (CDCl$_3$/TMS) δ (ppm): 5.36 (1H, s), 6.82 (1H, dd), 6.98 (1H, d), 7.10 (1H, d), 8.24 (1H, brs), 8.55 (1H, brs)

71) 2,5-Chloro-4-(3,5-bis(trifluoromethyl)-2-pyridyloxy)phenol
$^1$H-NMR (CDCl$_3$/TMS) δ (ppm): 5.60 (1H, br), 7.19 (1H, s), 7.28 (1H, s), 8.22 (1H, brs), 8.54 (1H, brs)

72) 3-Methyl-4-(3,5-bis(trifluoromethyl)-2-pyridyloxy)phenol
$^1$H-NMR (CDCl$_3$/TMS) δ (ppm): 2.13 (3H, s), 5.04 (1H, brs), 6.72 (1H, dd), 6.76 (1H, d), 6.96 (1 H, d), 8.23 (1H, brs), 8.54 (1H, brs)

73) 2,6-Dichloro-4-(3,5-bis(trifluoromethyl)-2-pyridyloxy)phenol
$^1$H-NMR (CDCl$_3$/TMS) δ (ppm): 5.89 (1H, br), 7.18 (2H, s), 8.24 (1H, brs), 8.59 (1H, brs).

74) 3,5-Dichloro-4-(3,5-bis(trifluoromethyl)-2-pyridyloxy)phenol
$^1$H-NMR (CDCl$_3$/TMS) δ (ppm): 5.75(1H, br), 6.90 (2H, s), 8.24 (1H, brs), 8.52 (1H, brs)

75) 2,5-Dichloro-4-(3-bromo-5-trifluoromethyl-2-pyridyloxy)phenol
$^1$H-NMR (CDCl$_3$/TMS) δ (ppm): 5.64 (1H, br), 7.17 (1H, s), 7.28 (1H, s), 8.16 (1H, brs), 8.30 (1H, brs)

76) 3,5-Dichloro-4-(3-bromo-5-trifluoromethyl-2-pyridyloxy)phenol
$^1$H-NMR (CDCl$_3$/TMS) δ (ppm): 6.20 (1H, brs), 6.86 (2H, s), 8.70 (1H, d), 8.80 (1H, b)

77) 4-(4-Chlorophenylthio)-2-bromophenol
$^1$H-NMR (CDCl$_3$/TMS) δ (ppm): 5.60 (1H, brs), 7.00 (1H, d, J=8.4 Hz), 7.14 (2H, d, J=8.7 Hz), 7.23 (2H, d, J=8.4 Hz), 7.30 (1H, dd, J=2.2, 8.4 Hz) 7.56 (1H, d, J=2.2 Hz)

78) 4-(1-(4-Ethoxyphenyl)-1-methylethyl)-2-bromophenol
$^1$H-NMR (CDCl$_3$/TMS) δ (ppm): 1.40 (3H, t), 1.61 (6H, s), 4.01 (2H, q), 6.80 (2H, d, J=8.6 Hz), 6.90 (1H, d, J=8.3 Hz), 7.04 (1H, dd, J=2.4, 8.2 Hz), 7.11 (2H, d, J=8.4 Hz), 7.32 (1H, dd, J=2.4 Hz)

79) 4-(4-Ethoxyphenylthio)-2-bromophenol
$^1$H-NMR (CDCl$_3$/TMS) δ (ppm): 1.41(3H, t, J=7.0 Hz), 4.02 (2H, q, J=7.0 Hz), 6.85 (2H,d, J=8.0 Hz), 6.92 (1H, d, J=8.5 Hz), 7.15 (1H, dd, J=2.2, 8.5 Hz), 7.31 (2H, d, J=8.0 Hz), 7.39 (1H, d, J=2.1 Hz)

80) 4-(1-(4-Ethoxyphenyl)-1-(trifluoromethyl)-2,2,2-trifluoroethyl)-2,5-dibromophenol $^1$H-NMR (CDCl$_3$/TMS) δ (ppm): 1.41 (3H, t), 4.07 (2H, q), 6.04 (1H, brs), 6.89 (2H, d, J=9.7 Hz), 7.27 (2H, d, J=9.6 Hz), 7.48 (2H, s)

81) 4-(4-Methoxyphenylthio)-2-(trifluoromethyl)phenol $^1$H-NMR (CDCl$_3$/TMS) δ (ppm): 3.78 (3H, s), 5.10 (1H, brs), 6.84 (1H, d, J=9.2 Hz), 6.88 (2H, d, J=8.8 Hz), 7.29 (1H, dd, J=2.2, 9.2 Hz), 7.32 (2H, d, J=8.8 Hz), 7.47 (1H, d, J=2.2 Hz)

82) 4-(4-Isopropyloxyphenylthio)-2-bromophenol

1H-NMR (CDCl$_3$/TMS) δ (ppm): 1.33 (6H, d), 4.53 (1 H, sep), 5.45 (1H, s), 6.83 (2H, d), 6.92 (1H, s), 7.16 (1H, dd), 7.29 (2H, d), 7.40 (1H, d)

83) 4-(1-(4-Isopropyloxyphenyl)-1-methylethyl)-2-bromophenol $^1$H-NMR (CDCl$_3$/TMS) δ (ppm): 1.33 (6H, d), 1.61 (6H, s), 4.51 (1H, sep), 6.82 (2H, d), 6.91 (1H, d), 7.05 (1H, dd), 7.11 (2H, d), 7.32 (1H, d)

84) 4-(4-Isopropyloxyphenyl)-methyl-2-bromophenol $^1$H-NMR (CDCl$_3$/TMS) δ (ppm): 1.33 (6H, d), 3.82 (2H, s), 4.52 (1H, sep), 5.42 (1H, s), 6.83 (2H, d), 6.94 (1H, d), 7.05 (1H, dd), 7.07 (2H, d), 7.27 (1H,d)

85) 4-(1-(4-Isopropyloxyphenyl)-ethyl)-2-bromophenol $^1$H-NMR (CDCl$_3$/TMS) δ (ppm): 1.36 (6H, d), 1.60 (3H, d), 4.05 (1H, q), 4.56 (1H, sep), 5.46 (1H, brs), 6.85 (2H, d), 6.96 (1H, d), 7.10 (1H, dd), 7.13 (2H, d), 7.33 (1H, d)

86) 4-(N-(3-chloro-5-(trifluoromethyl)-2-pyridyl)amino)-2,5-dichlorophenol $^1$H-NMR (CDCl$_3$/TMS) δ (ppm): 5.75 (1H, brs), 7.12 (1H, s), 7.62 (1H, s), 7.80 (1H, s), 8.40 (1H, s), 8.52 (1H, s)

87) 4-(1-(4-Isopropoxyphenyl)-1-methylethyl)-2-chlorophenol $^1$H-NMR (CDCl$_3$/TMS) δ (ppm): 1.33 (6H. s), 1.62 (6H, s), 5.43 (1H, s), 6.78 (2H, d). 6.89 (1H, d), 7.02 (1H, dd), 7.11 (2H, d), 7.18 (1H, d)

88) 2-Trifluoromethyl-4-(3-trifluoromethylphenoxy)phenol 89) 2-Trifluoromethyl-4-(3-phenoxyphenoxy)phenol
n$_D^{23.5}$ 1.5679

The following will describe Formulation Examples. In these Formulation Examples, "parts" are by weight unless otherwise stated.

FORMULATION EXAMPLE 1

Emulsifiable concentrates

Ten parts of each of the compounds 1 to 367 are separately dissolved in 35 parts of xylene and 35 parts of dimethylformamide. Each of the resultant mixtures is mixed with 14 parts of polyoxyethylene styrylphenyl ether and 6 parts of calcium dodecylbenzenesulfonate, and stirred sufficiently to give 10% emulsifiable concentrates for each compound.

FORMULATION EXAMPLE 2

Wettable powders

Twenty parts of each of the compounds 1 to 367 are separately added to a mixture of 4 parts of sodium lauryl sulfate, 2 parts of calcium lignin sulfonate, 20 parts of synthetic hydrated silicon hydroxide fine powder and 54 parts of diatomaceous earth, and stirred with a mixer to give 20% wettable powders for each compound.

FORMULATION EXAMPLE 3

Granular

To 5 parts of each of the compounds 1 to 367 are added 5 parts of synthetic hydrated silicon hydroxide fine powder, 5 parts of sodium dodecylbenzenesulfonate, 30 parts of bentonite and 55 parts of clay, and stirred sufficiently. Then, a suitable amount of water is added to the mixture which is further stirred, granulated with a granulated and then air-dried to give a 5% granular for each compound.

FORMULATION EXAMPLE 4

Dusts

One part of each of the compounds 1 to 367 separately dissolved in a suitable amount of acetone is mixed with 5 parts of synthetic hydrated silicon hydroxide fine powder, 0.3 parts of PAP and 93.7 parts of clay. Then, the mixture was stirred with a mixer and acetone is removed to give 1% dusts for each compound.

FORMULATION EXAMPLE 5

Flowables

Twenty parts of each of the compounds 1 to 367 are separately mixed with 1.5 parts of sorbitan trioleate and 28.5 parts of an aqueous solution containing 2 parts of polyvinyl alcohol, and the mixture is pulverized into fine particles having a particle size of not more than 3 μm with a sand grinder. Each of the mixture was mixed with 40 parts of an aqueous solution containing 0.05 parts of xanthan gum and 0.1 parts of aluminum magnesium silicate, and then mixed with 10 parts of propylene glycol to give 20% water-based suspensions for each compound.

FORMULATION EXAMPLE 6

Oil solutions

First, 0.1 parts of each of the compounds 1 to 367 are separately dissolved in 5 parts of xylene and 5 parts of trichloroethane. Then, the solution was mixed with 89.8 parts of deodorized kerosine to give 0.1% oil solutions for each compound.

FORMULATION EXAMPLE 7

Oil-based aerosol

First, 0.1 parts of each of the compounds 1 to 367, 0.2 parts of tetramethrin, 0.1 parts of d-phenothrin, 10 parts of trichloroethane are dissolved in 59.6 parts of deodorized kerosine, and an aerozol vessel is filled with the solution. Then, the vessel is equipped with a valve, through which 30 parts of a propellant (liquefied petroleum gas) are charged under pressure to give an oil-based aerosol of each compound.

FORMULATION EXAMPLE 8

Water-based aerosol

An aerosol vessel is filled with 50 parts of pure water and a mixture of 0.2 parts of each of the compounds 1 to 367, 0.2 parts of d-allethrin, 0.2 parts of d-phenothrin, 5 parts of xylene, 3.4 parts of deodorized kerosine and 1 part of an emulsifier [ATMOS 300 (registered trade mark by Atlas Chemical Co.)]. Then, the vessel is equipped with a valve, through which 40 parts of a propellant (liquefied petroleum gas) are charged under pressure to give a water-based aerosol of each compound.

FORMULATION EXAMPLE 9

Mosquito-coil

First, 0.3 g of each of the compounds 1 to 367 and 0.3 g of d-allethrin are dissolved in 20 ml of acetone, and the solution is mixed uniformly with 99.4 g of a carrier for mosquito-coil (prepared by mixing Tabu powder, dregs powder and wood flour in the ratio of 4:3:3) with stirring. Then, 120 ml of water is added to the mixture, which is kneaded sufficiently, molded and dried to give a mosquito-coil of each compound.

FORMULATION EXAMPLE 10

Electric mosquito-mat

First, 0.4 g of each of the compounds 1 to 367, 0.4 parts of d-allethrin and 0.4 g of pipenyl butoxide are separately dissolved in acetone to give 10 ml of a solution. A substrate for electric mat having a size of 2.5 cm×1.5 cm×0.3 cm in thickness (prepared by forming a fibrillated mixture of cotton linter and pulp into a sheet) is impregnated uniformly with 0.5 ml of the solution to give an electric mosquito-mat of each compound.

FORMULATION EXAMPLE 11

Heating smoke formulation

First, 100 mg of each of the compounds 1 to 367 is separately dissolved in a suitable amount of acetone. Then, a porous ceramic plate having a size of 4.0 cm×4.0 cm×1.2 cm in thickness is impregnated with the resultant solution to give a heating smoke formulation of each compound.

FORMULATION EXAMPLE 12

Poison baits

First, 10 mg of each of the compounds 1 to 367 is separately dissolved in 0.5 ml of acetone, and the solution is mixed uniformly with 5 g of solid bait powder (Breeding Solid Feed Powder CE-2, trade name by Japan Clea Co., Ltd.). Then, acetone is removed to give a 0.2% poison bait of each compound.

The following Biological Test Examples will illustrate that the dihalopropene compounds of the present invention are useful as an active ingredient of insecticides/acaricides. In these Biological Test Examples, the dihalopropene compounds of the present invention are designated by the corresponding numbers described above and the compounds used for comparison are designated by the corresponding symbols in Table 22.

TABLE 22

| Symbol of compound | Chemical Structure | Remarks |
|---|---|---|
| A | ⌬—O—⌬—OCH$_2$CH=CCl$_2$ | Compound disclosed in the Japanese Patent Laid-open Publication No. 48-86835/1973 |
| B | ⌬—CH$_2$O—⌬—OCH$_2$CH=CCl$_2$ | Compound disclosed in the Japanese Patent Laid-open Publication No. 49-1526/1974 |

BIOLOGICAL TEST EXAMPLE 1

Insecticidal test against Spodoptera litura

An emulsion was prepared from the test compound according to Formulation Example 1. Then, 13 g of an artificial diet for Spodoptera litura, which was prepared in a polyethylene cup having a diameter of 11 cm in advance, was impregnated with 2 ml of a 200-folded diluted solution of the emulsion (500 ppm) in water. Ten fourth instar larvae of Spodoptera litura were set free in the cup. After six days, the survival of larvae was examined to determine the mortality in duplicate.

As a result, it was found that the compounds 1–3, 6–14, 16–21, 23–28, 31–33, 36–45, 47–62, 64–69, 76–78, 80, 84, 86–90, 92–97, 103–114, 116–122, 124, 125, 127–133, 135, 136, 138–185, 189–216, 218–224, 226–233,236, 237, 239–242, 244–246, 248–253, 262, 265, 266, 267, 271, 273–280, 292–294, 297–303, 305, 309–313, 316, 317, 319–321,323, 329–336, 338, 339, 347, 349–356, 359–361, 363, 366 and 367 exhibited the mortality of not less than 80%. In contrast, the compounds A and B exhibited the mortality of 0%.

BIOLOGICAL TEST EXAMPLE 2

Test against *Tetranychus urticae* Koch

Ten Female imagines of *Tetranychus urticae* Koch per one leaf were allowed to parasitize to a poring bean harvested for 7 days after seeding (primary leaf stage), which was placed in a greenhouse maintained at 25° C. After 6 days, 15 ml of a chemical solution (containing 500 ppm of an active ingredient), which was prepared by diluting an emulsion of the test compound obtained according to Formulation Example 1 with water, was sprayed over a pot on a turntable. At the same time, 2 ml of the same solution was drenched in the soil. After 8 days, the degree of damage of the respective plants caused by *Tetranychus urticae* Koch was examined. The activity was evaluated according to the criteria:

−: Damage is scarcely observed.

+: Damage is slightly observed.

++: Damage is observed at the same level as in the non-treated field.

As a result, it was found that the compounds 1, 5–9, 12, 13, 19, 21–28, 31–38, 41–49, 51, 53, 55–63, 65–73, 75, 76, 79–86, 89–91, 93, 97, 100–108, 110, 115, 126–130, 136–151, 155–158, 163–165, 169, 179–181, 183, 188, 190, 191, 193, 196, 197, 200, 202, 210–213, 215, 236–239, 242–244, 247,250, 252–255, 257–262, 265, 266, 268, 270–274, 276, 277, 279, 280, 291–296, 303, 305, 309, 310, 318, 319, 323, 329–331, 333, 340–343, 348 and 363 were evaluated as "−" or "+". In the contrast, the compounds A and B were evaluated as "++".

What is claimed is:

1. An intermediate compound of the formula:

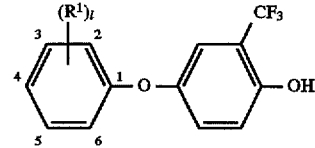

wherein l is an integer of 1 to 5; $R^1$ is halogen, $C_1$–$C_8$ alkyl, trifluoromethyl, $C_1$–$C_4$ alkoxy, $C_1$–$C_2$, $C_3$–$C_5$ alkenyloxy, $C_3$–$C_4$ haloalkenyloxy, $C_3$–$C_6$ cycloalkyl, phenyl, pyridyloxy, phenoxy or benzyl, the last four of which may be optionally substituted with halogen, $C_1$–$C_5$ alkyl, $C_1$–$C_3$ alkoxy, $C_1$–$C_3$ haloalkyl or $C_1$–$C_3$ haloalkoxy, with the proviso that when l is an integer of 2 to 5, $R^1$'s are the same or different, and when l is an integer of 1 to 3, two adjacent $R^1$'s may be combined together at their terminal ends to form trimethylene, tetramethylene, methylenedioxy, ethylenedioxy or CH=CH—CH=CH.

2. An intermediate compound of the formula:

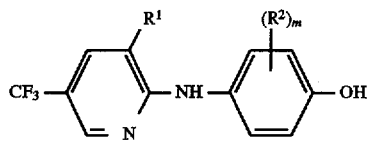

wherein $R^1$ is halogen or trifluoromethyl; $R^2$'s are the same or different and are independently halogen, trifluoromethyl or $C_1$–$C_3$ alkyl; and m is an integer of 1 to 4.

3. An intermediate compound according to claim 1, which is 2-trifluoromethyl-4-(4-isopropoxyphenoxy)phenol.

4. An intermediate compound according to claim 1, which is 2-trifluoromethyl-4-(4-cyclohexylphenoxy)phenol.

5. An intermediate compound according to claim 1, which is 2-trifluoromethyl-4-(2,6-dichloro-4-trifluoromethylphenoxy)phenol.

6. An intermediate compound according to claim 1, which is 2-trifluoromethyl-4-(5,6,7,8-tetrahydro-2-naphthyloxy)phenol.

7. A compound which is 3,5-dichloro-4-(3,5-bistrifluoromethyl-2-pyridyloxy)phenol.

8. An intermediate compound according to claim 2, which is 2,6-dichloro-4-(3-chloro-5-trifluoromethyl-2-pyridylamino)phenol.

* * * * *